(12) United States Patent
Stagljar et al.

(10) Patent No.: US 9,435,055 B2
(45) Date of Patent: Sep. 6, 2016

(54) METHOD AND KIT FOR DETECTING MEMBRANE PROTEIN-PROTEIN INTERACTIONS

(75) Inventors: Igor Stagljar, Winterthur (CH); Michael Hottiger, Uster (CH); Daniel Auerbach, Zurich (CH)

(73) Assignee: Hybrigenics Services S.A.S., Paris (FR)

( * ) Notice: Subject to any disclaimer, the term of this patent is extended or adjusted under 35 U.S.C. 154(b) by 3047 days.

(21) Appl. No.: 10/509,507

(22) PCT Filed: Mar. 28, 2003

(86) PCT No.: PCT/EP03/03287
§ 371 (c)(1),
(2), (4) Date: Dec. 22, 2004

(87) PCT Pub. No.: WO03/083136
PCT Pub. Date: Oct. 9, 2003

(65) Prior Publication Data
US 2005/0106636 A1 May 19, 2005

(30) Foreign Application Priority Data
Mar. 28, 2002 (EP) .................................... 02007427

(51) Int. Cl.
*C12N 15/00* (2006.01)
*C40B 30/04* (2006.01)
*G01N 33/50* (2006.01)
*G01N 33/68* (2006.01)

(52) U.S. Cl.
CPC ........... *C40B 30/04* (2013.01); *G01N 33/5008* (2013.01); *G01N 33/6845* (2013.01)

(58) Field of Classification Search
None
See application file for complete search history.

(56) References Cited

U.S. PATENT DOCUMENTS

| | | | |
|---|---|---|---|
| 5,646,037 A | 7/1997 | Buxton | |
| 6,251,676 B1 * | 6/2001 | Shioda et al. | 435/455 |
| 2005/0277116 A1 * | 12/2005 | McKeon et al. | 435/6 |

FOREIGN PATENT DOCUMENTS

WO   WO 02/27020 A1   4/2002

OTHER PUBLICATIONS

Ehrhard et al. Use of G-protein fusions to monitor integral membrane protein-protein interactions in yeast. Nature Biotech. 18: 1075-1079, 2000.*
Wedegaertner et al. Lipid modifications of trimeric G proteins. J. Biochem. 270(2): 503-506, 1995.*
http://seq.yestgenome.org/vectordb/vector_descrip/COMPLETE/PRS305.SEQ.html.*
Ecker et al. Chemical synthesis and expression of a cassette adapted ubiquitin gene. J. Biochem. 262(8): 3524-2527, 1987.*
Clarke et al. The structure and function of yeast centromeres. Ann. Rev. Genet. 19:29-55, 1985.*
http://www.merriam-webster.com/dictionary/episomal.*
Friedberg et al. The microsomal epoxide hydrolase has a single membrane signal anchor sequence which is dispensable for the catalytic activity of this protein. Biochem J. Nov. 1, 1994;303 ( Pt 3):967-72.*
Mumberg et al. Yeast vectors for the controlled expression of heterologous proteins in different genetic backgrounds. Gene. Apr. 14, 1995;156(1):119-22.*
Altschul, S. et al, "Gapped BLAST and PSI-BLAST: a new generation of protein database search programs", Nucleic Acids Research, vol. 25, No. 17: 3389-3402 (1997).
Angermayr, M. et al, "Stable plasma membrane expression of the soluble domain of the human insulin receptor in yeast", Federation of European Biochemical Societies, Letters 481: 8-12 (2000).
Auf Der Maur, A. et al, "Antigen-independent selection of stable intracellular single-chain antibodies", Federation of European Biochemical Societies, Letters 508: 407-412 (2001).
Bedbrook, J. et al, "Recombination between Bacterial Plasmids Leading to the Formation of Plasmid Multimers", Cell, vol. 9: 707-716 (Dec. 1976) (Part 2).
Boder, E. et al, "Yeast surface display for screening combinatorial polypeptide libraries", Nature Biotechnology, vol. 15: 553-557 (Jun. 15, 1997).
Cervantes, S. et al, "Homodimerization of presenilin N-terminal fragments is affected by mutations linked to Alzheimer's disease", Federation of European Biochemical Societies, Letters 505: 81-86 (2001).
Chubet, R. et al, <<Vectors for Expression and Secretion of FLAG Epitope-Tagged Proteins in Mammalian Cells >>, Biotechniques 20 :136-141 (Jan. 1996).
Dünnwald, M. et al, Detection of Transient In Vivo Interactions between Substrate and Transporter during Protein Translocation into the Endoplasmic Reticulum, Molecular Biology of the Cell, vol. 10: 329-344, (Feb. 1999).
Esler, W. et al, "A Portrait of Alzheimer Secretases—New Features and Familiar Faces", Science, vol. 293: 1449-1454 (Aug. 24, 2001).
Evan, G. et al, "Isolation of Monoclonal Antibodies Specific for Human *c-myc* Proto-Oncogene Product", Molecular and Cellular Biology, vol. 5, No. 12: 3610-3616 (Dec. 1985).

(Continued)

*Primary Examiner* — Michele K Joike
(74) *Attorney, Agent, or Firm* — Joyce von Natzmer; Agris & von Natzmer LLP

(57) ABSTRACT

The present invention is concerned with a method and a kit for detecting an interaction between a first membrane bound test protein or fragment thereof and a second test protein or fragment thereof which is either membrane bound or soluble with an in vivo genetic system based in yeast, bacterial or mammalian cells. The system makes use of the reconstitution of the split ubiquitin protein.

34 Claims, 19 Drawing Sheets

(56) References Cited

OTHER PUBLICATIONS

Fields, S. et al, "A novel genetic system to detect protein-protein interactions", Nature, vol. 340: 245-246 (Jul. 20, 1989).
Fields, S. et al, "The two-hybrid system: an assay for protein-protein interactions", TIG, vol. 10, No. 8: 286-292 (Aug. 1994).
Fogh, R. et al, "Solution structure of the LexA repressor DNA binding domain determined by $^1$H NMR spectroscopy", The EMBO Journal, vol. 13, No. 17: 3936-3944 (1994).
Friedberg, E., "Eukaryotic DNA repair: glimpses through the yeast *Saccharomyces cerevisiae*", Bioessays, vol. 13(6): 295-302 (Jun. 1991).
Friedberg, E., "Yeast genes involved in DNA-repair processes: new looks on old faces", Molecular Microbiology, vol. 5(10): 2303-2310 (Oct. 1991).
Fuentes, J. et al, "Clean Western Blots of Membrane Proteins after Yeast Heterologous Expression Following a Shortened Version of the Method of Perini et al", Analytical Biochemistry, 285: 276-278 (2000).
Fusco, C. et al, "In vivo Construction of cDNA Libraries for Use in the Yeast Two-Hybrid System", Yeast 15: 715-720 (1999).
Gardner, K. et al, "Structure of the Binuclear Metal-Binding Site in the GAL4 Transcription Factor", Biochemistry, 30: 11292-11302 (1991).
Gietz, R. et al, "New yeast—*Escherichia coli* shuttle vectors constructed with in vitro mutagenized yeast genes lacking six-base pair restriction sites", Gene, 74: 527-534 (1988).
Gietz, R. et al, << Genetic Transformation of Yeast >>, BioTechniques 30: 816-831 (Apr. 2001).
Golemis, E. et al, The Yeast Two-hybrid System: Criteria for Detecting Physiologically Significant Protein-Protein Interactions, Current Issues Molec. Biol.: 1(1): 31-45 (1999).
Gubler, U., "A one tube reaction for the synthesis of blunt-ended double-stranded cDNA", Nucleic Acids Research, vol. 16, No. 6: 2726 (1988).
Gudermann, T. et al, "Functional and Structural Complexity of Signal Transduction Via G-Protein-Coupled Receptors", Annu. Rev. Neurosci. 20: 399-427 (1997).
Harper, J. et al, "The p21 Cdk-Interacting Protein Cip1 is a Potent Inhibitor of G1 Cyclin-Dependent Kinases", Cell, vol. 75: 805-816 (Nov. 19, 1993).
Hernan, R. et al, "Multiple Epitope Tagging of Expressed Proteins for Enhanced Detection", BioTechniques, vol. 28, No. 4: 789-793 (Apr. 2000).
Hershko, A. et al, "The Ubiquitin System for Protein Degradation", Annu. Rev. Biochem., 61: 761-807 (1992).
Hughes, S. et al, "Two-hybrid system as a model to study the interaction of β-amyloid peptide monomers", Proc. Natl. Acad. Sci. USA, vol. 93: 2065-2070 (Mar. 1996).
James, P. et al, "Genomic Libraries and a Host Strain Designed for Highly Efficient Two-Hybrid Selection in Yeast", Genetics, 144: 1425-1436 (Dec. 1996).
Johnsson, N. et al., "Split ubiquinin as a sensor of protein interactions in vivo", Proc. Natl. Acad. Sci. USA, vol. 91:10340-10344 (Oct. 1994).
King, K. et al, "Control of Yeast Mating Signal Transduction by a Mammalian β$_2$-Adrenergic Receptor and G$_5$ α Subunit", Science, vol. 250: 121-123 (Oct. 5, 1990).
Laser, H. et al, "A new screen for protein interactions reveals that the *Saccharomyces cerevisiae* high mobility group proteins Nhp6A/B are involved in the regulation of the GAL1 promoter", PNAS, vol. 97, No. 25: 13732-13737 (Dec. 5, 2000).
MacReadie, I. et al, "Versatile Cassettes Designed for the Copper Inducible Expression of Proteins in Yeast", Plasmid 21: 147-150 (1989).
Mullis, K., << Target amplification for DNA analysis by the polymerase chain reaction >>, Ann Biol Clin (Paris), 48(8) : 579-582 (1990).

Mumberg, D. et al, Yeast vectors for the controlled expression of heterologous proteins in different genetic backgrounds, Gene, 156: 119-122 (1995).
Olayioye, M. et al, "The ErbB signaling network: receptor heterodimerization in development and cancer", The EMBO Journal, vol. 19, No. 13: 3159-3167 (2000).
Oldenburg, K. et al, "Recombination-mediated PCR-directed plasmid construction in vivo in yeast", Nucleic Acids Research, vol. 25, No. 2: 451-452 (1997).
Overton, M. et al, "G-protein-coupled receptors function as oligomers in vivo", Current Biology, 10, No. 6: 341-344 (2000).
Pan, T. et al, "Structure and function of the Zn(II) binding site within the DNA-binding domain of the GAL4 transcription factor", Proc. Natl. Acad. Sci. USA, vol. 86: 3145-3149 (May 1989).
Pausch, M., "G-protein-coupled receptors in *Saccharomyces cerevisiae*: high-throughput screening assays for drug discovery", TIBTECH, vol. 15: 487-494 (Dec. 1997).
Prado, F. et al, "New in-vivo cloning methods by homologous recombination in yeast", Curr. Genet., vol. 25(2): 180-183 (Feb. 1994).
Qiu, X. et al, "Nrdp1/FLRF is a ubiquitin ligase promoting ubiquitination and degradation of the epidermal growth factor receptor family member, ErbB3", PNAS, vol. 99, No. 23: 14843-14848 (Nov. 12, 2002).
Reiländer, H. et al, "Production of G-protein-coupled receptors in yeast", Current Opinion in Biotechnology, vol. 9: 510-517 (1998).
Richardson, J. et al, "Intracellular antibodies: development and therapeutic potential", TIBTECH, vol. 13: 306-310 (1995).
Serebriiskii, I. et al, "Two-Hybrid System and False Positives—Approaches to Detection and Elimination", Methods in Molecular Biology—Two-Hybrid Systems—Methods and Protocols, vol. 177:124-134 (2001).
Shen, F. et al, "Transcriptional Activation Domain of the Herpesvirus Protein VP16 Becomes Conformationally Constrained upon Interaction with Basal Transcription Factors", The Journal of Biological Chemistry, vol. 271, No. 9: 4827-4837 (Mar. 1, 1996).
Soellick, T. et al, << Development of an optimized interaction-mating protocol for large-scale yeast two-hybrid analyses >>, Genome Biology, vol. 2(12) : 0052.1-0052.7 (2001).
Stagljar, I. et al, A genetic system based on split-ubiquitin for the analysis of interactions between membrane proteins in vivo, Proc. Natl. Acad. Sci. USA, vol. 95: 5187-5192 (Apr. 1998).
Vojtek, A. et al, "Mammalian Ras Interacts Directly with the Serine/Threonine Kinase Raf", Cell, vol. 74: 205-214 (Jul. 16, 1993).
Wilson, I. et al, "Orphan G-protein Coupled Receptors: Novel Drug Targets for the Pharmaceutical Industry," Drug Design & Discovery, vol. 17(2):105-114 (2000).
Wilson, I. et al, "The Structure of an Antigenic Determinant in a Protein", Cell, vol. 37: 767-778 (Jul. 1984).
Wittke, S. et al, "Probing the Molecular Environment of Membrane Proteins In Vivo", Molecular Biology of the Cell, vol. 10: 2519-2530 (Aug. 1999).
Wolven, A. et al; "Palmitoylation of p59$^{fyn}$ Is Reversible and Sufficient for Plasma Membrane Association", Molecular Biology of the Cell, vol. 8: 1159-1173 (Jun. 1997).
Wu, T. et al, "Transcriptional Activation by Herpes Simplex Virus Type 1 VP16 In Vitro and Its Inhibition by Oligopeptides", Molecular and Cellular Biology, vol. 14, No. 5: 3484-3493 (May 1994).
Yang, M. et al, Protein-peptide interactions analyzed with the yeast two-hybrid system, Nucleic Acid Research, vol. 23, No. 7 (1995).
Clontech Laboratories, Inc., 'Matchmaker GAL4 Two-Hybrid System 3 & Libraries User Manual, Protocol # PT3247-1 (Version # PR94575) (Jun. 22, 1999); 38 pages.
Dünnwald et al. "Detection of Transient In Vivo Interactions Between Substrate and Transporter During Protein Translocation Into the Endoplasmic Reticulum," Molecular Biology of the Cell, 10(2), 329-344 (1999).
Johnsson et al. "Split Ubiquitin as a Sensor of Protein Interactions in vivo," Proceedings of the National Academy of Sciences USA, 91, 10340-10344 (1994).
Laser et al. "A New Screen for Protein Interactions Reveals That the *Saccharomyces cerevisiae* High Mobility Group Proteins Nhp6A/B

(56) References Cited

OTHER PUBLICATIONS

Are Involved in the Regulation of the GAL1 Promoter," *Proceedings of the National Academy of Sciences of the United States*, 97(25), 13732-13737 (2000).

Staglar et al. "A Genetic System Based on Split-Uniquitin for the Analysis of Interactions Between Membrane Proteins in vivo," *Proceedings of the National Academy of Sciences of USA*, 95, 5187-5192 (1998).

Staglar et al. "Detecting Interactions Between Membrane Proteins in vivo Using Chimeras," *Methods in Enzymology*, 327, 190-198 (2000).

Wittke et al. "Probing the Molecular Environment of Membrane Proteins in vivo," *Molecular Biology of the Cell*, 10(8), 2519-2530 (1999).

Robinson et al., "Identification of Interacting Proteins with the PROQUEST™ Two-Hybrid System," Focus, vol. 20, No. 1: 19-23 (1998).

Ausubel et al. (Ed.), Section II (Unit 13.4): "Yeast Vectors," In: Short Protocols in Molecular Biology, Second Edition, A Compendium of Methods from Current Protocols in Molecular Biology: 13-19 to 13-20 (Green Publishing Associates and John Wiley & Sons) (1992).

Criekinge & Beyaert, "Yeast Two-Hybrid: State of the Art," Biological Procedures Online, vol. 2, No. 1:1-38 (Oct. 4, 1999).

King et al., Control of Yeast Mating Signal Transduction by a Mammalian $\beta_2$-Adrenergic Receptor and $G_5$ $\alpha$ Subunit,>> Science, vol. 250: 121-123 (Oct. 5, 1990).

"PRS305—Vector Summary," at http://seq.yeastgenome.org/vectordb/vector_descrip/COMPLETE/PRS305.SEQ.html :4 pages, as of Sep. 19, 2005 ("last updated" date: Jul. 1, 1995).

Solski et al., "Targeting Proteins to Membranes Using Signal Sequences for Lipid Modification," in Methods of Enzymology, vol. 250: Lipid Modifications of Proteins (ED. Casey & Buss): 435-454 (1995, Academic Press).

Buerki, Ch., "The Membrane-Based Yeast Two-Hybrid System for Monitoring the Interaction Between Mammalian Membrane Proteins," University Zurich-Irchel, Aug. 27, 2001.

\* cited by examiner

A    beta2-adrenergic receptor expressed from
     CYC1 promoter (pCMBV1-b2AR)

B beta2-adrenergic receptor expressed from
ADH1 promoter (pAMBV1-b2AR)

SEQUENCE LISTING

```
<160> NUMBER OF SEQ ID NOS: 1

<210> SEQ ID NO 1
<211> LENGTH: 14
<212> TYPE: PRT
<213> ORGANISM: Saccharomyces cerevisiae
<220> FEATURE:
<223> OTHER INFORMATION: signal sequence

<400> SEQUENCE: 1

Met Gly Cys Thr Leu Ser Ala Glu Asp Lys Pro Gly Gly Pro
1               5                   10
```

METHOD AND KIT FOR DETECTING MEMBRANE PROTEIN-PROTEIN INTERACTIONS

This application is a national phase of international patent application no. PCT/EP03/03287, filed Mar. 28, 2003, which claims the benefit of European Application No. 02007427.4, filed Mar. 28, 2002, the entire content of which is incorporated herein by reference.

The present invention is concerned with a method for detecting membrane protein-protein interactions with an in vivo genetic system based in yeast, bacterial or mammalian cells. Furthermore, the invention provides a kit for detecting the interactions between a first membrane protein and a second protein using reconstitution of a protein involved in intracellular protein degradation such as the split ubiquitin protein. The reconstitution of split ubiquitin makes use of chimeric genes, which express hybrid proteins.

An important area in biology is the analysis of interactions between proteins. Proteins are complex macromolecules made up of covalently linked chains of amino acids. Each protein assumes a unique three-dimensional shape principally determined by its sequence of amino acids. Many proteins consist of smaller units called domains, which are continuous stretches of amino acids able to fold independently from the rest of the protein (e.g. immunoglobulin domains, immunoglobulin-like domains, GTPase domains, SH2 and SH3 domains).

Interactions between proteins mediate most processes in a living cell. They are involved, for example, in the assembly of enzyme subunits, antigen-antibody reaction, in forming the supramolecular structures of ribosomes, filaments and viruses. A special and specific role can be attributed to membrane proteins. They are involved in the transport of molecules; in the interaction of receptors on the cell surface with growth factors and hormones; membrane-bound oncogene products can give rise to neoplastic transformation through protein-protein interactions with proteins called kinases whose enzymatic activity on cellular target proteins leads to a cancerous state. Other examples of a protein-protein interaction in membranes occur when a virus infects a cell by recognizing a protein (receptor) on the surface, and this interaction has been used to design antiviral agents. There are two types of transmembrane proteins: Type I transmembrane proteins have their C-terminus in the cytoplasm, whereas the Type II transmembrane proteins have their C-terminus outside the cell (or in the inner part of some other organelle, for example in the lumen of the endoplasmic reticulum).

Protein-protein interactions have been generally studied in the past ten years by using biochemical techniques such as cross-linking, co-immunoprecipitation and co-fractionation by chromatography. Biochemical methods have the disadvantage that interacting proteins are generally known as bands of a particular mobility on a polyacrylamide gel. To progress from these bands to cloned genes is often a very tedious process.

A genetic system that is capable of rapidly detecting which proteins interact with a known protein, determining which domains of the proteins interact, and providing the genes for the newly identified interacting proteins has been developed in 1989 by Stan Fields and Ok-Kyu Song [Fields, S. and Song, O.-K., Nature 340, 245-248 (1989)]. Their system, termed yeast two-hybrid system, is based on reconstitution of a transcriptional activator and transcriptional activation of reporter genes. The yeast two-hybrid system is a powerful method for the in vivo analysis of protein-protein interactions, but is naturally limited to the analysis of soluble proteins or soluble domains of membrane proteins, i.e. interactions between integral membrane proteins cannot be studied. In addition, the hybrid proteins are targeted to the nucleus where the interactions take place. Thus, the interactions that are dependent on post-translational modifications that take place within the endoplasmatic reticulum, such as glycosylation and disulfide bond formation, may not occur.

The split-ubiquitin system represents an alternative assay for the in vivo analysis of protein interactions. It was developed in 1994 by Nils Johnsson and Alexander Varshavsky [Johnsson, N. and Varshavsky, A., Proc. Natl. Acad. Sci. USA 91, 10340-10344 (1994)] for the detection of interactions between soluble proteins (FIG. 1). Ubiquitin (Ub) is a 76 amino acid residue, single domain protein that is present in cells either free or covalently linked to other proteins. Ubiquitin plays a role in a number of processes primarily through routes that involve protein degradation. In eukaryotes, newly formed Ub fusions are rapidly cleaved by ubiquitin specific proteases (UBPs) after the last residue of Ub at the Ub-polypeptide junction. The cleavage of a UB fusion by UBPs requires the folded conformation of Ub. When a C-terminal fragment of ubiquitin (CbM) is expressed as a fusion to a reporter protein, the fusion is cleaved only if an N-terminal fragment of Ubiquitin (NbM) is also expressed in the same cell. This reconstitution of native ubiquitin from its fragments, detectable by the in vivo cleavage assay, is not observed with a mutationally altered NbM. However, if CbM and the altered NbM are each linked to polypeptides that interact in vivo, the cleavage of the fusion containing CbM is restored, yielding a generally applicable assay for detecting the protein-protein interactions (FIG. 1).

The system was subsequently modified and shown to work with membrane proteins [I. Stagljar et al., Proc. Natl. Acad. Sci. USA 95, p. 5187-5192, 1998)]. Three yeast membrane proteins of the endoplasmic reticulum have been used as a model system. Wbp1p and Ost1p are both subunits of the oligosaccharyl transferase membrane protein complex. The Alg5 protein also localizes to the membrane of the endoplasmic reticulum, but does not interact with the oligosaccharyltransferase. Specific interactions were detected between Wbp1p and Ost1p, but not between Wbp1p and Alg5p. Therefore, the modified split-ubiquitin system works as a detection system for interactions involving membrane-associated proteins. In contrast to the conventional two-hybrid system, which requires nuclear localization, the interactions are detected in their natural environment of the protein of interest. According to this prior art, the constructs used for establishing the split-ubiquitin system were designed for integration into the host genome.

However, none of the aforementioned prior art suggests a genetic method that works for the detection of in vivo membrane protein-cytosol protein interactions as well as for membrane protein-membrane protein interactions using transcriptional activation as an assay. Moreover, the above prior art showed poor reproducibility since the signal strength obtained largely depended on the site of integration of the constructs into the host genome.

It is therefore an object of the present invention to provide a method for detecting in vivo protein interactions of membrane proteins with membrane proteins as well as membrane proteins with cytosolic (soluble) proteins which method is free of the weaknesses of the prior art.

A further object of the present invention is to provide a method for the screening of libraries for identifying molecules which may interact with a membrane-bound protein.

Yet another object of the present invention is to provide a method which can be used to identify compounds that are capable of interfering with protein-protein interactions, wherein at least one protein of the interaction is a membrane bound protein. Yet another object of the present invention is to provide a method which can be used in the identification/design of peptides capable of interfering with protein-protein interactions, wherein at least one protein of the interaction is a membrane bound protein.

Yet another object of the present invention is to provide a method which can be used in the identification/design of scFVs or antibodies that are capable of interfering with protein-protein interactions, wherein at least one protein of the interaction is a membrane bound protein.

Yet another object of the present invention is to provide a method which can be used to identify compounds that bind to and activate G protein-coupled receptors (GPCRs) or that selectively bind to and activate one GPCR but not another GPCR that is coexpressed within the same cell.

These and other objects are achieved by the present invention, which provides a method as set forth herein, a kit for detecting interactions between either two membrane proteins or one membrane and one cytosolic protein as set forth herein, and vectors as set forth herein. The method is based on the reconstitution of a protein involved in intracellular protein degradation, such as ubiquitin and which makes use of chimeric genes, which express hybrid proteins. Two types of hybrid proteins are prepared. The first hybrid contains a membrane protein of interest (bait) fused to e.g. the CbM-TDA module (containing C-terminal domain of ubiquitin (CbM) followed e.g. by an artificial transcriptional activator (e.g. LexM-B42)). The second hybrid protein (prey) contains e.g. an N-terminal domain of ubiquitin (NbM) fused to the second test protein. The prey protein can be either a membrane protein or a soluble cytoplasmic protein. If two test proteins are able to interact, they reconstitute two separate ubiquitin domains into an active ubiquitin leading to the cleavage of the transcriptional activator and activation of the reporter system.

One advantage of this method is that a multiplicity of membrane proteins can be simultaneously tested to determine whether any interact with a known protein. For example, a DNA fragment encoding the membrane protein of interest (bait) is fused to a DNA fragment encoding the CbM-LexM-B42 fusion. This hybrid is introduced into the host cell (yeast, bacterial or mammalian cells) carrying (a) marker gene(s). For the second partner, (prey), a library of plasmids can be constructed which may include, for example, total human complementary DNA (cDNA) fused to the DNA sequence encoding the N-terminal domain of Ubiquitin (NbM). This library is introduced into the yeast cells carrying bait protein. If any individual plasmid from the library encodes a protein that is capable of interacting with the membrane bait protein, a positive signal will be obtained. In addition, when an interaction between proteins occurs, the gene for the newly identified protein is available.

The system further allows the identification of compounds which are capable of interfering with the protein/protein interaction as described above. In such an approach, the method according to the invention is performed in the presence and absence of a compound and compound library, respectively, and it is determined as to whether the presence of such a compound may alter the signal obtained for a positively measured protein/protein interaction in the absence of any compound to be tested.

The system can be of value in the identification of new genes. For example, membrane bound receptors may be identified that interact with a known membrane protein. Proteins that interact with oncogene-encoded membrane proteins may be discovered, and these proteins will be of therapeutic value.

The system can be used in the design of peptide/small molecule inhibitors. For example, peptides/small molecules that interact with membrane-bound growth factor receptors can be identified and then tested in other systems for their ability to inhibit the signal transduction. Peptides/small molecules that bind to bacterial or viral membrane proteins can be identified and then tested in other systems for their ability to inhibit these bacteria or viruses.

The system can be used to test affinity reagents for protein purification. Peptides or protein domains can be identified that interact with the known membrane protein of interest and these may then be used in a purification protocol for the known protein.

The term "NbM" as used herein refers to the N-terminal portion of yeast ubiquitin, which encompasses amino acids 1-37 of yeast ubiquitin. "NbM" contains either the amino acids 1-37 of wild type ubiquitin, or the amino acids 1-37 of mutated ubiquitin where e.g. the amino acid isoleucine at position 13 has been exchanged for any of the following amino acids: leucine, valine, alanine or glycine, or amino acids 1-37 of ubiquitin where the amino acid isoleucine at position 3 has been exchanged for any of the following amino acids: leucine, valine, alanine or glycine, or most preferably, amino acids 1-37 of ubiquitin where the amino acids isoleucine at position 3 and 13 have been exchanged for any of the following amino acids: leucine, valine, alanine or glycine.

The term "CbM" as used herein refers to the C-terminal portion of yeast ubiquitin, which encompasses amino acids 35-76 of yeast ubiquitin or amino acids 35-76 of mutated ubiquitin, where e.g. the amino acid lysine at position 48 has been changed to the amino acid glycine using standard site-directed mutatgenesis techniques (following, for instance, directions described in the STRATAGENE Quick-change Mutagenesis Kit, Stratagene, Calif., USA). The exchange of lysine at position 48 for the inert glycine represents an important advantage over other variations of the Split-ubiquitin technique (Dunnwald et al., 1999, Johnsson & Varshavsky, 1994, Laser et al., 2000, Stagljar et al., 1998, Wittke et al., 1999) because it prevents modification of CbM via the attachment of ubiquitin moieties. The poly-ubiquitination of unmodified CbM may interfere with the binding to NbM and may lead to the degradation of the bait polypeptide by enzymes of the ubiquitination pathway (Hershko & Ciechanover, 1992).

The term "bait" as used in this document defines a fusion of a polypeptide and one or more other polypeptides, one of which is a first protein sequence involved in intracellular protein degradation such as CbM. The bait can be used in the membrane-based yeast two-hybrid system (MbY2H system) to investigate interactions between said bait and one or several preys.

The term "bait vector" as used in this document refers to a nucleic acid construct which contains sequences encoding "the bait" and regulatory sequences that are necessary for the transcription and translation of the encoded sequences by the host cell, and preferably regulatory sequences that are needed for the propagation of the nucleic acid construct in yeast and *E. coli*. Preferably the "bait vector" also encodes the activator of the host reporter gene(s).

The term "prey" as used in this document defines a fusion between a polypeptide and one or more other polypeptides, one of which is a second protein sequence involved in intracellular protein degradation such as NbM. NbM may be either wild type NbM (then termed NbM) or a mutated version of NbM, where one or several of its amino acids have been replaced by other amino acids, as described in detail for "NbM" above.

The terms "prey vector" and "library vector" as used herein refer to a nucleic acid construct which contains sequences encoding the "prey" and regulatory sequences that are necessary for the transcription and translation of the encoded sequences encoding by the host cell, and preferably regulatory sequences that are needed for the propagation of the nucleic acid construct in yeast and *E. coli*.

The term "split-ubiquitin" as used herein refers to quasi-native yeast ubiquitin assembled from noncovalently linked NbM and CbM, which have been brought into close spatial proximity by the interaction of two unrelated polypeptides that are fused to CbM and NbM, respectively. Split-ubiquitin is recognized by ubiquitin-specific proteases present in the yeast cell, which attack the polypeptide chain C-terminal to the double glycine motif in CbM. The proteolytic cleavage leads to the breakage of the polypeptide chain after the double glycine motif.

The term "transactivator polypeptide" or "activator" as used in this document refers to any polypeptide that possesses the ability to activate the "reporter gene" of the host cell, e.g. by recruiting and activating the RNA Polymerase II machinery of yeast. Preferably, the transactivator polypeptide is the Herpes simplex virus VP16 protein and most preferably, it is the acidic B42 domain.

The term "LexM" as used in this document refers to the nucleic acid sequence encoding the bacterial repressor protein LexA or its translation product, where the sequence may either encode the wild type LexA sequence or a mutated LexA sequence where the amino acid arginine at position 157 has been replaced by a glycine or where the amino acid arginine at position 159 has been replaced by glutamate or glycine, or any combination of the two mutations.

The term Gal1-74 as used in this document refers to the nucleic acid sequence encoding the yeast protein Gal4, corresponding to amino acids 1-74 of its translation product.

The term Gal1-93 as used in this document refers to the nucleic acid sequence encoding the yeast protein Gal4, corresponding to amino acids 1-93 of its translation product.

The term "artificial transcription factor" as used in this document refers to a hybrid protein consisting of (1) a polypeptide with the intrinsic ability to bind to a defined nucleic acid sequence, such as the bacterial repressor protein LexA or the yeast Gal4 protein or the *Drosophila melanogaster* proteins Ubx and abd-A and (2) any transactivator polypeptide, as defined above.

The term "TDA" as used in this document refers to a nucleic acid sequence or its translation product, comprising the following elements: (1) an epitope tag which allows the immunological detection of the polypeptide by means of an antibody directed specifically against the epitope, such as HA tag, 3xFLAG tag, 3xMyc tag, (2) an artificial transcription factor.

The term "reporter strain" as used in this document refers to any host that contains at least one "reporter gene" such as a yeast strain that contains nucleic acid constructs, either integrated into its genome, or as autonomously replicating elements, that produce a signal upon activation by the activator, e.g. by conferring the ability to grow on selective medium when activated or leading to cell death or cell cycle arrest when activated or leading to production of enzymes such as β-galactosidase. Preferably, the host cell comprises more than one reporter gene.

The term "reporter gene" as used in this document refers to a nucleic acid sequence comprising the following elements: (1) a binding site for an artificial transcription factor, (2) a minimal promoter sequence, which may be any sequence derived from a yeast promoter, but which preferably is any of GAL1 promoter, GAL2 promoter, CYC1 promoter, SPO1 promoter, HIS3 promoter, (3) a nucleic acid sequence encoding a polypeptide which can be selected for or against in yeast or which has an enzymatic activity that can be measured using an appropriate assay, such as HIS3, ADE2, URA3, FAR1, lacZ, and (4) a terminator sequence from a yeast gene, such as CYC1 or ADH1. The nucleic acid sequence may be integrated into the genome of a yeast reporter strain or it may supplied on an autonomously replicating plasmid.

The term "FAR1" refers to the nucleic acid sequence encoding the yeast FAR1 gene or to its gene product, where the amino acid serine at position 87 has been replaced by the amino acid proline in order to stabilize the protein and prevent its degradation by the proteasome machinery for yeast.

The term "5-FOA" as used in this document refers to the compound 5-fluoroorotic acid, which may be converted into toxic metabolites by the action of the URA3 gene product, leading to cell death.

As used herein, "first membrane bound protein or part thereof" refers to a protein which is bound to or integrated into the membrane of cells such as the type I and type II transmembrane membranes or the so-called "selfactivators" which are soluble proteins having, however, been modified by the attachment of e.g. a myristylation site, which site attaches the soluble "selfactivator" to the cell membrane. In the context of the present invention, any "part" of such protein can be used as long as it is capable of being attached to the membrane and capable of interacting with the second protein strongly enough so that split-ubiquitin is formed.

As used herein, the "second protein or part thereof" refers to a protein which can interact with the "first membrane bound protein or part thereof" and which protein can be also a membrane bound protein or a soluble protein. In the context of the present invention, a part of such protein is sufficient as long as it is capable of interacting with the "first membrane bound protein or part thereof", strong enough that split-ubiquitin is formed.

"First protein sequence involved in intracellular protein degradation" and "second protein sequence involved in intracellular protein degradation" means parts of a protein which, when brought together in a host cell, e.g. by the interaction of the first protein to be tested and the second protein to be tested, reconstitutes a structure which is capable of activating an intracellular protein degradation machinery such as the ubiquitin depending proteases.

A method for detecting the interaction between a first membrane protein and a second (membrane or soluble) protein is provided in accordance to the present invention which method comprises the following steps:

(a) providing a host cell containing at least one detectable gene (reporter gene) having a binding site for a transcriptional activator, such that the detectable gene expresses a detectable product, preferably a protein, when the detectable gene is transcriptionally activated;

(b) providing, as part of a bait vector, a first chimeric gene capable of being expressed in said host cell, the first chimeric gene coding inter alia for a first membrane protein or part thereof which gene is attached to the DNA-sequence of a first module encoding inter alia a first protein sequence involved in intracellular protein degradation and a transcriptional activator, said first protein or part thereof to be tested whether it can interact with a second protein or part thereof;

(c) providing, as part of a prey vector, a second chimeric gene capable of being expressed in said host cell, the second chimeric gene coding inter alia for a second protein or part thereof which is either membrane bound or soluble and which gene is attached to the DNA sequence of a second module encoding inter alia a second protein sequence involved in intracellular protein in degradation; and (d) introducing the bait vector and the prey vector into the host cell such that an interaction between the expressed first and second protein and/or their parts can take place, which interaction leads to an interaction of the first protein sequence of the first module and the second protein sequence of the second module which interaction in turn leads to activation of an intracellular protease and proteolytic separation of the transcriptional activator, at least one of the bait and prey vectors, preferably both, being suitable for being maintained episomally.

The method is set up in yeast, preferably in *Schizosaccharomyces pombe*, most preferably in the budding yeast *Saccharomyces cerevisiae*, but can be set up as well in bacteria such as *Escherichia coli* and mammalian cell systems. The host cell contains a detectable gene having a binding site for a transcriptional activator, preferably TDA, such that the detectable gene expresses a detectable protein when the detectable gene is transcriptionally activated.

The first chimeric gene is provided which is capable of being expressed in the host cell. The first chimeric gene contains a DNA coding for a first membrane protein fused to TDA, and a first protein sequence involved in intracellular protein degradation, such as CbM. This first protein is then tested for interaction with a second protein or protein fragment.

A second chimeric gene is provided which is capable of being expressed in the host cell. The second chimeric gene contains a DNA sequence that encodes a second hybrid protein. The second hybrid protein contains e.g. an N-terminal domain of Ubiquitin (NbM). The second hybrid protein also contains a second protein or a protein fragment which is to be tested for interaction with the first protein or protein fragment. The second hybrid protein may be encoded in a library of plasmids that contain genomic, cDNA or synthetically generated DNA sequences fused to the DNA sequence encoding the N-terminal domain of Ubiquitin (NbM). The interaction between the first membrane protein and the second protein in the host cell, therefore, causes the cleavage of the transcriptional activator that activates transcription of the reporter gene(s). The method may be carried out by introducing the first chimeric gene and the second chimeric gene into a yeast reporter strain. The host cell is subjected to conditions under which the first membrane protein and the second protein are expressed in sufficient quantity for the reporter gene to be activated. The cells are then tested for the expression of a reporter gene, which is activated to a greater degree than in the absence of an interaction between the first protein and the second protein.

In this way interactions between a first membrane protein and a library of proteins can be tested. For example, the first membrane protein may be derived from a bacterial membrane protein, a viral membrane protein, an oncogene-encoded membrane protein, a growth-factor receptor or any eukaryotic membrane protein. The second protein may be derived from a library of plasmids as described above.

The method of the present invention may be practiced using a kit for detecting interaction between a first membrane protein and a second protein comprising the following elements:

(a) a host cell containing at least one detectable gene (reporter gene) having a binding site for a transcriptional activator, such that the detectable gene expresses a detectable product, preferably a protein, when the detectable gene is transcriptionally activated;

(b) a first vector (bait) comprising a first site capable of receiving a first nucleic acid coding for a first membrane protein or part thereof such that when the first nucleic acid is inserted it becomes attached to the DNA sequence of a first module encoding inter alia a first protein sequence involved in intracellular protein degradation, the module further comprising a nucleic acid for a transcriptional activator;

(c) a second vector (prey) comprising a second site capable of receiving a second nucleic acid coding for a second membrane protein or a soluble protein or part thereof such that when the second nucleic acid is inserted it becomes attached to the DNA sequence of a second module encoding inter alia a second protein sequence involved in intracellular protein degradation; and optionally (d) a plasmid library encoding second proteins or parts thereof.

The kit may include a container, vectors and a host cell. The vectors for the membrane based detection system include the bait vector and prey vector and optionally a plasmid library, such vectors are for example shown in FIG. 2 as vector (p-Y-CbM-TDA), that allows to assay any Type I transmembrane protein (Y), contains a yeast promoter selected from the group consisting of the ADH promoter, CYC1 promoter and TEF promoter, followed by unique restriction sites for inserting a DNA sequence encoding a membrane protein in such a manner that the first protein is expressed as a fusion to the CbM-LexM-B42 portion. The first vector also contains a terminator sequence which is necessary to terminate the transcription of a given membrane protein. The first vector in one embodiment does not include a sequence that allows its replication in yeast, but preferably contains such a sequence an alternative embodiment, allowing episomal replication of the vector. This vector may be an integrative vector that has to be stable integrated in the yeast genome. Also included on the first vector is a first marker gene (e.g. LEU2), the expression of which in the host cell permits selection of cells containing the first marker gene from cells that do not contain the first marker gene.

A second vector (e.g. pTDA-CbM-Y), that allows to assay any Type II transmembrane protein (Y), contains a yeast promoter selected from the group consisting of the ADH promoter, CYC1 promoter and TEF promoter, followed by unique restriction sites for inserting a DNA sequence encoding a membrane protein in such a manner that the first protein is expressed as a fusion to LexM-B42-CbM portion (FIG. 2). Note that there is an inverted orientation of the transcription factor fused to the TDA portion. The second vector might also contain a terminator sequence which is necessary to terminate the transcription of a given test membrane protein. The second vector, in a first embodiment, does not include a sequence that allows its replication in yeast. However, a second embodiment includes a sequence which allows episomal replication of the vector. As the first vector, this vector may be an integrative vector that has to be stable integrated in the yeast genome. Also included on the second vector is a marker gene (LEU2), the expression of which in the host cell permits selection of cells containing the first marker gene from cells that do not contain the first marker gene.

A third vector (e.g. pX-HA-NbM) that allows the cloning of the prey protein (X), may be a transmembrane protein or soluble (cytoplasmic) protein (FIG. 2). The test protein may be encoded in a library of plasmids that contain genomic, cDNA or synthetically generated DNA sequences fused to the NbM domain. The third vector also includes a promoter preferably selected from the group consisting of the ADH promoter, CYC1 promoter and TEF promoter, and does include a transcription termination signal to direct transcription. It also includes a DNA sequence that encodes the N-terminal domain of Ubiquitin (NbM) and a unique restriction site to insert a DNA sequence encoding the second protein or protein fragment into the vector. Thus, the third vector allows the cloning of the protein as an N-terminal fusion to the NbM domain. The third vector further preferably includes a means for replicating itself in the host cell, i.e. yeast or bacteria. It also includes a second marker gene such as (TRP1), the expression of which in the host cell permits selection of cells containing the second marker gene from cells that do not contain the second marker gene.

A fourth vector (pNbM-HA-X) allows the cloning of the prey protein (X), a transmembrane protein or soluble (cytoplasmic) protein, as a C-terminal fusion to the NbM domain (FIG. 2). The fourth vector also includes a promoter preferably selected from the group consisting of the ADH promoter, CYC1 promoter and TEF promoter, and transcription termination signal to direct transcription. It also includes a DNA sequence that encodes the N-terminal domain of ubiquitin (NbM) and a unique restriction site to insert a DNA sequence encoding the second protein or protein fragment into the vector. The fourth vector further preferably includes a means for replicating itself in the host cell and in bacteria. It also includes a second marker gene (such as TRP1), the expression of which in the host cell permits selection of cells containing the second marker gene from cells that do not contain the second marker gene.

While vectors published by Stagljar et al. [Proc. Natl. Acad. Sci. USA 95, 5187-5192 (1998)] enabled the expression of the yeast Wbp1p, Ost1p and Alg5p only, the newly designed vectors enable now the cloning of any desirable membrane "bait" protein into e.g. pCbM-TDA and pTDA-CbM, and any desirable "prey" protein or a genomic/cDNA library into e.g. pNbM-HA-X or pX-HA-NbM vectors. For easy immunological detection pNbM-HA-X and pX-HA-NbM are tagged with a haemaglutinine(HA) epitope. All vectors were confirmed by DNA sequencing.

The kit includes a host cell, preferably a yeast or bacterial strain that contains a detectable gene having binding sites for the artificial transcription factor such as PLV. The binding site is positioned so that the reporter gene expresses a reporter protein when two proteins (the first protein and the second protein) properly interact in this system. The host cell, by itself, is incapable of expressing a protein having a function of the first marker gene (LEU2), the second marker gene (TRP1), the CbM-TDA portion, or the NbM domain.

The basic strategy of the testing method is shown in FIG. 1. The method is based on the previously developed split-ubiquitin technique. The split-ubiquitin technique is based on the ability of NbM and CbM, the N- and C-terminal halves of Ub, to assemble into quasi-native Ubiquitin. Ubiquitin-specific proteases (UBPs), which are present in all eukaryotic cells, recognize the reconstituted Ubiquitin, but not its halves, and cleave the Ubiquitin moiety off a reporter protein that had been linked to NbM or CbM, preferably to the C terminus of CbM. Quite in analogy to the two-hybrid system, the liberation of the reporter serves as a readout indicating the reconstruction of Ubiquitin. The assay is designed in a way that prevents efficient association of NbM and CbM by themselves, but allows it if the two Ubiquitin halves are separately linked to proteins that interact in vivo.

Figure 3A:
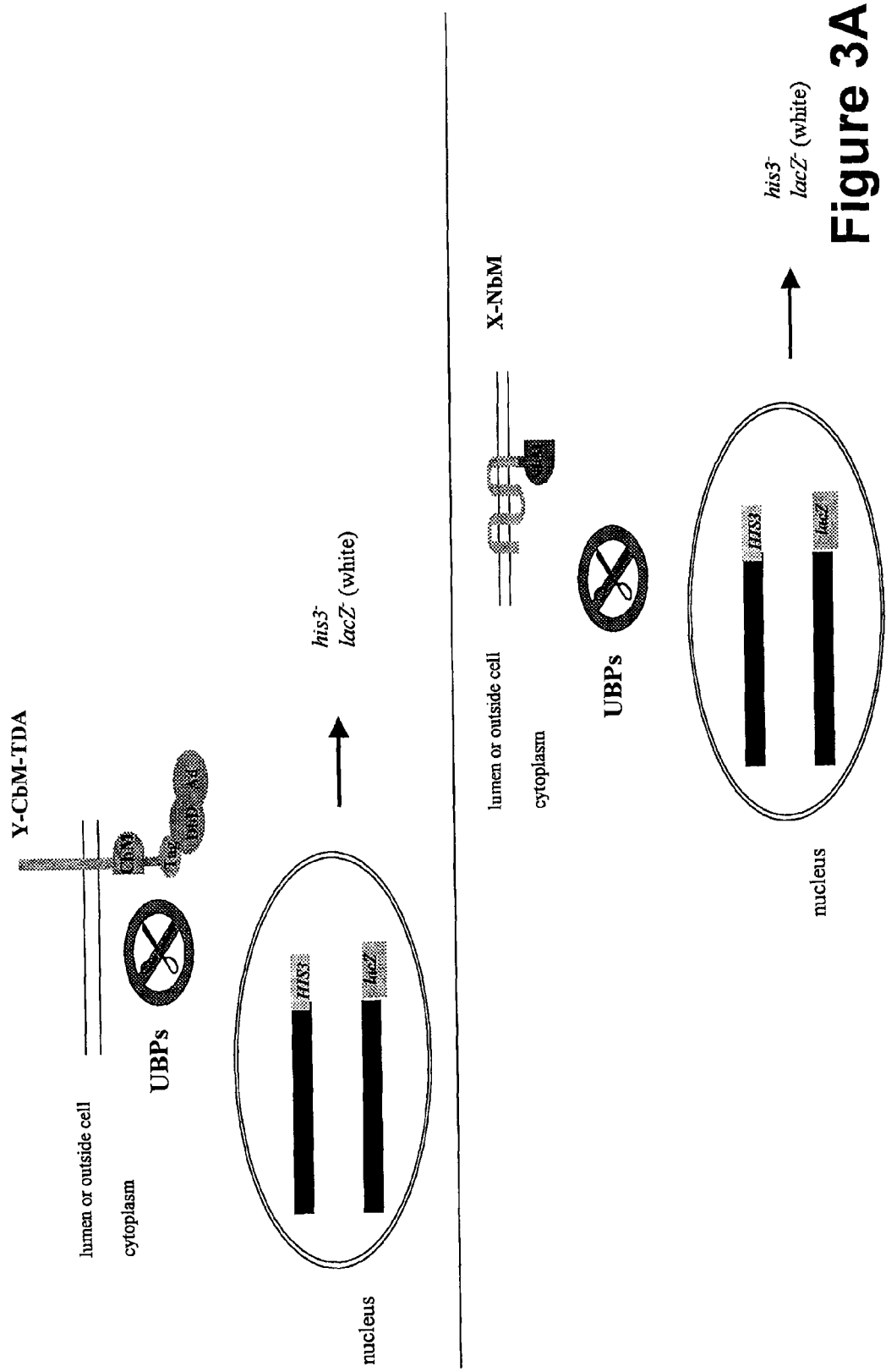

FIG. 3A schematically illustrates two test membrane proteins, Y and X. The first chimeric protein contains the Type I transmembrane bait protein Y fused to the CbM-TDA portion resulting in Y-CbM-TDA protein. The second chimeric protein contains a second interacting protein X (here depicted as a membrane protein) fused to the NbM domain called X-NbM. Neither of these proteins, Y-CbM-TDA and X-NbM, is able to activate transcription.

Figure 3B:
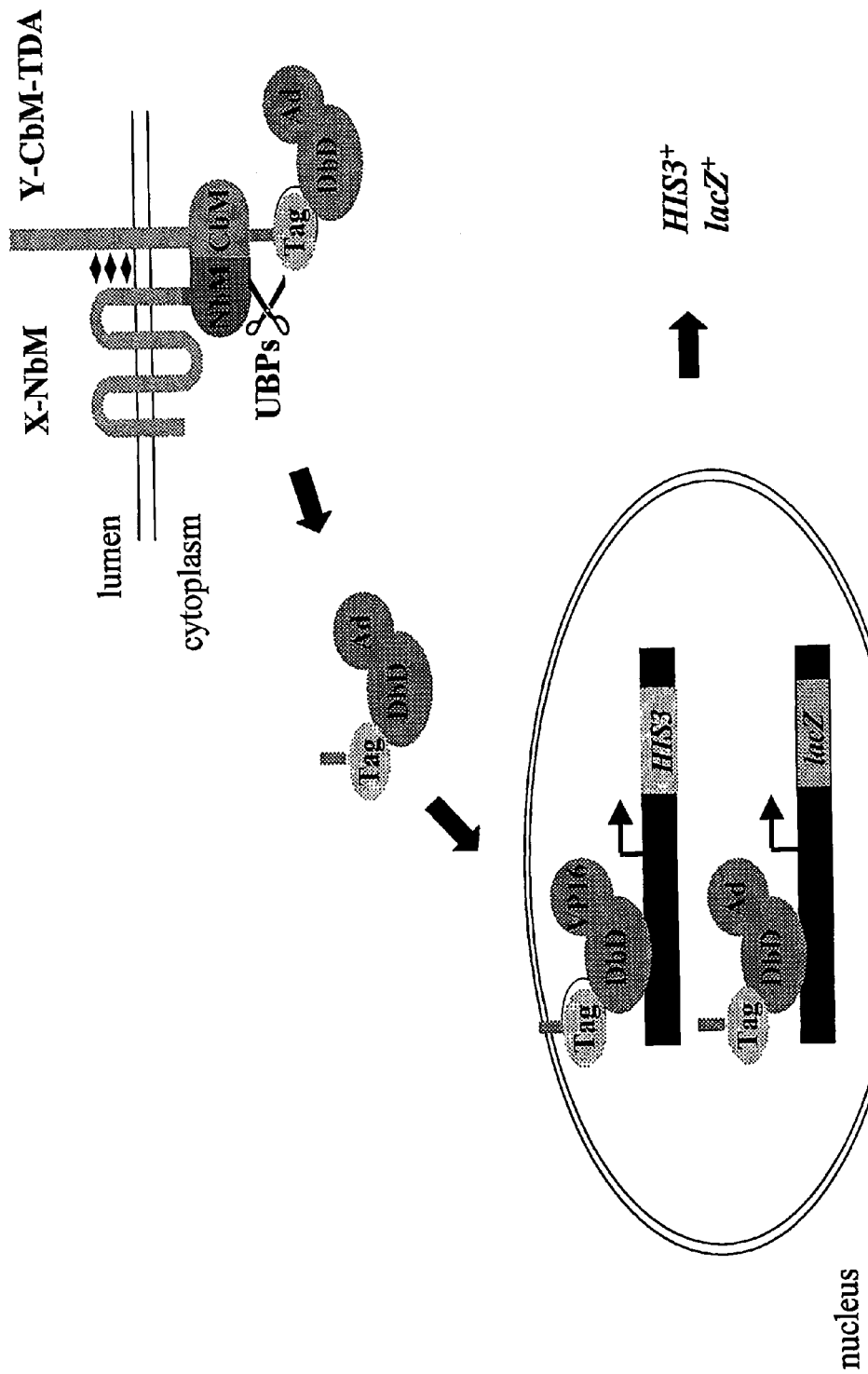

FIG. 3B. The interaction of proteins Y and X, results in reassociation of NbM and CbM to form split-ubiquitin. Split-ubiquitin is recognized and cleaved by the ubiquitin specific proteases (UBPs) (open scissors), liberating TDA. The TDA can enter the nucleus by diffusion and bind to the LexA-binding sites, leading to activation of transcription of the lacZ and HIS3 reporter genes. This results in blue cells in the presence of X-gal and growth of the cells on agar plates lacking histidine.

Figure 3C:
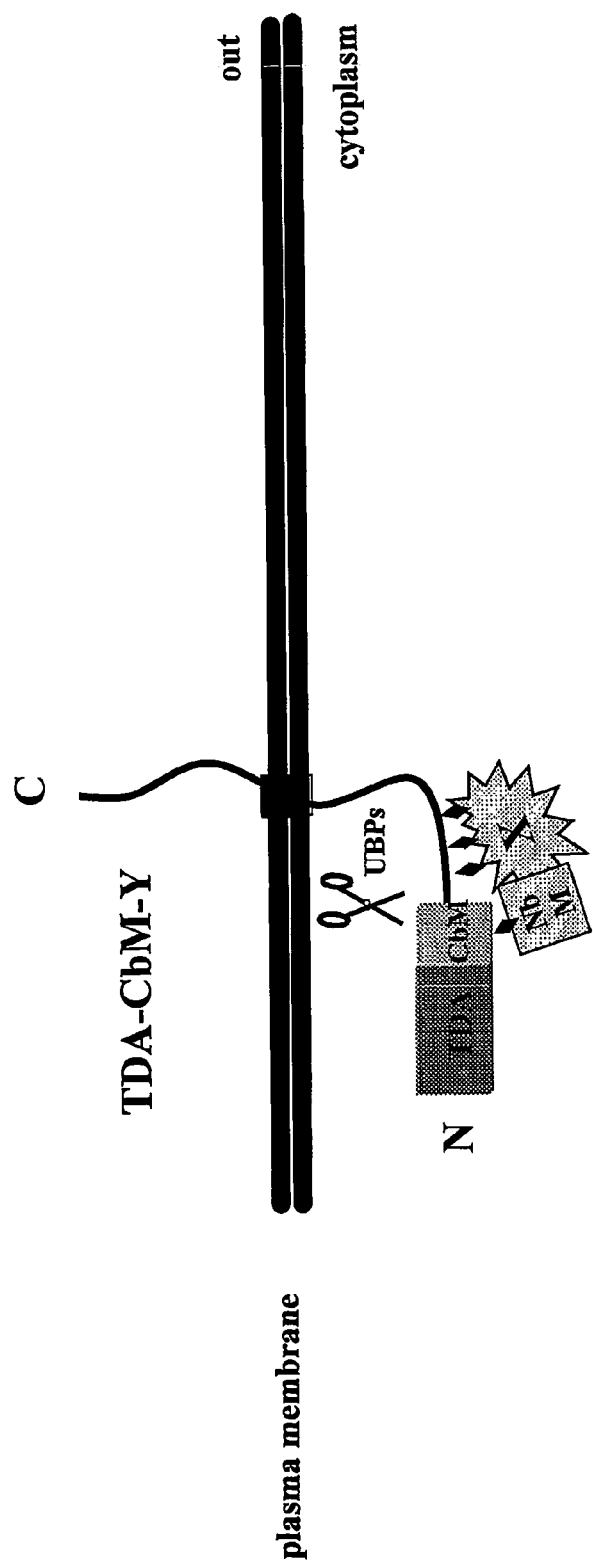

FIG. 3C. Schematical illustration of the interaction between a Type II transmembrane protein (Y) and a cytoplasmic protein (X). The first chimeric protein contains the bait protein Y fused to the TDV-CbM portion resulting in TDA-CbM-Y protein. The second chimeric protein contains a second interacting protein X (here depicted as a cytoplasmic protein) fused to the NbM domain called NbM-X. Neither of these proteins, TDA-CbM-Y and NbM-X, is able to activate transcription. The interaction of proteins Y and X, as illustrated in FIG. 3c, results in formation of split-ubiquitin. Split-ubiquitin is recognized and cleaved by the ubiquitin specific proteases (UBPs) (open scissors), liberating TDV-CbM. The TDV-CbM can enter the nucleus by diffusion and bind to the LexA-binding sites leading to activation of transcription of the lacZ and HIS3 reporter genes. This results in blue cells in the presence of X-gal and growth of the cells on agar plates lacking histidine.

Figure 4A:
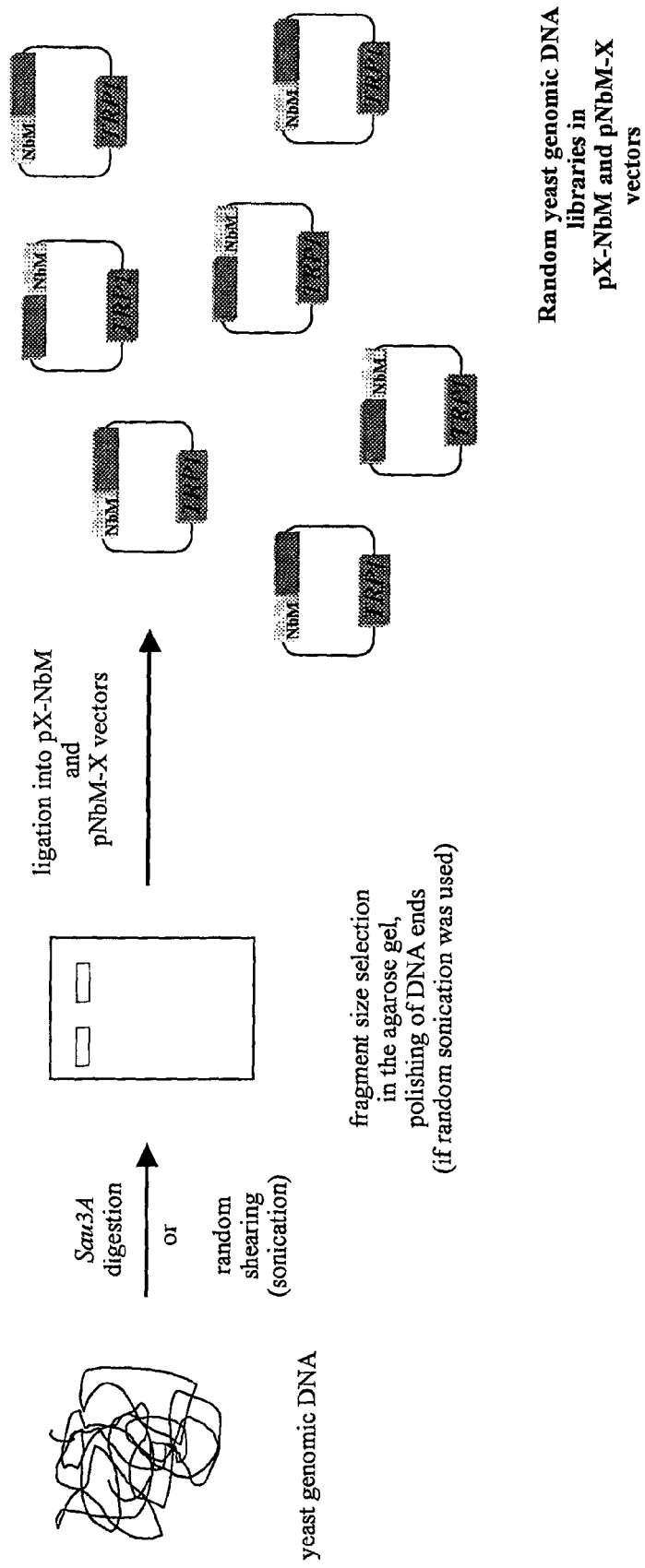

FIG. 4A. Construction of yeast genomic DNA libraries in pX-HA-NbM and pNbM-HA-X vectors. Yeast genomic DNA is isolated from the wild type yeast strain and cleaved by restriction endonuclease Sau3A, or is random sheared by sonication. DNA fragments ranging in size from 0.5-3 kb (blue boxes) are selected and cut out from the agarose gel, and ligated into pX-HA-NbM and pNbM-HA-X treated with BamHI and calf intestine alkaline phosphatase. The ligated DNA is transformed in *E. coli* and plasmid DNA is isolated and pooled together. Yeast genomic DNA library prepared in this way can than be transformed in the yeast reporter strain expressing a bait protein of interest (Y) fused to CbM-TDA portion.

Figure 4B:
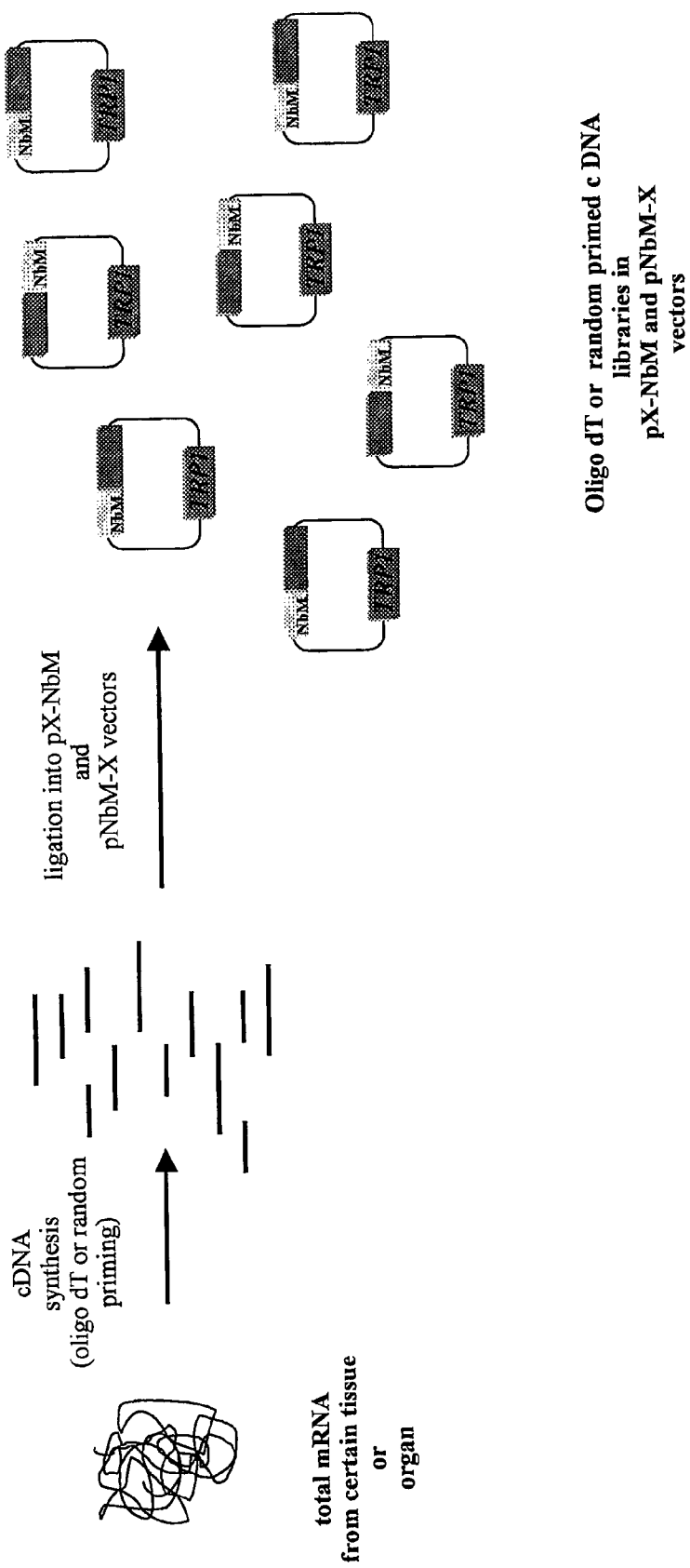

FIG. 4B. Construction of cDNA libraries in pX-HA-NbM and pNbM-HA-X vectors. Total mRNA is isolated from a certain cell line, tissue or organism, and is converted into cDNA via action of reverse transcriptase. The appropriate linkers are ligated to cDNA molecules, which are then introduced into a specific unique restriction site located in the MCS of pX-HA-NbM and pNbM-HA-X plasmids.

Figure 5:
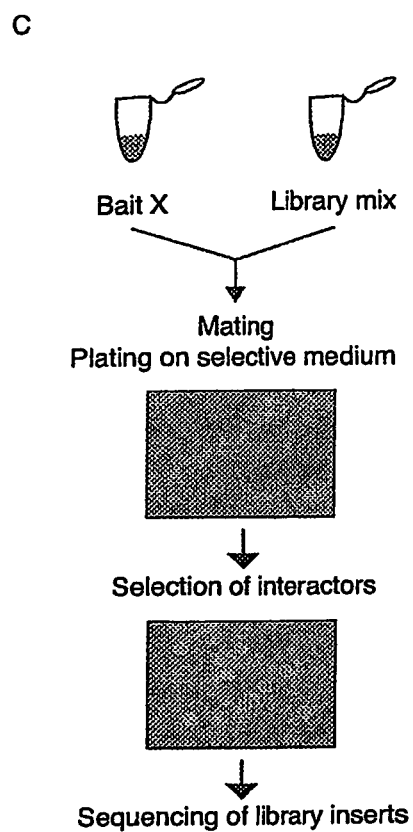

FIG. 5. Library transformation by the mating procedure. In this screening approach one CbM-TDA-fused bait X is screened against an entire library and positives are selected based on their ability to grow on selection plates. Diploids that have survived selection in the library screening are picked up and the library plasmids encoding the interacting prey are isolated and sequenced in order to identify the interacting protein. As specified in the section X, the libraries can be made either from random genomic or cDNA fragments or from full-length ORFs that are cloned separately and then pooled.

FIG. 6. Possible outcomes of the MbY2H screen. A. Bait and prey protein do not interact in yeast. In this case, no reconstitution of NbM and CbM will take place and no split-ubiquitin will be formed. Since no split-ubiquitin is formed, the transcriptional activator polypeptide will not be cleaved off by ubiquitin-specific proteases and the transcriptional activator polypeptide is unable to reach the nucleus of the yeast cell. As a consequence, the reporter genes of the yeast transformant are not activated and will not produce any reporter protein. Therefore, the respective yeast transformant will be unable to grow on the selective medium. B. Bait and prey do interact. On interaction between bait and prey proteins, ubiquitin reconstitution occurs and leads to the proteolytic cleavage and subsequent release of a transcription factor which triggers the activation of a reporter system. Consequently, the respective yeast transformant will be able to grow on the selective medium and will appear as isolated yeast colonies after 3-5 days incubation at 30° C.

Figure 7:
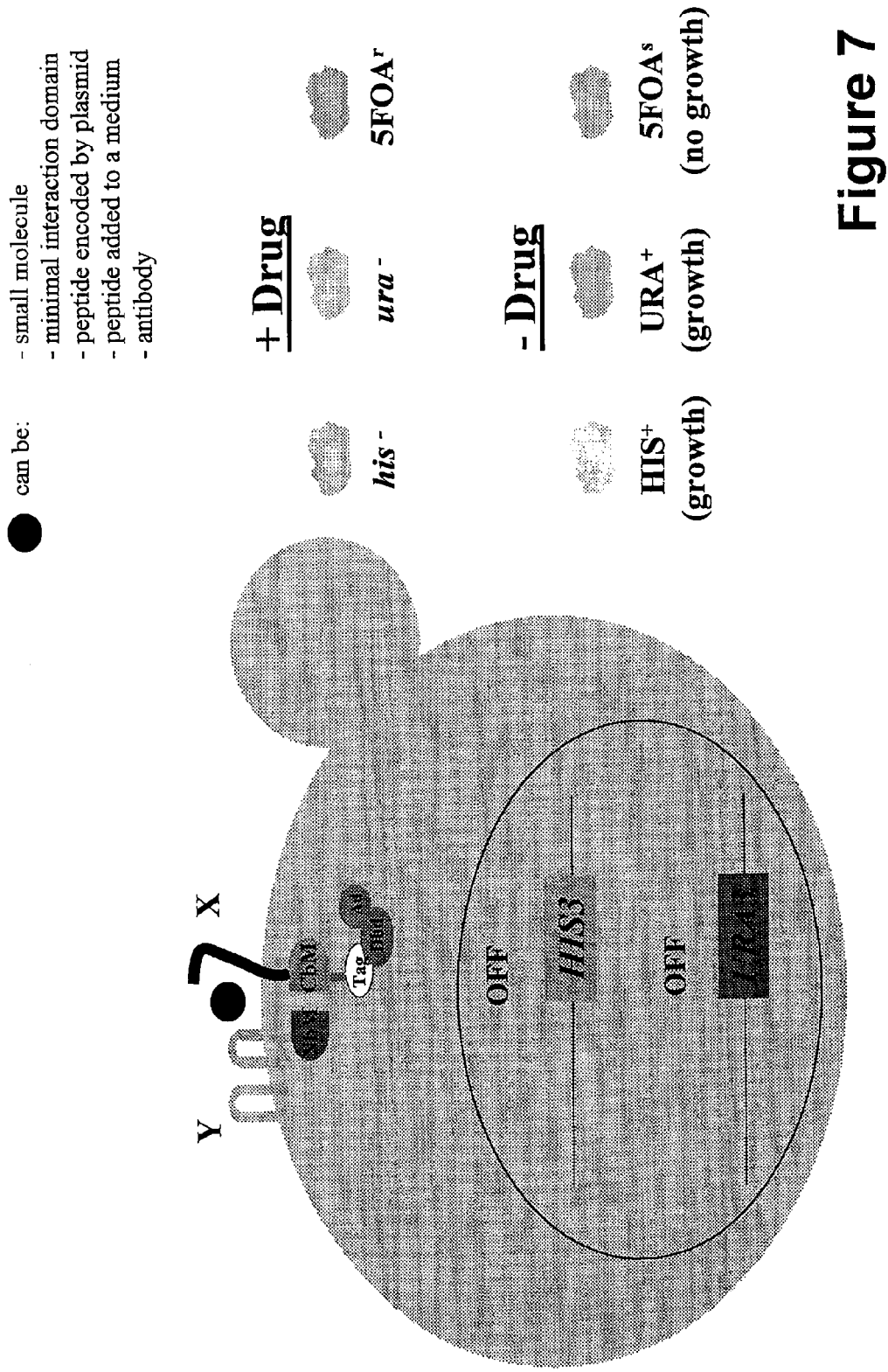

FIG. 7. General drug screening using the MbY2H technology. In this experimental design, the HIS3 reporter is used for positive selection, while URA3 is used for counterselection. Interaction between two membrane proteins X and Y results in reconstitution of quasi native ubiquitin and, consequently, in growth on medium lacking histidine, but lethality on medium containing 5-FOA, a toxic metabolite of the uracil pathway. Following the screening with (i) a complex random chemical library, (ii) peptide library encoded by a plasmid, (iii) a peptide present in medium, (iv) minimal interaction domain expressed from the plasmid in yeast, or (v) a single chain antibody selected from the pool of antibodies fused to NbM, (i-v are collectively called drugs), drugs are selected that render the yeast cells to be ura3- or 5-FOA$^R$ and his3—(e.g. they do not grow on selective medium lacking uracil, they are resistant to 5_FOA and they do not grown on selective medium lacking histidine).

Figure 8:
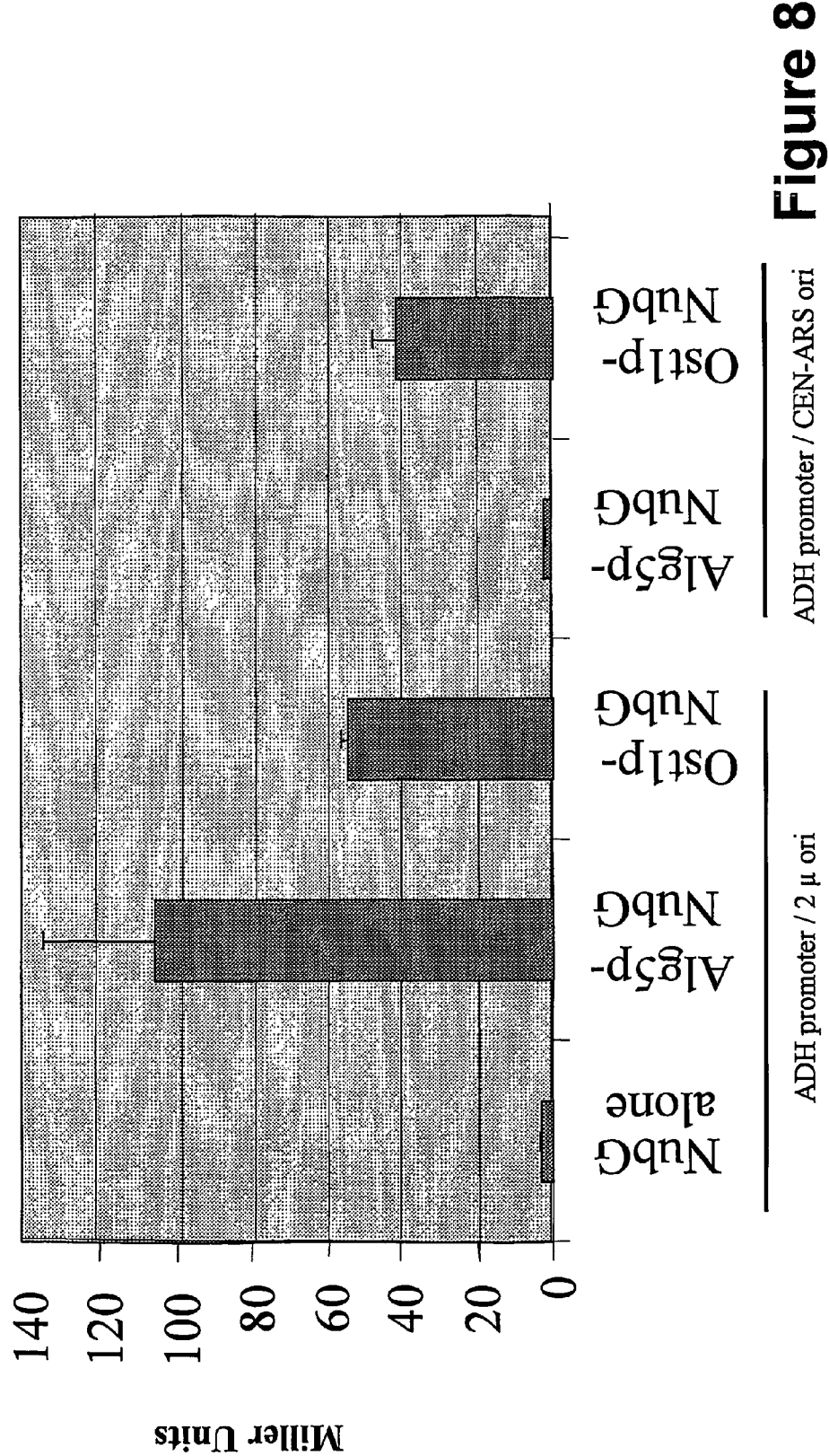

FIG. 8. Demonstration of the importance of promoter/origin of replication choice in the MbY2H system. Yeast strain YG673 (bearing the endogenously integrated yeast Wbp1-CbM-PLV bait protein) was transformed with the pAlg-5-NbMG prey plasmid under control of the strong yeast ADH promoter from either the 2µ—(high-copy) or CEN/ARS— (low copy) plasmid. In the case of ADH promoter/2µ ori combination, overexpression of the Alg5p resulted in the high expression of the HIS3 and lacZ reporter genes. However, when Alg5p was expressed under control of ADH promoter from the low copy number vector (CEN/ARS), no activation of the reporter genes was observed. As the positive control, an interacting Swp1p was used.

Figure 9:
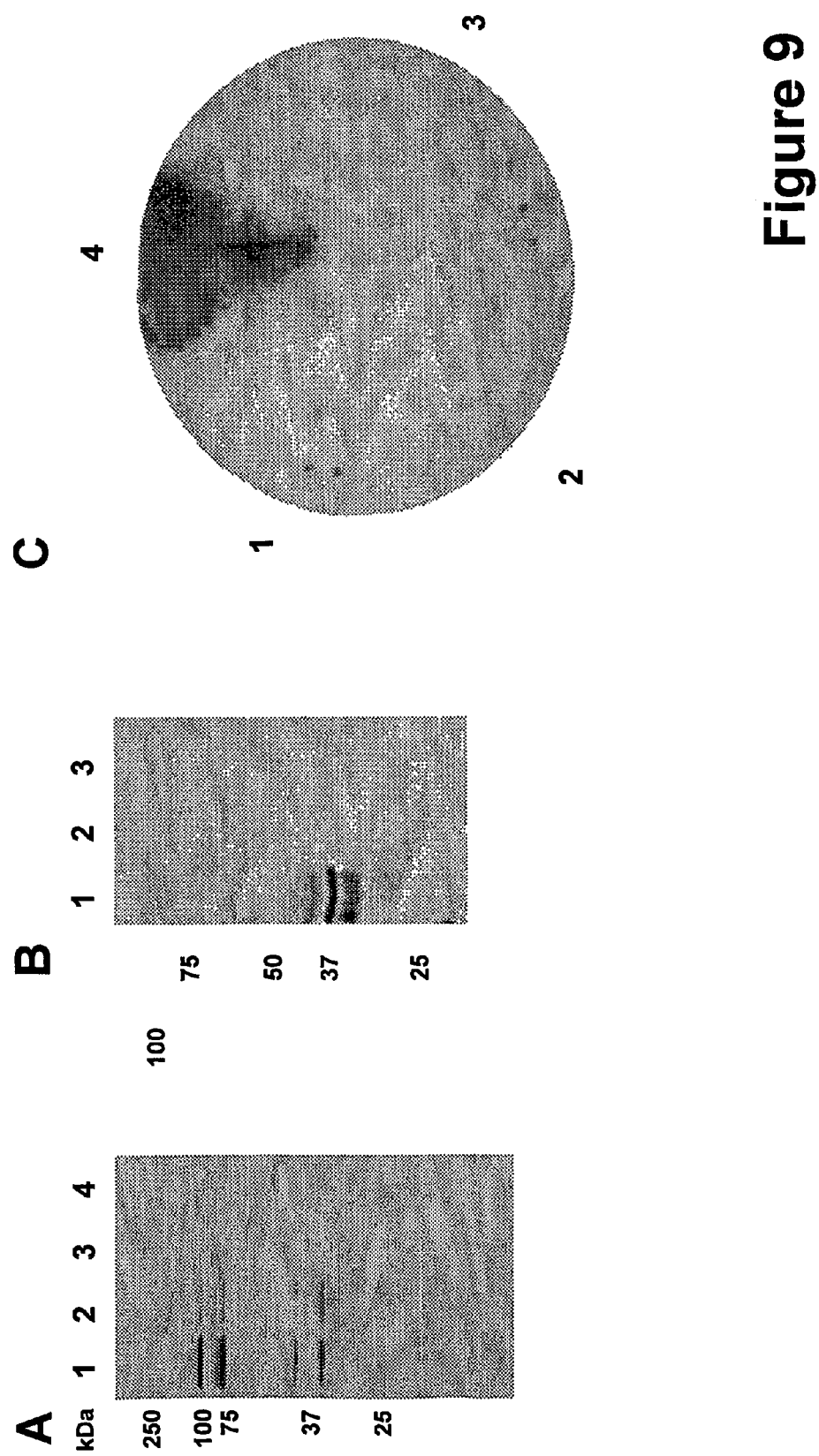

FIG. 9.: Expression of the beta2-adrenergic receptor in the yeast reporter strain L40. FIG. 9 (A): L40 was transformed with the construct construct pBAR-CbM-FLV and with an empty vector carrying the LEU2 resistance marker. Two independent transformants were selected from the transformation plates and grown in selective medium to an OD(600) of 1.0. Extracts were prepared according to standard procedures, run on 12% SDS-PAGE gels, transferred to nitrocellulose and the fusion proteins were detected using a polyclonal clones transformed with the construct pBAR-CbM-TDA show a prominent band at 100 kDa, the expected size for the beta2 AR-CbM-TDA fusion polypeptide, as well as smaller bands of 75, 40 and 35 kDa, possibly representing postranslational modification or proteolytic degradation products. Lanes 2 and 3: L40 transformed with empty control vector. No bands are detected by the VP16 antibody. (2) The beta2 AR is localized in the membrane. L40 cells transformed with pBAR-CbM-TDA were lysed and extracts were separated into soluble and particulate fractions. Lane 1: total extract. Two bands of 100 and 75 kDa, as well as lower molecular weight bands around 37 kDa are detected by the VP16 antibody. Lane 2: soluble fraction. No receptor is found in the soluble fraction. Lane 3: particulate fraction (membranes). The VP16 antibody recognizes a 100 kDa band representing the beta2 adrenergic receptor. FIG. 9(B) shows that the receptor was only found in the membrane fraction, but not in the soluble fraction. FIG. 9 (C): Self-activation test of pBAR-CbM-TDA transformed in L40. Yeast transformants were plated on selective medium lacking leucine to select for the presence of the constructs and after incubation at 30° C. for three days, a beta-galactosidase filter assay was performed. (1) Clone 1 transformed with pBAR-CbM-TDA, lane 2: clone 2 transformed with pBAR-CbM-TDA, lane 3: empty vector, lane 4: positive control. No beta-galactosidase expression is found in two independent yeast colonies transformed with pBAR-CbM-TDA, indicating that the reporter genes of L40 are not activated by the expression of beta2 AR-CbM-TDA.

Figure 10:
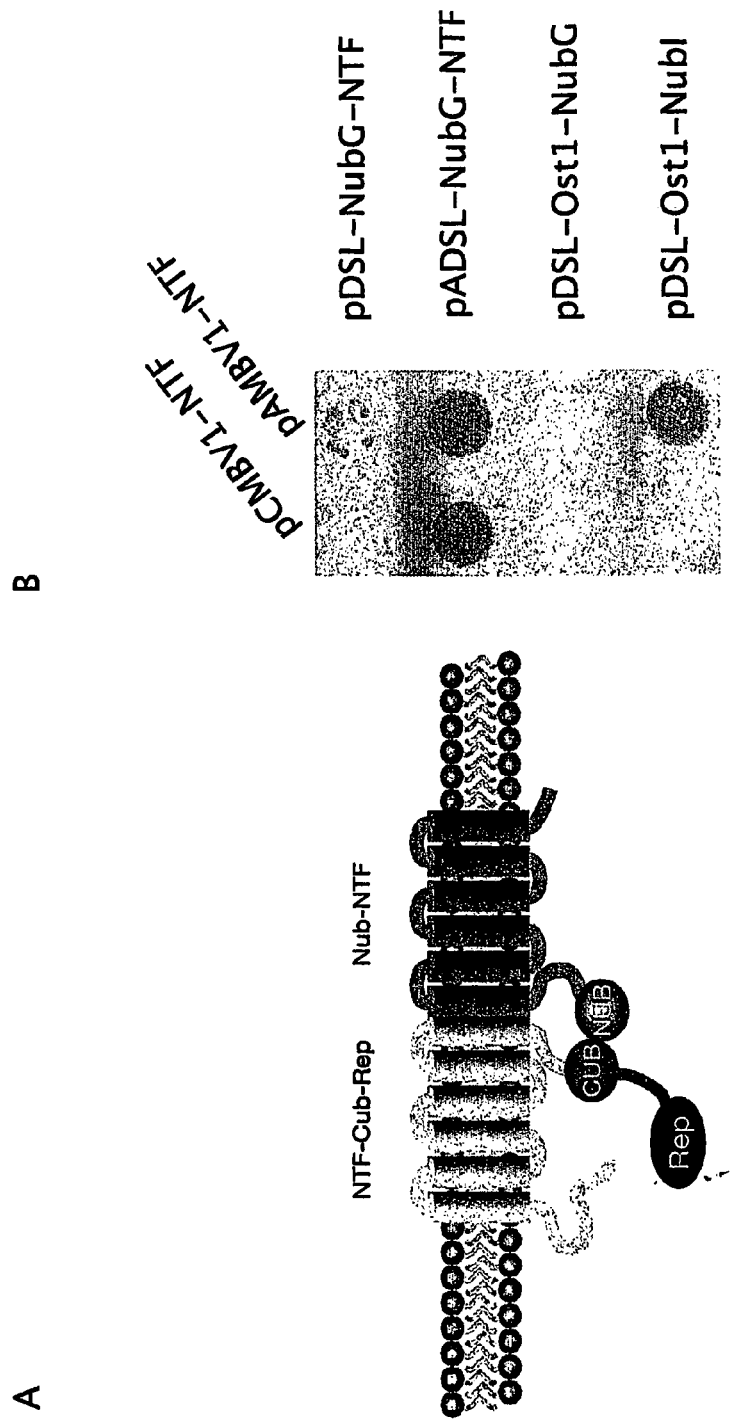

FIG. 10. Detection of protein-protein interactions in the MbY2H system requires high level expression of baits and preys. (A) Schematic representation of the NTF:NTF interaction in the MbY2H system. NTF baits are fused C-terminally to the Cub and the LexA-VP16 reporter cassette (Rep, LexA contains the R157G mutation to decrease the strength of the nuclear localization signal), whereas preys are fused N-terminally to NubG (NUB). Baits are expressed from a vector containing the CEN/ARS origin of replication, a LEU2 gene for selection in yeast and either a CYC1 promoter (low expression level, designated PCMBV1) or an ADH1 promoter (high expression level, designated pAMBV1). Preys are expressed from a vector containing a 2 micron origin of replication, a TRP1 gene for selection in yeast and either a CYC1 promoter (designated pDSL) or an ADH1 promoter (designated pADSL). (B) Homodimerization of NTF as assayed in the MbY2H system. Yeast strain L40 was transformed with the expression vectors as indicated and plated on minimal medium, selecting for cells that contained both plasmids. After 3 days growth at 30° C., 10 colonies were picked, resuspended in 0.9% NaCl and aliquots were spotted onto selective plates lacking tryptophan, leucine and histidine to select for protein-protein interactions. Weakly expressed baits (pCMBV1-NTF) and preys (pDSL-NubG-NTF) show no growth, whereas a strongly expressed bait (pAMBV1-NTF) in combination with a weakly expressed prey (pDSL-NubG-NTF) shows only partial growth on selective medium. A strongly expressed prey (pADSL-NubG-NTF) shows growth on selective medium both with a weakly and a strongly expressed bait. Neither weakly nor strongly expressed baits interact with a non-cognate control prey expressed at high levels (pDSL-Alg5-NubG). Note that only the strongly expressed bait is capable of interacting with the positive control (pDSL-Alg5-NubI). This indicates that heterologous transmembrane baits and preys have to be expressed at high levels in order to detect an interaction in the MbY2H system.

Figure 11:
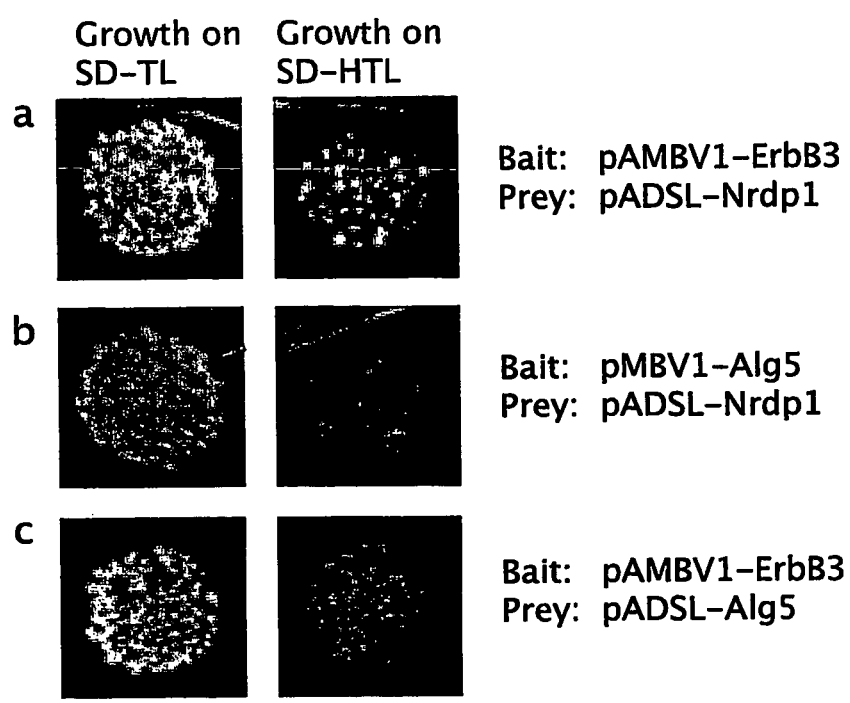

FIG. 11. Interaction between the receptor tyrosine kinase ErbB3 and the adaptor protein Nrdp1 in the MbY2H system. MbY2H baits were fused to the Cub-LexA-VP16 reporter module containing the R157G mutation to decrease the strength of the nuclear localization signal (designated LexM) and preys were fused to NubG. (a) Yeast coexxpressing pAMBV1-ErbB3 (the entire coding sequence of rat ErbB3 fused to Cub-LexM-VP16, driven by a strong ADH1 promoter from a vector containing a CEN/ARS element of replication and a LEU2 gene for selection) and pADSL-Nrdp1 (amino acids 135 to 317 of human Nrdp1 fused N-terminally to NubG, driven by a strong ADH1 promoter from a vector containing the 2 micron origin of replication and a TRP1 gene for selection) were spotted onto medium lacking tryptophan and leucine (SD-TL) to select for cells containing both bait and prey vectors and onto medium lacking tryptophan, leucine and histidine (SD-HTL) to select for the interaction between ErbB3 amd Nrdp1. Cells coexpressing ErbB3 and Nrdp1 grow on SD-HTL. (b) Yeast coexpressing the control bait pMBV1-Alg5 (the entire coding sequence of yeast Alg5 fused to Cub-LexM-VP16, driven by a CYC1 promoter from a vector containing a CEN/ARS element of replication and a LEU2 gene for selection) and pADSL-Nrdp1 were spotted onto SD-TL and SD-HTL. Cells coexpressing Alg5 and Nrdp1 do not grow on SD-HTL. The actual protein levels of yeast Alg5 expressed from the CYC1 promoter and ErbB3 expressed from the ADH1 promoter are similar. (c) Yeast coexpressing the bait pAMBV1-ErbB3 and the control prey pADSL-Alg5 were spotted onto SD-TL and SD-HTL. Cells coexpressing ErbB3 and Alg5 do not grow on SD-HTL.

Figure 12:
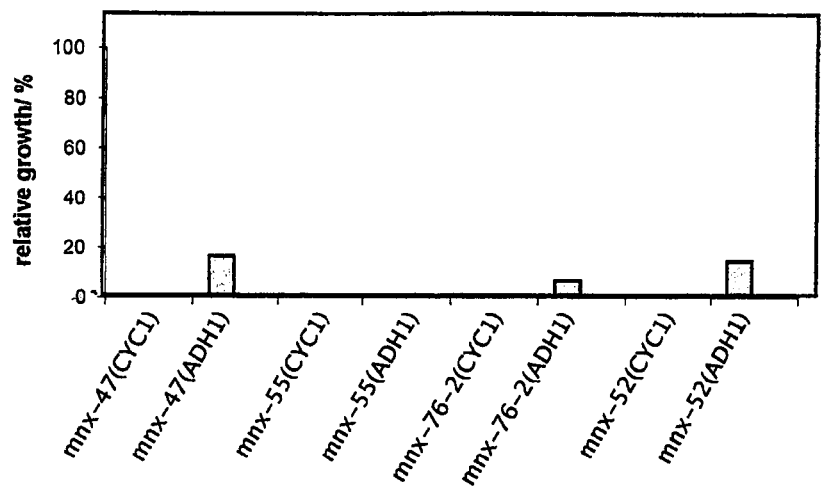
Figure 12:
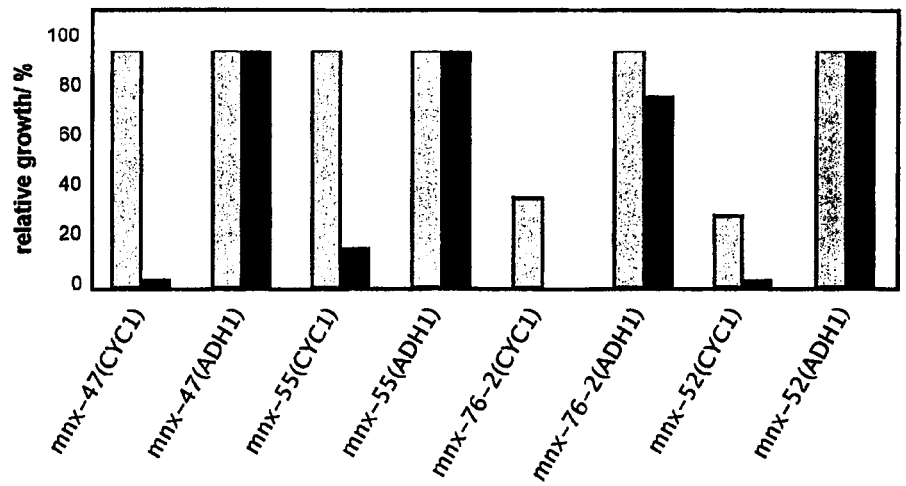

FIG. 12. Bait dependency test using the beta2-adrenergic receptor expressed at two different levels in combination with preys identified in a MbY2H screen. A bait dependency test was carried out by cotransforming the beta2-adrenergic receptor bait with several prey clones identified in the MbY2H screen described in Example 7. Bait and prey clones were cotransformed into the yeast strain and treated as described in Section 8 "Bait dependency test". (A) Beta2-adrenergic receptor expressed from the weak CYC1 promoter. Only a subset of the prey clones show growth on selective medium. (B) Beta2-adrenergic receptor expressed from the strong ADH1 promoter. All prey clones show growth on selective medium. None of the preys showed any growth when coexpressed with a Alg5 control bait expressed at high levels. Light green bars: growth on SD-HTL. Dark green bars: growth on selective medium supplemented with 5 mM aminotriazole.

Figure 13:
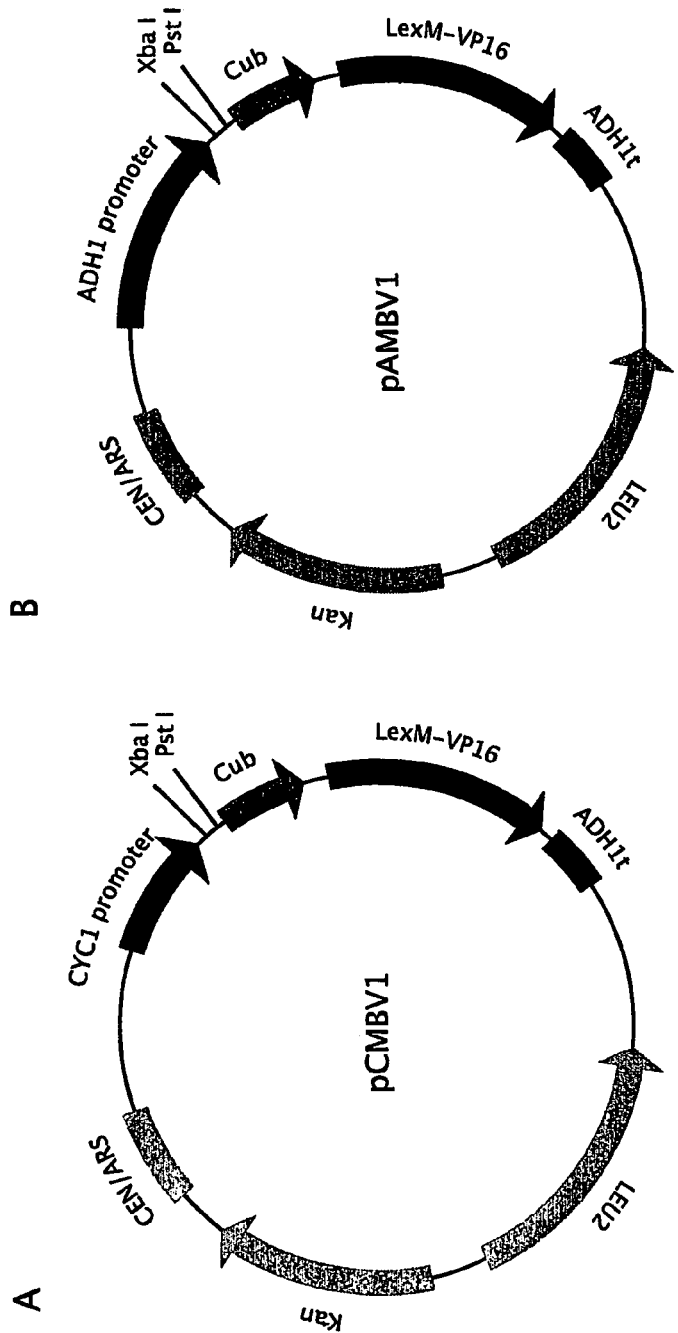

FIG. 13. Principle bait vectors of the MbY2H system. (A) In pCMBV1 expression of the bait is driven by a weak CYC1 promoter. The sites Xba I and Pst I allow subcloning of a cDNA in frame with the following Cub-LexM-VP16 cassette. Transcription is terminated by an ADH1 terminator (ADHt). The vector backbone contains a kanamycine resistance gene for propagation in E. coli (Kan), a CEN/ARS origin of replication (CEN/ARS) and a LEU2 gene for propagation in yeast (LEU2). (B) The vector pAMBV1 is identical to pCMBV1, except for the strong ADH1 promoter which drives expression of bait.

Figure 14:
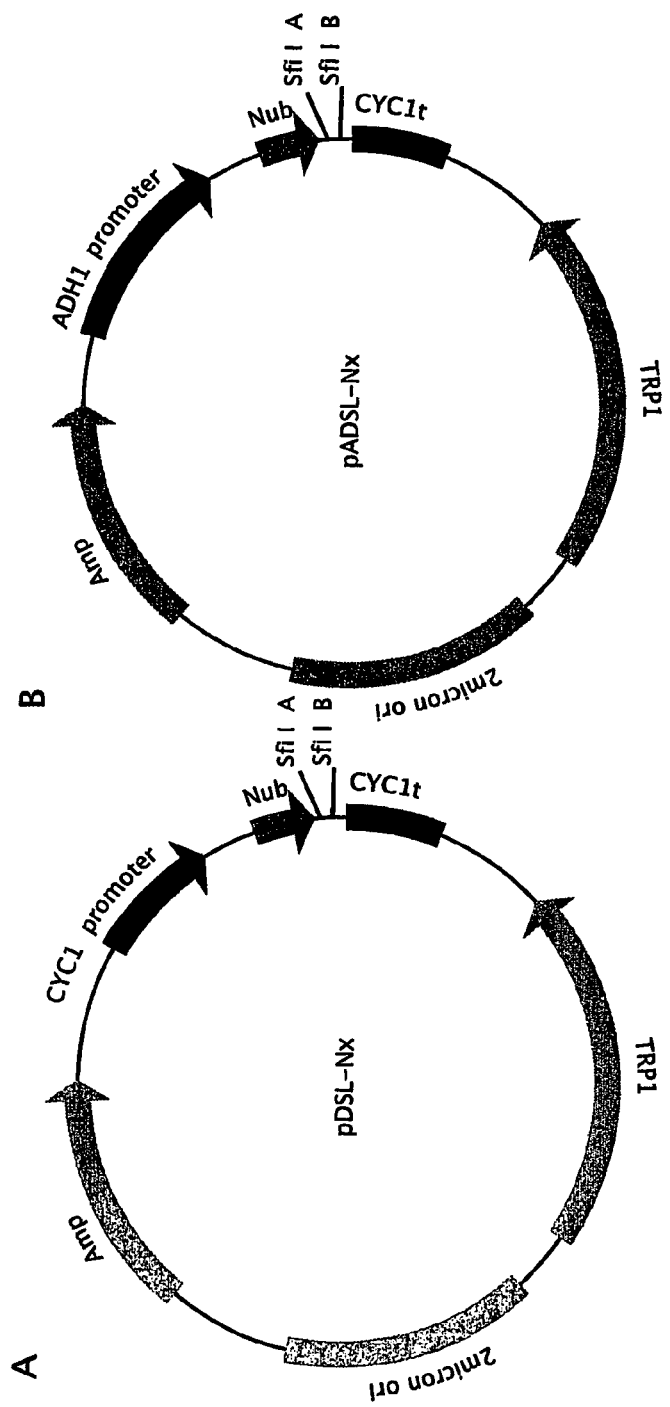
Figure 14:
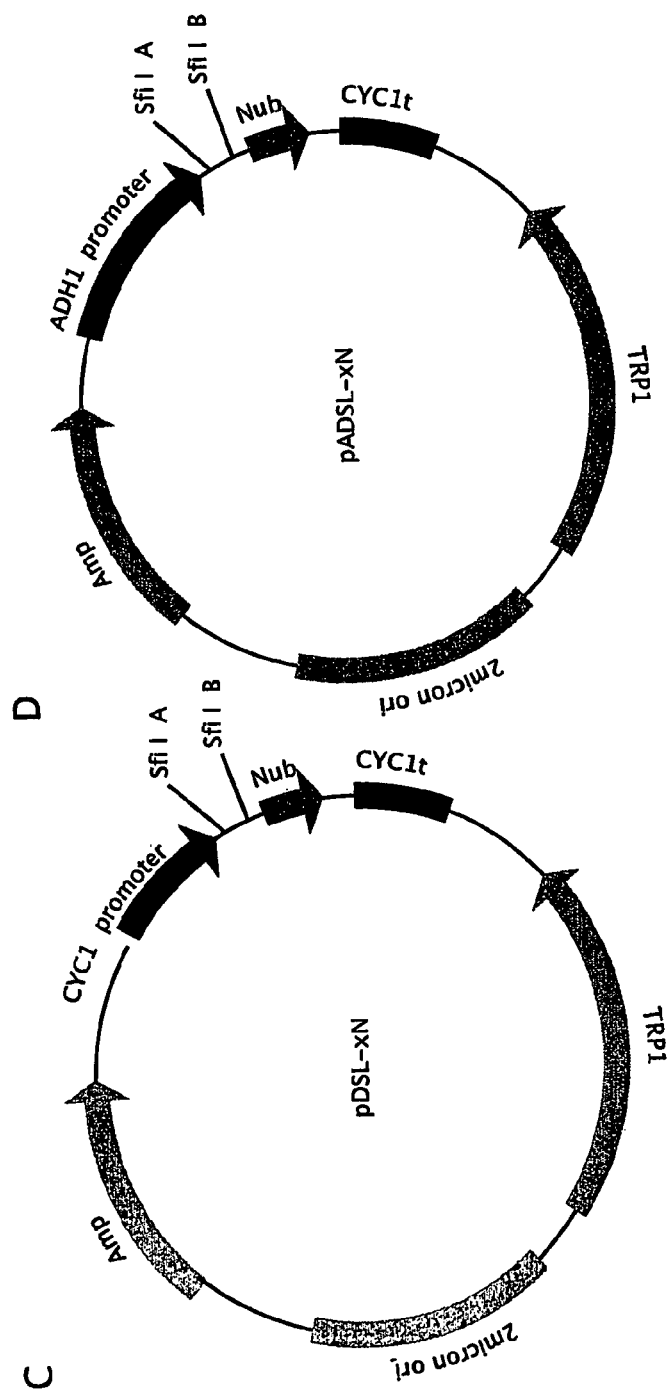

FIG. 14. Principle prey vectors of the MbY2H system. (A) In pDSL-Nx, expression of the prey is driven by a weak CYC1 promoter. Two unique Sfi I sites allow directional cloning of the prey cDNA as a C-terminal fusion to NubG. Transcription is terminated by a CYC1 terminator (CYC1t). The backbone of the vector contains an ampicillin resistance gene for propagation in E. coli (Amp), a 2 micron origin and a TRP1 gene for propagation in yeast. (B) pADSL-Nx is identical to pDSL-Nx, except for the strong ADH1 promoter driving expression of the prey. (C) pDSL-xN is identical to pDSL-Nx except that here, preys are fused N-terminally to NubG. (D) pADSL-Nx is identical to pDSL-Nx, except for the strong $ADH_1$ promoter driving expression of the prey.

The system is dependent on a number of conditions to properly carry out the method of this invention. The first interacting ("bait") protein must be an integral membrane protein, a membrane-associated protein, or it may be artificially attached to the membrane using e.g. fatty acid modification. In order to avoid false-positives, the bait protein carrying CbM-TDA may either be controlled by a promoter conferring low level expression or, if a promoter conferring high level expression is used, nucleic activity of the TDA may be controlled using other mechanisms (e.g. use of a mutated transcription factor such as a mutated LexA). We found that a soluble CbM-TDA results in gene activation without the need for any NbM. Therefore, the bait fusion protein has to be anchored to the lipid bilayer in order to test for interactions. Soluble proteins of interest might be tested by fusing them to a membrane protein anchor. In addition, the CbM-TDA and NbM domains must be located in the cytoplasm, otherwise the cleavage of the PLV portion cannot occur since UBPs are located only in the cytoplasm of the yeast cell.

Bait Vectors

Bait vectors are plasmid constructs which preferably contain the following features:

(1) A selection marker for propagation of the plasmids in E. coli, which preferably is an expression cassette encoding the kanamycine resistance gene, but which may also be an expression cassette encoding the ampicillin resistance gene or the chloramphenicol resistance gene. In fact, any other marker that is selectable in E. coli may be used for this purpose.

(2) An origin of replication that allows propagation of the plasmids in E. coli, such as a pUC based or pBR322 origin of replication, but preferably an origin of replication that allows the plasmid to be propagated in E. coli at a high copy number.

(3) A selection marker for propagation of the plasmids in S. cerevisae, which preferably is an expression cassette encoding the LEU2 gene, but which may also be any other marker that is selectable in S. cerevisae.

(4) A CEN/ARS origin of replication which allows propagation of the plasmids in S. cerevisae at a low copy number (usually 1-2 copies per cell). The use of a CEN/ARS origin of replication in the MbY2H system is one option to ensure that the bait polypeptide is expressed at a very low level. High level expression of the bait polypeptide in yeast may lead to the activation of the reporter genes (so-called self-activation, compare for instance self-activation in the yeast two-hybrid system ((Fields & Song, 1989, Golemis et al., 1999), (Serebriiskii & Golemis, 2001), Clontech MATCHMAKER System 3 User Manual).

(5) An expression cassette, preferably contains the elements as follows:

(1) A promoter that confers low level expression, such as a CYC1 promoter, or a CUP1 promoter which is inducible by the addition of copper to the medium (Angermayr et al., 2000, Macreadie et al., 1989), or confers high level expression (e.g. ADH1 or TEF1 promoter). The use of an inducible promoter has the following advantages: a) when induced, it leads to overexpression of the bait polypeptide in yeast b) when not induced, the promoter only produces a very low level of bait polypeptide, which ensures proper insertion of the bait polypeptide into the membrane of the yeast cells and prevents problems of self-activation that are connected to the overexpression of the bait polypeptide. The use of an inducible promoter represents an important advantage since it allows verification of correct expression and subsequent library screening to be carried out using the same bait construct.

(2) A nucleic acid sequence encoding a leader which may be a signal sequence derived from a yeast integral membrane protein such as STE2 (Overton & Blumer, 2000) or a signal sequence which confers fatty acid modification to the following polypeptide (N-MGCTLSAEDKPGGP-C) (SEQ ID No. 1) which is in the same reading frame as the reading frame of the signal sequence (Angermayr et al., 2000, Wolven et al., 1997).

(3) A multiple cloning site containing one or several recognition sites for restriction enzymes which allow the insertion of a nucleic acid encoding a protein or a protein fragment or a polypeptide, and sequences flanking a defined recognition site for a restriction endonuclease, preferably the restriction endonucleases Stu I or Eco47 III, which are used to insert a nucleic acid sequence encoding a protein or protein fragment or a polypeptide established in vivo recombination method as described above.

(4) A nucleic acid sequence encoding the C-terminal open reading frame of yeast ubiqutin (CbM), encompassing amino acids 35-76 (for amino acid numbering of ubiquitin and exact explanation of ubiquitin fragments, see (Johnsson & Varshavsky, 1994).

(5) The expression of the bait polypeptide can then be easily verified using standard procedures such as detection by immunoblot using a specific antibody directed against either e.g. the Gal4, LexM, B42 or VP16 moieties (see below), or preferably, against the 3xFLAG, 3xMYC or HA epitopes that are present in the bait fusion. The vector contains a nucleic acid sequence encoding an epitope tag, which can be either the 3xFLAG epitope (Chubet & Brizzard, 1996, Heman et al., 2000), the 3xMYC epitope (Evan et al., 1985), or any other sequence encoding a polypeptide that can be detected by any means, such as immunoblotting, A nucleic acid sequence encoding another epitope tag, such as the hemagglutinin epitope tag (Wilson et al., 1984), may also be present.

(6) A nucleic acid sequence encoding a polypeptide with the ability to specifically bind to a defined nucleic acid sequence, which can be the sequence encoding the bacterial LexM protein (Fogh et al., 1994), or preferably, the sequence encoding the yeast Gal4 protein (Gardner et al., 1991, Pan & Coleman, 1989), preferably the sequence encoding amino acids 1-93 of the yeast Gal4 protein, or most preferably, the sequence encoding the yeast Gal4 protein, amino acids 1-74.

(7) A nucleic acid sequence encoding a tanscriptional activator domain, such as the Herpes simplex virus protein VP16 (Shen et al., 1996, Wu et al., 1994) or more preferably, the acidic domain B42 (Hughes et al., 1996).

(8) A CYC1 or ADH1 terminator sequence.

Description of Preferred Bait Vectors:

(1) pCbM-TDA is a low copy yeast/*E. coli* shuttle vector carrying a CYC1 promoter for low level expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding the 3xFLAG epitope, followed by the sequence encoding the bacterial LexM protein, followed by the sequence encoding the Herpes simplex virus VP16 protein, followed by a CYC1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the plasmid in yeast (usually 1-2 copies per cell).

(2) pCbM-TDA is a low copy yeast/*E. coli* shuttle vector carrying a CYC1 promoter for low level expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding the 3xMYC epitope, followed by the sequence encoding the bacterial LexM protein, followed by the sequence encoding the Herpes simplex virus VP16 protein, followed by a CYC1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the plasmid in yeast (usually 1-2 copies per cell).

(3) pMP-CbM-TDA is a low copy yeast/*E. coli* shuttle vector carrying a CYC1 promoter for low level expression in yeast, followed by a nucleic acid sequence encoding the N-MGCTLSAEDKPGGP-C(SEQ ID No. 1) signal sequence for fatty acid modification, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding the 3xMYC epitope, followed by the sequence encoding the bacterial LexM protein, followed by the sequence encoding the Herpes simplex virus VP16 protein, followed by a CYC1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the plasmid in yeast (usually 1-2 copies per cell).

(4) pCUP1-CbM-TDA is a low copy yeast/*E. coli* shuttle vector carrying a CUP1 promoter for inducible expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding the 3xFLAG epitope, followed by the sequence encoding the bacterial LexM protein, followed by the sequence encoding the Herpes simplex virus VP16 protein, followed by a CYC1 terminator. The backbone of the construct contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the construct in yeast (usually 1-2 copies per cell).

(5) pMP-CbM-TDA is a low copy yeast/*E. coli* shuttle vector carrying a CYC1 promoter for low level expression in yeast, followed by a nucleic acid sequence encoding the N-MGCTLSAEDKPGGP-C (SEQ ID No. 1) signal sequence for fatty acid modification, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding the 3xMYC epitope, followed by the sequence encoding the bacterial LexM protein, followed by the sequence encoding the Herpes simplex virus VP16 protein, followed by a CYC1 terminator. The backbone of the construct contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the construct in yeast (usually 1-2 copies per cell).

(6) pCUP1-MP-CbM-TDA is a low copy yeast/*E. coli* shuttle vector carrying a CUP1 promoter for inducible expression in yeast, followed by a nucleic acid sequence encoding the N-MGCTLSAEDKPGGP-C(SEQ ID No. 1) signal sequence for fatty acid modification, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding the 3xMYC epitope, followed by the sequence encoding the bacterial LexM protein, followed by the sequence encoding the Herpes simplex virus VP16 protein, followed by a CYC1 terminator. The backbone of the construct contains the LEU2 gene for selection in yeast, the kanamycine resistance cassette for selection in *E. coli*, the CEN/ARS origin of replication for propagation in yeast and the pUC origin of replication for propagation in *E. coli*. replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the construct in yeast (usually 1-2 copies per cell).

(7) pCUP1-CbM-TDA is a low copy yeast/*E. coli* shuttle vector carrying a CUP1 promoter for inducible expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding the 3xFLAG epitope, followed by the sequence encoding the bacterial LexM protein, followed by the sequence encoding the Herpes simplex virus VP16 protein, followed by a CYC1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the plasmid in yeast (usually 1-2 copies per cell).

(8) pGA93B42 is a low copy yeast/*E. coli* shuttle vector carrying a CYC1 promoter for low level expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-93 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the plasmid in yeast (usually 1-2 copies per cell).

(9) pGA74B42 is a low copy yeast/*E. coli* shuttle vector carrying a CYC1 promoter for low level expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-74 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the plasmid in yeast (usually 1-2 copies per cell). This vector allows high stringency screens thanks to the use of a severely truncated Gal4 protein. Gal4 amino acids 1-74 retains the minimal elements necessary for recognition and binding to the GAL promoter, but it lacks the elements necessary for dimerization of the Gal4 protein. Therefore, binding of Gal4 amino acids 1-74 to the GAL1 promoter is not cooperative anymore. The non-cooperative mode of binding severely reduces the affinity of Gal4 amino acids 1-74 for the GAL1 promoter as compared to Gal4 amino acids 1-93. Consequently, higher levels of Gal4 amino acids 1-74 are needed in the nucleus to activate transcription of the reporter genes. This higher level can only be reached by an overall higher level of released Gal4 (amino acids 1-74)-B42. Only a very strong interaction between a bait protein and a prey protein is able to release the amounts of Gal4 (amino acids 1-74)-B42 needed to activate transcription of the reporter genes.

(10) pCGA93B42 is a low copy yeast/*E. coli* shuttle vector carrying a CUP1 promoter for inducible expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-93 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the plasmid in yeast (usually 1-2 copies per cell).

(11) pCGA74B42 is a low copy yeast/*E. coli* shuttle vector carrying a CUP1 promoter for inducible expression in yeast, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-93 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the plasmid in yeast (usually 1-2 copies per cell). This vector allows high stringency screens thanks to the use of a severely truncated Gal4 protein. Gal4 amino acids 1-74 retains the minimal elements necessary for recognition and binding to the GAL promoter, but it lacks the elements necessary for dimerization of tge Gal4 protein. Therefore, binding of Gal4 amino acids 1-74 to the GAL1 promoter is not cooperative anymore. The non-cooperative mode of binding severely reduces the affinity of Gal4 amino acids 1-74 for the GAL1 promoter as compared to Gal4 amino acids 1-93. Consequently, higher levels of Gal4 amino acids 1-74 are needed in the nucleus to activate transcription of the reporter genes. This higher level can only be reached by an overall higher level of released Gal4 (amino acids 1-74)-B42. Only a very strong interaction between a bait protein and a prey protein is able to release the amounts of Gal4 (amino acids 1-74)-B42 needed to activate transcription of the reporter genes.

(12) pMGA93B42 is a low copy yeast/*E. coli* shuttle vector carrying a CYC1 promoter for low level expression in yeast, followed by a nucleic acid sequence encoding the N-MGCTLSAEDKPGGP-C (SEQ ID No. 1) signal sequence for fatty acid modification, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-93 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the plasmid in yeast (usually 1-2 copies per cell).

(13) pMGA74B42 is a low copy yeast/*E. coli* shuttle vector carrying a CYC1 promoter for low level expression in yeast, followed by a nucleic acid sequence encoding the N-MGCTLSAEDKPGGP-C (SEQ ID No. 1) signal sequence for fatty acid modification, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-74 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the plasmid in yeast (usually 1-2 copies per cell). This vector allows high stringency screens thanks to the use of a severely truncated Gal4 protein. Gal4 amino acids 1-74 retains the minimal elements necessary for recognition and binding to the GAL promoter, but it lacks the elements necessary for dimerization of the Gal4 protein. Therefore, binding of Gal4 amino acids 1-74 to the GAL1 promoter is not cooperative anymore. The non-cooperative mode of binding severely reduces the affinity of Gal4 amino acids 1-74 for the GAL1 promoter as compared to Gal4 amino acids 1-93. Consequently, higher levels of Gal4 amino acids 1-74 are needed in the nucleus to activate transcription of the reporter genes. This higher level can only be reached by an overall higher level of released Gal4 (amino acids 1-74)-B42. Only a very strong interaction between a bait protein and a prey protein is able to release the amounts of Gal4 (amino acids 1-74)-B42 needed to activate transcription of the reporter genes.

(14) pCMGA93B42 is a low copy yeast/*E. coli* shuttle vector carrying a CUP1 promoter for inducible expression in yeast, followed by a nucleic acid sequence encoding the N-MGCTLSAEDKPGGP-C(SEQ ID No. 1) signal sequence for fatty acid modification, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-93 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the plasmid in yeast (usually 1-2 copies per cell).

(15) pCMGA74B42 is a low copy yeast/*E. coli* shuttle vector carrying a CUP1 promoter for inducible expression in yeast, followed by a nucleic acid sequence encoding the N-MGCTLSAEDKPGGP-C(SEQ ID No. 1) signal sequence for fatty acid modification, followed by a multiple cloning site encoding several recognition sites for restriction endonucleases, which can be used to insert a nucleic acid encoding the polypeptide of interest. The multiple cloning site is followed by a nucleic acid sequence encoding amino acids 35-76 of yeast ubiquitin (CbM), followed by a sequence encoding amino acids 1-74 of the yeast Gal4 protein, followed by the sequence encoding the acidic domain B42, followed by an ADH1 terminator. The backbone of the plasmid contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the plasmid in yeast (usually 1-2 copies per cell). This vector allows high stringency screens thanks to the use of a severely truncated Gal4 protein. Gal4 amino acids 1-74 retains the minimal elements necessary for recognition and binding to the GAL promoter, but it lacks the elements necessary for dimerization of the Gal4 protein. Therefore, binding of Gal4 amino acids 1-74 to the GAL1 promoter is not cooperative anymore. The non-cooperative mode of binding severely reduces the affinity of Gal4 amino acids 1-74 for the GAL1 promoter as compared to Gal4 amino acids 1-93. Consequently, higher levels of Gal4 amino acids 1-74 are needed in the nucleus to activate transcription of the reporter genes. This higher level can only be reached by an overall higher level of released Gal4 (amino acids 1-74)-B42. Only a very strong interaction between a bait protein and a prey protein is able to release the amounts of Gal4 (amino acids 1-74)-B42 needed to activate transcription of the reporter genes.

(16) pMP-CbM-ML-MCS is a low copy yeast/*E. coli* shuttle vector carrying a CYC1 promoter for low level expression in yeast, followed by a nucleic acid sequence encoding the N-MGCTLSAEDKPGGP-C(SEQ ID No. 1) signal sequence for fatty acid modification, followed by a nucleic acid sequence encoding amino acids 35-76 of yeast ubiquitin (CbM), followed by a sequence encoding the 3xMYC epitope, followed by the sequence encoding the bacterial LexM protein, followed by a multiple cloning site encoding several recognition sites for restriction endonucleases, which can be used to insert a nucleic acid encoding the polypeptide of interest, followed by a CYC1 terminator. The backbone of the construct contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the construct in yeast (usually 1-2 copies per cell).

(17) pCUP1-MP-CbM-ML-MCS is a low copy yeast/*E. coli* shuttle vector carrying a CUP1 promoter for inducible expression in yeast, followed by a nucleic acid sequence encoding the N-MGCTLSAEDKPGGP-C(SEQ ID No. 1) signal sequence for fatty acid modification, followed by a nucleic acid sequence encoding amino acids 35-76 of yeast ubiquitin (CbM), followed by a sequence encoding the 3xMYC epitope, followed by the sequence encoding the bacterial LexM protein, followed by a multiple cloning site encoding several recognition sites for restriction endonucleases, which can be used to insert a nucleic acid encoding the polypeptide of interest, followed by a CYC1 terminator. The backbone of the construct contains the LEU2 gene for selection in yeast, the kanamycine resistance cassette for selection in *E. coli*, the CEN/ARS origin of replication for propagation in yeast and the pUC origin of replication for propagation in *E. coli*. replication for propagation in yeast and the pUC origin of replication for propagation in *E. coli*. This vector is suitable for the inducible expression of CbM-fused polypeptides in yeast, due to the combination of an inducible CUP1 promoter and a CEN/ARS origin of replication, which results in low copy numbers of the construct in yeast (usually 1-2 copies per cell).

(18) pMGA93-MCS is a low copy yeast/*E. coli* shuttle vector carrying a CYC1 promoter for low level expression in yeast, followed by a nucleic acid sequence encoding the N-MGCTLSAEDKPGGP-C (SEQ ID No. 1) signal sequence for fatty acid modification, followed by a nucleic acid sequence encoding amino acids 35-76 of yeast ubiquitin (CbM), followed by a sequence encoding amino acids 1-93 of the yeast Gal4 protein, followed by a multiple cloning site encoding several recognition sites for restriction endonucleases, which can be used to insert a nucleic acid encoding the polypeptide of interest, followed by an ADH1 terminator. The backbone of the construct contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the construct in yeast (usually 1-2 copies per cell).

(19) pMGA74-MCS is a low copy yeast/*E. coli* shuttle vector carrying a CYC1 promoter for low level expression in yeast, followed by a nucleic acid sequence encoding the N-MGCTLSAEDKPGGP-C (SEQ ID No. 1) signal sequence for fatty acid modification, followed by a nucleic acid sequence encoding amino acids 35-76 of yeast ubiquitin (CbM), followed by a sequence encoding amino acids 1-74 of the yeast Gal4 protein, followed by a multiple cloning site encoding several recognition sites for restriction endonucleases, which can be used to insert a nucleic acid encoding the polypeptide of interest, followed by an ADH1 terminator. The backbone of the construct contains the LEU2 gene for selection in yeast, the kanamycine resistance cassette for selection in *E. coli*, the CEN/ARS origin of replication for propagation in yeast and the pUC origin of replication for propagation in *E. coli*. This vector is suitable for the low level expression of CbM-fused polypeptides in yeast, due to the combination of a weak CYC1 promoter and a CEN/ARS origin of replication, which results in low copy numbers of the construct in yeast (usually 1-2 copies per cell). This vector allows high stringency screens thanks to the use of a severely truncated Gal4 protein. Gal4 amino acids 1-74 retains the minimal elements necessary for recognition and binding to the GAL promoter, but it lacks the elements necessary for dimerization of tge Gal4 protein. Therefore, binding of Gal4 amino acids 1-74 to the GAL1 promoter is not cooperative anymore. The non-cooperative mode of binding severely reduces the affinity of Gal4 amino acids 1-74 for the GAL1 promoter as compared to Gal4 amino acids 1-93. Consequently, higher levels of Gal4 amino acids 1-74 are needed in the nucleus to activate transcription of the reporter genes. This higher level can only be reached by an overall higher level of released Gal4 (amino acids 1-74)-bait polypeptide. Only a very strong interaction between a bait protein and a prey protein is able to release the amounts of Gal4 (amino acids 1-74)-bait polypeptide needed to activate transcription of the reporter genes.

(20) pCMGA93-MCS is a low copy yeast/E. coli shuttle vector carrying a CUP1 promoter for inducible expression in yeast, followed by a nucleic acid sequence encoding the N-MGCTLSAEDKPGGP-C(SEQ ID No. 1) signal sequence for fatty acid modification, followed by a nucleic acid sequence encoding amino acids 35-76 of yeast ubiquitin (CbM), followed by a sequence encoding amino acids 1-93 of the yeast Gal4 protein, followed by a multiple cloning site encoding several recognition sites for restriction endonucleases, which can be used to insert a nucleic acid encoding the polypeptide of interest, followed by an ADH1 terminator. The backbone of the construct contains the LEU2 gene for selection in yeast, the kanamycine resistance cassette for selection in E. coli, the CEN/ARS origin of replication for propagation in yeast and the pUC origin of replication for propagation in E. coli. This vector is suitable for the inducible expression of CbM-fused polypeptides in yeast, due to the combination of an inducible CUP1 promoter and a CEN/ARS origin of replication, which results in low copy numbers of the construct in yeast (usually 1-2 copies per cell).

(21) pCMGA74-MCS is a low copy yeast/E. coli shuttle vector carrying a CUP1 promoter for inducible expression in yeast, followed by a nucleic acid sequence encoding the N-MGCTLSAEDKPGGP-C(SEQ ID No. 1) signal sequence for fatty acid modification, followed by a nucleic acid sequence encoding amino acids 35-76 of yeast ubiquitin (CbM), followed by a sequence encoding amino acids 1-74 of the yeast Gal4 protein, followed by a multiple cloning site encoding several recognition sites for restriction endonucleases, which can be used to insert a nucleic acid encoding the polypeptide of interest, followed by an ADH1 terminator. The backbone of the construct contains the LEU2 gene for selection in yeast, the kanamycine resistance cassette for selection in E. coli, the CEN/ARS origin of replication for propagation in yeast and the pUC origin of replication for propagation in E. coli. This vector is suitable for the inducible expression of CbM-fused polypeptides in yeast, due to the combination of an inducible CUP1 promoter and a CEN/ARS origin of replication, which results in low copy numbers of the construct in yeast (usually 1-2 copies per cell). This vector allows high stringency screens thanks to the use of a severely truncated Gal4 protein. Gal4 amino acids 1-74 retains the minimal elements necessary for recognition and binding to the GAL promoter, but it lacks the elements necessary for dimerization of tge Gal4 protein. Therefore, binding of Gal4 amino acids 1-74 to the GAL1 promoter is not cooperative anymore. The non-cooperative mode of binding severely reduces the affinity of Gal4 amino acids 1-74 for the GAL1 promoter as compared to Gal4 amino acids 1-93. Consequently, higher levels of Gal4 amino acids 1-74 are needed in the nucleus to activate transcription of the reporter genes. This higher level can only be reached by an overall higher level of released Gal4 (amino acids 1-74)-bait polypeptide. Only a very strong interaction between a bait protein and a prey protein is able to release the amounts of Gal4 (amino acids 1-74)-bait polypeptide needed to activate transcription of the reporter genes.

(22) pDSdual-1 is a low copy yeast/E. coli shuttle vector carrying two expression cassettes.

Cassette 1 contains a CYC1 promoter for low level expression in yeast, followed by a multiple cloning site containing multiple recognition sites for restriction endonucleases and sequences for the in vivo cloning described in section 5.2, followed by a nucleic acid sequence encoding amino acids 35-76 of yeast ubiquitin (CbM), followed by a sequence encoding amino acids 1-74 or 1-93 of the yeast Gal4 protein, followed by an ADH1 terminator.

Cassette 2 contains a CYC1 promoter for low level expression in yeast, followed by a multiple cloning site containing multiple recognition sites for restriction endonucleases and sequences for the in vivo cloning described in section 5.2, followed by the sequence encoding NbM, followed by a CYC1 terminator.

Alternatively, cassette 1 may contain a CUP1 promoter instead of a CYC1 promoter to allow the inducible expression of the bait.

Alternatively, cassette 2 may contain a CYC1 promoter for low level expression in yeast, followed by the sequence encoding NbM, followed by a multiple cloning site containing multiple recognition sites for restriction endonucleases and sequences for the in vivo cloning described in section 5.2, followed by a CYC1 terminator.

The backbone of the construct contains the LEU2 gene for selection in yeast, the kanamycine resistance cassette for selection in E. coli, the CEN/ARS origin of replication for propagation in yeast and the pUC origin of replication for propagation in E. coli.

This vector is suitable for the low level or inducible expression of a CbM-fused polypeptide together with the low level expression of a prey polypeptide fused either C- or N-terminally to NbM.

NbM Library Vectors (Prey Vectors)

NbM library vectors are plasmid constructs which preferably contain the following features:

(1) A selection marker for propagation of the plasmids in E. coli, which preferably is an expression cassette encoding the ampicillin resistance gene, but which may also be an expression cassette encoding the kanamycine resistance gene or the chloramphenicol resistance gene. In fact, any marker that is selectable in E. coli may be used for this purpose.

(2) An origin of replication that allows propagation of the plasmids in E. coli, such as a pUC based or pBR322 origin of replication, but preferably an origin of replication that allows the plasmid to be propagated in E. coli at a high copy number.

(3) A selection marker for propagation of the plasmids in S. cerevisae, which preferably is an expression cassette encoding the TRP1 gene, but which may also be any marker that is selectable in S. cerevisae.

(4) An origin of replication that allows propagation of the plasmids in S. cerevisae, such as a 2 micron based or CEN/ARS based origin of replication, but preferably an origin of replication that allows the plasmid to be propagated in S. cerevisae at a high copy number, such as the 2 micron origin of replication.

(5) An expression cassette, which preferably contains the following features:

(1) A promoter element conferring low level expression, such as CYC1, or inducible expression, such as GAL1 or CUP1, or conferring high level expression, such as ADH1 or TEF1 or promoters having a similar promoter strengh as ADH1. Promoters conferring high level expression are preferred.

(2) An open reading frame encoding the N-terminal part of yeast ubiqutin, encompassing amino acids 1-37 (for amino acid numbering of ubiquitin and exact explanation of ubiquitin fragments, see Johnsson and Varshavsky, 1994) (NbM), either wild type or bearing an amino acid exchange at either position 3 or position 13 of the published yeast ubiquitin sequence or both, where the amino acid that is used to replace the original amino acid can either be Leu, Val, Ala or Gly. Preferably, the replacement is made at position 13 with the amino acid glycine and at the positions 3 and 13 with the amino acid glycine. The NbM may also contain other mutations that are identified using an in vivo selection procedure as described below and whose aim it is to reduce or abolish the affinity of NbM for CbM.

(3) The expression of the bait polypeptide can then be easily verified using standard procedures such as detection by immunoblot using a specific antibody directed against the 3xFLAG, 3xMYC or HA epitopes that are present in the bait construct. The vector contains a nucleic acid sequence encoding an epitope tag, which can be either the 3xFLAG epitope (Chubet & Brizzard, 1996, Heman et al., 2000), the 3xMYC epitope (Evan et al., 1985), or any other sequence encoding a polypeptide that can be detected by any means, such as immunoblotting. A nucleic acid sequence encoding another epitope tag, such as the hemagglutinin epitope tag (Wilson et al., 1984), may also be used.

(4) A multiple cloning site containing one or several recognition sites for restriction enzymes which allow the insertion of nucleic acid encoding a protein or protein fragment or a polypeptide and sequences flanking a defined recognition site for a restriction endonuclease, preferably the restriction endonuclease Sma I, which are used to insert a nucleic acid sequence encoding a protein or protein fragment or a polypeptide using the in vivo recombination method described below.

(5) A terminator sequence derived from the yeast ADH1 or CYC1 genes which terminates transcription in *S. cerevisiae*.

Description of Preferred Library Vectors (1) pNbM-HA-X: High copy yeast/*E. coli* shuttle vector carrying the ADH1 promoter for high level expression in yeast, followed by the sequence encoding NbM, the sequence encoding the hemaglutinin epitope tag, a multiple cloning site and an ADH1 terminator. The backbone of the plasmid contains the TRP1 gene for selection in yeast, the ampicillin resistance cassette for selection in *E. coli*, the 2 micron origin of replication for propagation in yeast and the pUC origin of replication for propagation in *E. coli*. This vector is suitable for the high level expression of NbM-fused polypeptides in yeast, due to the combination of a strong ADH1 promoter and a 2 micron origin, which results in high copy numbers of the plasmid in yeast.

(2) pX-HA-NbM: High copy yeast/*E. coli* shuttle vector carrying the ADH1 promoter for high level expression in yeast, followed by a multiple cloning site, the sequence encoding 2 sequential hemaglutinin epitope tags, the sequence encoding NbM, and an ADH1 terminator. The backbone of the plasmid contains the TRP1 gene for selection in yeast, the ampicillin resistance cassette for selection in *E. coli*, the 2 micron origin of replication for propagation in yeast and the pUC origin of replication for propagation in *E. coli*. This vector is suitable for the high level expression of NbM-fused polypeptides in yeast, due to the combination of a strong ADH1 promoter and a 2 micron origin, which results in high copy numbers of the plasmid in yeast.

(3) p424NbM-X: High copy yeast/*E. coli* shuttle vector carrying the CYC1 promoter for low level expression in yeast, followed by the sequence encoding NbM, the sequence encoding the hemaglutinin epitope tag, a multiple cloning site and a CYC1 terminator. The backbone of the plasmid contains the TRP1 gene for selection in yeast, the ampicillin resistance cassette for selection in *E. coli*, the 2 micron origin of replication for propagation in yeast and the pUC origin of replication for propagation in *E. coli*. This vector is suitable for the low level expression of NbM-fused polypeptides in yeast, due to the combination of a very weak CYC1 promoter and a 2 micron origin, which results in high copy numbers of the plasmid in yeast.

(4) p424X-NbM: High copy yeast/*E. coli* shuttle vector carrying the CYC1 promoter for low level expression in yeast, followed by a multiple cloning site, the sequence encoding the hemaglutinin epitope tag, the sequence encoding NbM, and a CYC1 terminator. The backbone of the plasmid contains the TRP1 gene for selection in yeast, the ampicillin resistance cassette for selection in *E. coli*, the 2 micron origin of replication for propagation in yeast and the pUC origin of replication for propagation in *E. coli*. This vector is suitable for the low level expression of NbM-fused polypeptides in yeast, due to the combination of a very weak CYC1 promoter and a 2 micron origin, which results in high copy numbers of the plasmid in yeast.

(5) p414NbM-X: Low copy yeast/*E. coli* shuttle vector carrying the ADH1 promoter for high level expression in yeast, followed by the sequence encoding NbM, the sequence encoding the hemaglutinin epitope tag, a multiple cloning site and a CYC1 terminator. The backbone of the plasmid contains the TRP1 gene for selection in yeast, the ampicillin resistance cassette for selection in *E. coli*, the CEN/ARS origin of replication for propagation in yeast and the pUC origin of replication for propagation in *E. coli*. This vector is also suitable for the low level expression of NbM-fused polypeptides in yeast, due to the combination of a strong ADH1 promoter and a CEN/ARS origin, which results in very low copy numbers of the plasmid in yeast (usually 1-2 copies per cell).

(6) p414X-NbM: Low copy yeast/*E. coli* shuttle vector carrying the ADH1 promoter for high level expression in yeast, followed by a multiple cloning site, the sequence encoding two sequential hemaglutinin epitope tags, the sequence encoding NbM, and a CYC1 terminator. The backbone of the plasmid contains the TRP1 gene for selection in yeast, the ampicillin resistance cassette for selection in *E. coli*, the CEN/ARS origin of replication for propagation in yeast and the pUC origin of replication for propagation in *E. coli*. This vector is also suitable for the low level expression of NbM-fused polypeptides in yeast, due to the combination of a strong ADH1 promoter and a CEN/ARS origin, which results in very low copy numbers of the plasmid in yeast (usually 1-2 copies per cell).

Library Construction

Libraries can be constructed from nucleic acids such as genomic DNA, random or non-random oligonucleotides or cDNAs.

(1) Genomic libraries. Construction of random fragments of genomic DNA is a standard procedure and is described for example in (James et al., 1996). Briefly, genomic DNA is isolated from an organism of interest and is sheared into fragments of random size either by sonication or by other methods, such as digestion with appropriate restriction enzymes or shearing by extrusion through a syringe. Sheared fragments of the appropriate size are selected and the ends are repaired using standard procedures, such as Klenow/T4 DNA polymerase reactions or Mung Bean exonuclease reactions. Following this, the repaired fragments are cloned into a NbM-based library vector using standard procedures such as described in (Bedbrook & Ausubel, 1976, Sambrook & Russell, 2001).

(2) cDNA libraries are made using standard procedures, as described in (Gubler, 1988), or can be made using various commercially available kits, such as those marketed by Clontech, Invitrogen, or Promega. In a preferred application double-stranded cDNA fragments resulting from the use of the kit are directly inserted into an appropriate NbM library vector by means of in vivo recombination in yeast, as described by (Fusco et al., 1999, Prado & Aguilera, 1994). Nucleic acid sequences that are complementary to sequences in the expression cassette of the NbM vector are added to each end of the cDNA fragments, as described in the user manual of the MATCHMAKER System 3 Library Construction Kit (Clontech, Palo Alto, Calif., USA). Simultaneous introduction of cDNA fragments and the NbM library vector in appropriate amounts using a standard transformation procedure, as described for example (Gietz & Woods, 2001), results in homologous recombination between identical sequences at the ends of the cDNA fragments and results in the generation of NbM library vectors each containing a particular cDNA insert. Yeast transformants resulting from this procedure are collected using a standard procedure, such as described in the MATCHMAKER System 3 User Manual or the MATCHMAKER System 3 Library Construction Kit (Clontech) and can be stored at −80° C. for later screening by mating. In a different procedure, the cDNA fragments and the NbM library vector are cotransformed not in an untransformed yeast strain but into a yeast strain which has already been transformed with a plasmid encoding the bait to be used in a library screening. Following the identical transformation procedure as described previously, the yeast transformants are directly plated on selective medium and a screen is carried out as described in detail below.

(3) Random or non-random oligonucleotide libraries. Random or non-random oligonucleotides are synthesized according to standard procedures. They can be inserted into the NbM library vector using either one or several restriction endonucleases or by the in vivo cloning method described above.

Library Screening Procedure

The polypeptide to be used as bait may be inserted into both a bait vector conferring low level expression, and a bait vector conferring high level expression, these vectors being used in a parallel procedure. In order to avoid false-positives, if a promoter conferring high level expression is used for the bait protein carrying CbM-TDA, the nucleic activity of the TDA may be controlled using other mechanisms (e.g. use of a mutated transcription factor such as a mutated LexA). The prey vector preferably carries a strong promoter, such as ADH1 or TEF1.

1. Definition of Appropriate Baits

In principle, any polypeptide that can be immobilized at a membrane within the yeast cell, such as the membranes of the endoplasmatic reticulum, the golgi apparatus, the outer or inner mitochondrial membrane or, most preferably, the plasma membrane, is suitable as a bait in the MbY2H system. Polypeptides that are to be used as baits can be integral membrane proteins, or they can be soluble proteins that are attached to a membrane via fusion to a signal sequence which encodes a membrane anchor, such as a signal sequence followed by a transmembrane domain, or a signal sequence for any fatty acid modification, such as myristoylation, palmytoylation, or farnesylation. The different types of polypeptides to be used as baits are described in detail below.

2. Bait Construction

The nucleic acid sequence encoding the polypeptide to be used as bait can be inserted into one of the bait vectors described above using standard molecular biology techniques. These techniques are described in detail in (Bedbrook & Ausubel, 1976, Sambrook & Russell, 2001). However, the preferable method of inserting the nucleic acid sequence into a bait vector is by in vivo recombination in yeast (Oldenburg et al., 1997, Prado & Aguilera, 1994). The nucleic acid sequence encoding the polypeptide of interest is amplified from an appropriate template (such as genomic DNA, cDNA or preferably, plasmid DNA) using the polymerase chain reaction (PCR, (Mullis, 1990)). Primers are designed to contain a sequence that is complementary to the extreme 5' and 3' ends of the nucleic acid sequence of interest. Furthermore, each primer contains an additional 26 nucleotides of sequence at the 5' end which is identical to the 26 nucleotides of sequence on each side of a recognition site of a restriction endonuclease in one of the bait vectors described above. Thus, the PCR product contains the entire nucleic acid fragment encoding the polypeptide to be used as bait, as well as 26 nucleotides of complementary sequence (designated the "flaps") at the 5' and 3' end. The bait vector is treated by incubation with the appropriate restriction endonuclease as described in standard protocols (Bedbrook & Ausubel, 1976, Sambrook & Russell, 2001). The PCR fragment and the restricted bait vector are mixed in equimolar amounts and transformed into an appropriate yeast reporter strain using standard yeast transformation techniques (Gietz & Woods, 2001). Thanks to its endogenous repair machinery (Friedberg, 1991a, Friedberg, 1991b), each end of the PCR fragment is recombined with its homologous counterpart in the bait vector, resulting in a nucleic acid construct, where the PCR product is inserted exactly at the open ends of the bait vector (Figure ???). Because this process is absolutely specific in yeast, the PCR fragment is inserted in a defined orientation and no nucleotides at the end are either omitted or added. For this reason, insertion of a nucleic acid sequence encoding a bait polypeptide via this method is simpler and faster than the conventional insertion methods mentioned above. The insertion of the nucleic acid encoding the bait polypeptide must be made in a way so that the reading frame of the bait polypeptide is the same as that of the reporter cassette following the multiple cloning site. In this way, translation of the bait plasmid in yeast provides a continuous polypeptide that consists of the bait polypeptide fused to CbM and the elements described above.

3. Bait Verification

Prior to screening, it is necessary to test whether the bait is expressed correctly in yeast. Correct expression means that the bait polypeptide is translated in its full length in yeast, that no significant proteolysis occurs and that the bait is inserted into the membranes in yeast. First, the bait construct is transformed into an appropriate yeast strain, which can be any yeast strain, but which preferably is one of the strains described above and most preferably, one of the yeast strains DSY1 or DSY2. The yeast transformant is grown under appropriate selective conditions and expression of the bait is detected using the immunoblotting technique.

The detection of polypeptides expressed in yeast by the immunoblotting technique is standard and is described for example in (Bedbrook & Ausubel, 1976, Sambrook & Russell, 2001) and in the YEAST PROTOCOLS HANDBOOK (Clontech). The appearance of a signal of the expected molecular weight on the autoradiograph signifies that the bait polypeptide is expressed in yeast and that it is not significantly degraded by endogenous proteases.

Testing whether the bait polypeptide is inserted into the membranes in yeast is a crucial step since it guarantees that the bait is immobilized at the membrane and cannot diffuse into the nucleus. The immobilization of the bait at the membrane is an absolute prerequisite for a MbY2h screen. First, the bait construct is transformed into an appropriate yeast strain, which can be any yeast strain, but which preferably is one of the strains described above and most preferably, either of the yeast strains DSY1 or DSY2. The yeast transformant is grown under appropriate selective conditions and the insertion of the bait into the membrane is verified by detecting its presence in the particulate fraction following lysis of the yeast transformants and separation of extracts into soluble and particulate fractions, as described for example in (Fuentes et al., 2000). The appearance of a signal of the expected molecular weight in the particulate fraction, but not in the soluble fraction, on the autoradiograph signifies that the bait polypeptide is expressed and inserted into the membranes in yeast.

A second method to verify the insertion of the bait polypeptide into the yeast membrane is to carry out immunofluorescence on the yeast transformants. First, the bait construct is transformed into an appropriate yeast strain, which can be any yeast strain, but which preferably is one of the strains described above, and most preferably, either of the yeast strains DSY1 or DSY2. The yeast transformant is grown under appropriate selective conditions and processed for immunofluorescence using any of the standard methods available, as described for instance in (Burke et al., 2000). Following the immunofluorescent staining, the cells are observed under a fluorescence microscope. The presence of a fluorescent signal at the membranes of yeast signifies that the bait polypeptide is expressed and inserted into the membranes in yeast.

4. Self-Activation Test

A self-activation test is carried out to ensure that the bait polypeptide, when expressed in the absence of any prey polypeptide, does not activate the reporter genes present in the reporter strain. First, the bait construct is transformed into an appropriate yeast strain, which can be any yeast strain, but which preferably is either of the strains described above and most preferably, one of the yeast strains DSY1 or DSY2. The yeast transformant is plated on different selective media to assess the activation of all reporter genes present in the reporter strain. For example, when using the reporter strain AH109, yeast transformants carrying a bait construct and a control construct to supply the TRP1 gene are plated on selective plates lacking leucine (to select for the presence of the bait construct), tryptophan (to select for the presence of the control construct) and adenine (to assess the activity of the ADE2). Growth of yeast transformants on the selective plates signifies that the bait polypeptide alone is able to activate the reporter genes. Such a bait cannot be used for a MbY2H screen.

5. Conventional Library Transformation

In the conventional screening technique, the yeast reporter strain is first transformed with the bait plasmid as described above (resulting in a yeast strain carrying multiple copies of the bait plasmid, designated the "bait-bearing strain"). The yeast strain may be any S. cerevisiae strain bearing appropriate reporter constructs, either as autonomously replicating plasmids or as nucleic acid fragments that are integrated into the genome, but preferably, it is the yeast strain L40 [Vojtek, 1993 #398] or the yeast strain AH109 (Clontech) or the yeast strain PJ69-4A (James et al., 1996) or most preferably, it is either the yeast strains DSY1 or DSY2. The bait-bearing strain is subsequently transformed with a library of NbM-fused nucleic acids, which can be either genomic fragments, random or non-random oligonucleotides or preferably, cDNA fragments. Such a library may be constructed in any of the NbM library vectors described above, using any of the methods described herein.

6. Library Transformation by the Mating Procedure

Figure 1:
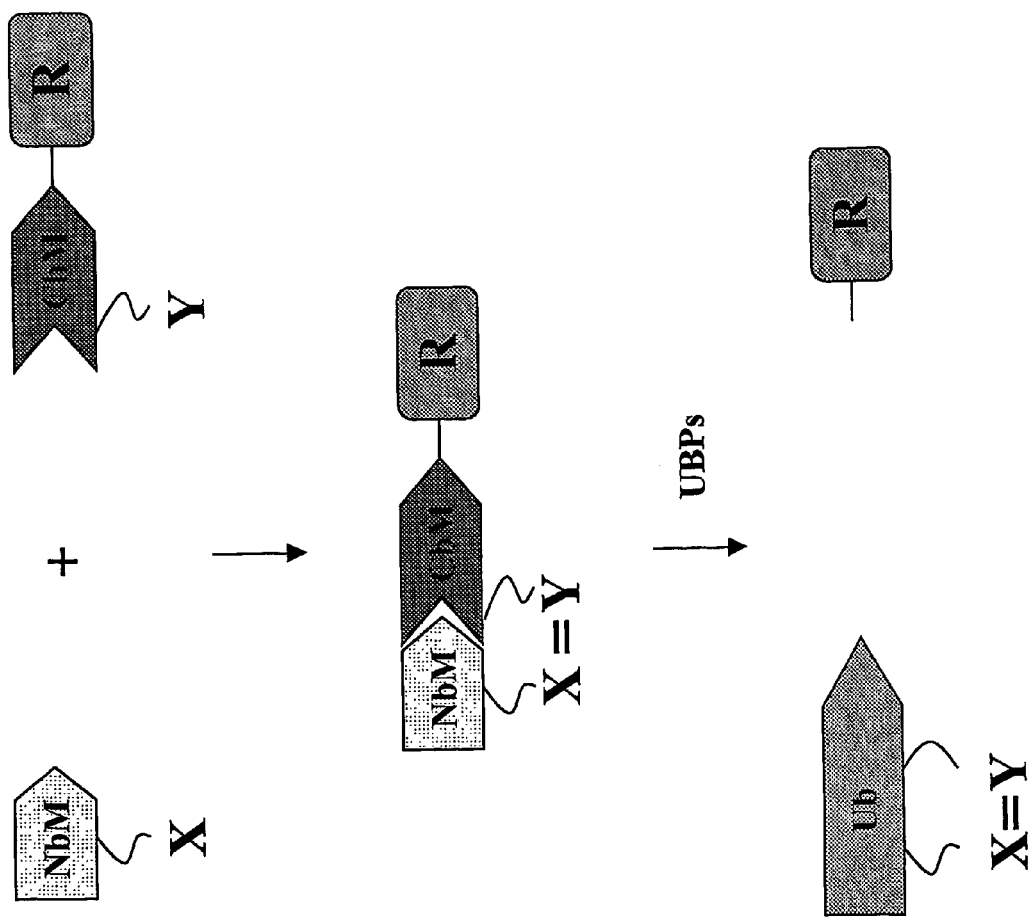
FIG. 1 shows the split-ubiquitin system for the in vivo analysis of protein interactions.
Figure 2:
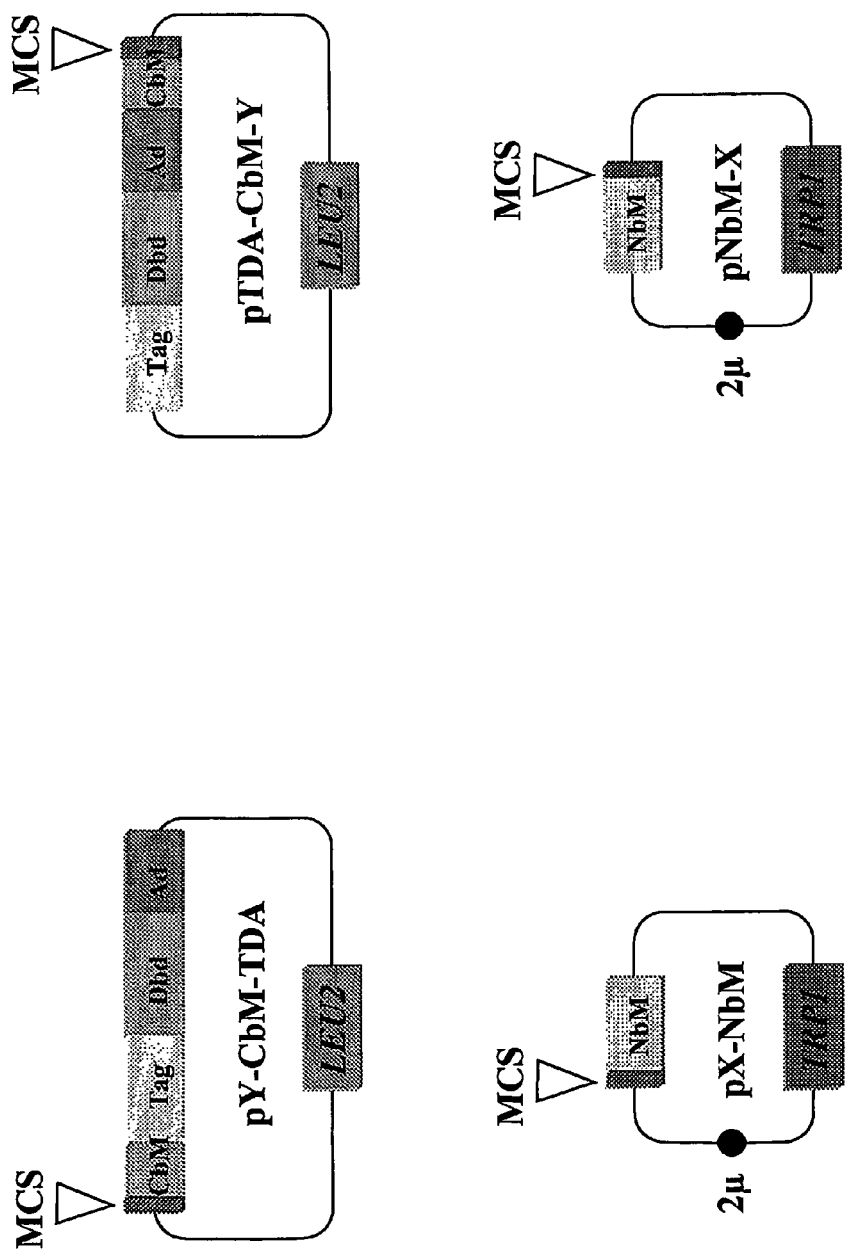
FIG. 2 shows vectors for the membrane based detection system including the bait vector and prey vector and optionally a plasmid library.

Using the mating procedure, the bait plasmid is introduced into a yeast reporter strain of a defined mating type (either a or alpha) using any of the methods described above. Then, a library, which can be any library described above, is introduced into a strain of the opposite mating type (either alpha or a) using any of the methods described above. Subsequently, the bait-bearing and library-bearing strains are mated according to standard methods (FIG. 2; (Soellick & Uhrig, 2001), MATCHMAKER System 3 User Manual, Clontech). Yeast strains used for the transformation of the bait are L40, AH109, PJ69-4A or preferably, DSY1 or DSY2. Yeast strains used to transform the library are L40alpha, Y187, PJ69-4alpha or preferably, DSYM.

7. Screening Procedure

Following transformation or mating, the yeast transformants are plated on solid selection medium. This selection medium is composed in a way as to select for the presence of (1) the bait plasmid, (2) the library plasmid and (3) any potential interaction occurring between the bait and prey polypeptides.

The type and formulation of the selection medium to be used depends on the reporter strain that is used.

When using L40 (see below), selective medium lacking (to select for the presence of the bait plasmid), tryptophan (to select for the presence of the prey plasmid), and histidine (to select for the occurrence of a protein-protein interaction) is used.

When using AH109 (see below), selective medium lacking the amino acids leucine (to select for the presence of the bait plasmid), tryptophan (to select for the presence of the prey plasmid), and histidine and adenine (to select for the occurrence of a protein-protein interaction) is used. As described herein, it is possible to modulate the stringency of the screen using the following modifications in the selective medium: (1) low stringency: selective medium lacking the amino acids leucine, tryptophan and histidine. (2) medium stringency: selective medium lacking the amino acids leucine, tryptophan and adenine. (3) high stringency: selective medium lacking the amino acids leucine, tryptophan, histidine and adenine.

When using PJ694A (see below), selective medium lacking leucine (to select for the presence of the bait plasmid), tryptophan (to select for the presence of the prey plasmid), and histidine and adenine (to select for the occurrence of a protein-protein interaction) is used. As described herein, it is possible to modulate the stringency of the screen using the following modifications in the selective medium: (1) low stringency: selective medium lacking leucine, tryptophan and histidine. (2) medium stringency: selective medium lacking the amino acids leucine, tryptophan and adenine. (3) high stringency: selective medium lacking leucine, tryptophan, histidine and adenine.

When using DSY1 (see below), selective medium lacking leucine (to select for the presence of the bait plasmid), tryptophan (to select for the presence of the prey plasmid), histidine and adenine (to select for the occurrence of a protein-protein interaction) and containing the compound 5'-fluoroorotic acid (5-FOA, to counterselect for unspecific protein-protein interactions) is used. As described herein, it is possible to modulate the stringency of the screen using the following modifications in the selective medium: (1) low stringency: selective medium lacking leucine, tryptophan and histidine and containing the compound 5-FOA. (2) medium stringency: selective medium lacking, tryptophan and adenine and containing the compound 5-FOA. (3) high stringency: selective medium lacking leucine, tryptophan, histidine and adenine and containing the compound 5-FOA.

When using DSY2 (see below), selective medium lacking leucine (to select for the presence of the bait plasmid), tryptophan (to select for the presence of the prey plasmid), and histidine and adenine (to select for the occurrence of a protein-protein interaction) is used. As described herein, it is possible to modulate the stringency of the screen using the following modifications in the selective medium: (1) low stringency: selective medium lacking leucine, tryptophan and histidine. (2) medium stringency: selective medium lacking, tryptophan and adenine. (3) high stringency: selective medium lacking leucine, tryptophan, histidine and adenine.

Using any of the strains mentioned above, an independent test for the protein-protein interaction taking place in the particular yeast transformant can be made by assaying the activity of the lacZ reporter. Each of the strains described above carries one or several copies of a lacZ reporter gene integrated into its genome. The lacZ reporter is activated in the same fashion as the other reporters and, when activated, leads to the transcription and translation of the beta-galactosidase polypeptide from *E. coli*. The presence of Beta-galactosidase can be verified by its ability to convert various substrates into colored compounds. The assays used to detect beta-galactosidase have been described numerous times ((Golemis et al., 1999), MATCHMAKER System 3 User Manual, Clontech). Any method to detect beta-galactosidase is suitable for use in the MbY2H system.

Figure 6A:
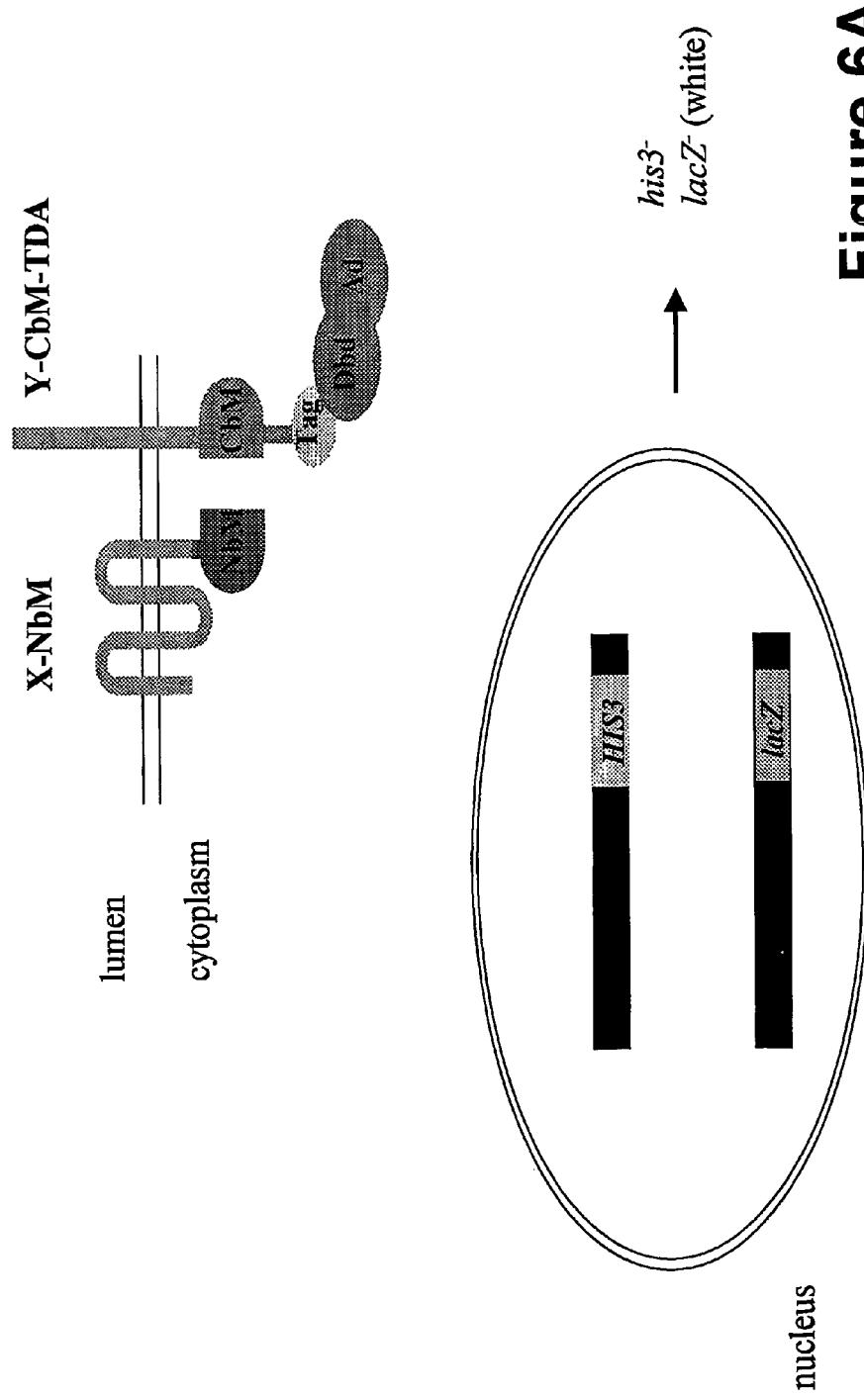

For each yeast transformant that was initially plated on the selection medium, two different outcomes are possible:

(1) The bait and prey polypeptides encoded by the bait and library plasmid, respectively, do not interact in yeast. In this case, the bait and prey polypeptides will not be spatially close, no reconstitution of NbM and CbM will take place and no split-ubiquitin will be formed. Since no split-ubiquitin is formed, the transcriptional activator polypeptide will not be cleaved off by ubiquitin-specific proteases and the transcriptional activator polypeptide is unable to reach the nucleus of the yeast cell. As a consequence, the reporter genes of the yeast transformant are not activated and will not produce any reporter protein (FIG. 6A). Therefore, the respective yeast transformant will be unable to grow on the selective medium.

Figure 6B:
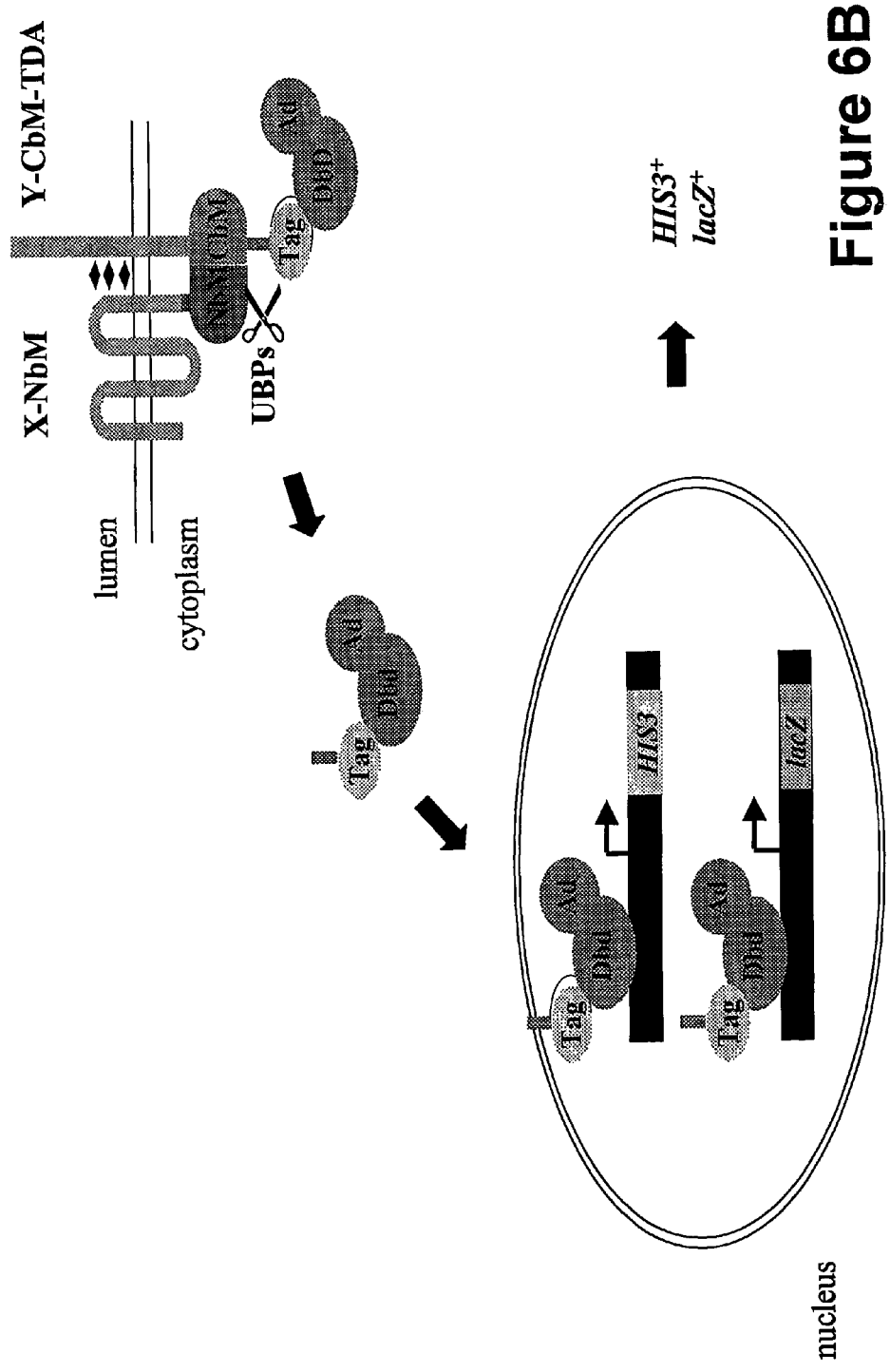

(2) The bait and prey polypeptides encoded by the bait and library plasmid, respectively, do interact in yeast. In this case, the bait and prey polypeptides will be spatially close, reconstitution of NbM and CbM will take place and split-ubiquitin will be formed. Since split-ubiquitin is formed, the transcriptional activator polypeptide will be cleaved off by ubiquitin-specific proteases and the transcriptional activator polypeptide will diffuse to the nucleus of the yeast cell. As a consequence, the reporter gene(s) of the yeast transformant is (are) activated and will produce the reporter protein(s) (FIG. 6B). Therefore, the respective yeast transformant will be able to grow on the selective medium and will appear as isolated yeast colonies after 3-5 days incubation at 30° C.

A third outcome is possible when using either of the strains DSY1 or DSY2: The bait and prey polypeptides encoded by the bait and library plasmid, respectively, do interact in yeast, but the prey polypeptide also interacts with a control bait polypeptide that is transcribed as a CbM-LexM-B42 fusion from a nucleic acid sequence integrated into the genome of the yeast reporter strain. In this case, the control bait and prey polypeptides will be spatially close, reconstitution of NbM and CbM will take place and split-ubiquitin will be formed. Since split-ubiquitin is formed, the LexM-B42 polypeptide will be cleaved off by ubiquitin-specific proteases and will diffuse to the nucleus of the yeast cell. As a consequence, the URA3 or FAR1 reporter genes of the yeast transformant are activated and will produce the Ura3 or Far1 protein, respectively. Ura3 protein converts the compound 5-FOA into a metabolite that is toxic to the yeast cell, whereas Far1 protein interferes directly with the cell cycle machinery and arrests the yeast transformant. In both cases, the particular yeast transformant will be unable to grow on selective medium.

8. Bait Dependency Test

Yeast transformants that have survived the selection procedures described in section 7 most likely carry a library construct encoding a polypeptide that is able to interact with the bait polypeptide in the yeast reporter strain. However, as with any in vivo system, there is a remote chance of isolating so-called "false positives" which are library constructs encoding particular prey polypeptides that confer upon the yeast transformant the ability to survive the selection procedures described in section 7, but that nevertheless do not interact with the bait polypeptide. A so-called bait dependency test is carried out to isolate these false positives from the screen.

First, nucleic acids are isolated from yeast transformants using any of the standard methods available (see, for instance, MATCHMAKER System 3 User Manual, Clontech). The nucleic acid mixture contains (1) the bait construct, (2) the prey construct and (3) genomic DNA from the yeast reporter strain. In order to selectively isolate the prey construct, the nucleic acid mixture is transformed into an appropriate *E. coli* strain, which can be any *E. coli* strain suitable for cloning purposes, but which preferably is any of the strains DH5alpha, DH10B, JM109, TOP10, XL-10 GOLD, SURE and which most preferably is the strain XL1-BLUE. The transformants are plated on standard bacterial culture plates supplemented with the antibiotic whose corresponding resistance gene is encoded on the prey construct. This can be any antibiotic but preferably is the antibiotic ampicillin. Since *E. coli* that have been transformed with either the bait construct or with fragments of yeast genomic DNA cannot grow on selective plates with the antibiotic ampicillin, all colonies arising on those plates are transformants carrying the prey construct. Large amounts of the prey construct are then isolated using any of the standard techniques for plasmid isolation from *E. coli* (Bedbrook & Ausubel, 1976, Sambrook & Russell, 2001); Plasmid Isolation Kit, Macherey Nagel AG, Düiren, Germany, Plasmid Isolation Kit, Quiagen Inc., Madison, Wis., USA).

The isolated library constructs are cotransformed into an appropriate yeast reporter strain, which can be AH109, Y190, L40, PJ694A, DSY1 or DSY2 but which preferably is either of Y187 or L40, together with (1) the bait construct and (2) a control bait construct encoding an unrelated bait polypeptide, which can be any polypeptide, but which preferably is any of Ost1, Wbp1, Alg5, ErbB3 and which most preferably is Alg5. The yeast transformants are plated on appropriate selective plates as described in section 7 and colonies that have survived selection are assayed for the activity of the lacZ reporter.

The following outcomes are possible:

(1) The prey polypeptide interacts with the original bait polypeptide and the control polypeptide. In this case, cotransformants of bait construct and prey construct, as well as cotransformants of control bait construct and prey construct will activate the lacZ reporter. Such prey constructs encode likely false positives that unspecifically interact with any bait polypeptide expressed in the same yeast cell and are sorted out.

(2) The prey polypeptide interacts with the original bait polypeptide but not with the control polypeptide. In this case, cotransformants of bait construct and prey construct, but not cotransformants of control bait construct and prey construct will activate the lacZ reporter. Such prey constructs encode true positives that interact only with the bait polypeptide.

9. Sequencing of Library Inserts

Any library constructs that are bait-dependent i.e. they interact with the original bait polypeptide but not with the control polypeptide) most likely encode a polypeptide that interacts with the bait polypeptide in yeast. To identify the polypeptide, the nucleic acid sequence in the library construct which encodes the prey polypeptide is determined using standard DNA sequencing methodology. The determined nucleic acid sequence can then be used to predict the corresponding polypeptide it encodes, and the nucleic acid sequence or the derived amino acid sequence can be used to search any public database holding sequence information, such as GenBank or the EMBL database, using any algorithm for the comparison of nucleic acid or amino acid sequences (such as BLAST, (Altschul et al., 1997).

The sequence of the polypeptide that is identified in this way may encode a protein that is already known to interact with the bait or it may encode a novel interactor. The most important advantage of the MbY2H system as compared to other methods for the detection of protein-protein interactions involving membrane-associated proteins is that it delivers not only the identity of the interacting protein but also all or part of the nucleic acid sequence encoding it. The nucleic acid sequence can be used by the investigator in numerous ways to conduct further experiments in order to verify and characterize the interaction between the proteins found in the MbY2H screen.

Meaningful Results of the Screen

Simultaneous expression of a particular bait polypeptide and a particular prey polypeptide in a yeast cell yields a transformant that survives selection by specifically activating the reporter genes by means of a reconstitution of split-ubiquitin from CbM and NbM fused to the bait and prey, respectively. Selection is carried out on selective media and confirmed by a calorimetric assay (section 7 above). The ability to reconstitute split-ubiquitin implies close spatial proximity of the bait and prey polypeptides and therefore, it is likely (depending on the stringency used in the screen) that the two polypeptides used as bait and prey interact in yeast. If the two polypeptides interact in yeast, this is a strong indication that they also interact in vivo in other settings, such as in a mammalian cell. Thus, the MbY2H system can be used to identify pairs of interacting proteins by using a predetermined protein (the bait) and a large collection (library) of other proteins (the preys). The MbY2H provides a means of identifying selectively those proteins that interact with the bait.

In another application of the system, the stringency threshold is set so low that also very weak and especially transient interactions are detected by the same mechanism. This implies transient spatial proximity between the bait polypeptide and the prey polypeptide. Using such a low stringency screen the MbY2H system can serve as a method to determine all proteins that at one point are spatially very close to the bait polypeptide.

Reporter Strains

1. L40

The yeast reporter strain L40 has the following genotype: MATa his3☐200 trp1-901 leu2-3112 ade2 LYS2::(4lexAop-HIS3) URA3::(8lexAop-lacZ) GAL4. The construction of L40 is described in detail in (Vojtek et al., 1993). L40 can be used to select for interacting bait and prey polypeptides using the MbY2H system as described in section 5. To select yeast transformants expressing interacting bait and prey polypeptides, the HIS3 reporter gene and the lacZ reporter gene are used.

2. AH109

The yeast reporter strain AH109 has the following genotype: MATa, trp1-901, leu2-3, 112, ura3-52, his3-200, gal4☐, gal80☐, LYS2:: GAL1(UAS)-GAL1(TATA)-HIS3, MEL1 GAL2(UAS)-GAL2(TATA)-ADE2, URA3::MEL1 (UAS)-MEL1 (TATA)-lacZ. The construction of AH109 is described in detail in the MATCHMAKER System 3 User Manual (Clontech). AH109 can be used to select for interacting bait and prey polypeptides using the MbY2H system as described in section 5. To select yeast transformants expressing interacting bait and prey polypeptides, the HIS3 marker, the ADE2 marker, the MEL1 marker and the lacZ marker are used. As compared to L40, the advantage of AH109 lies in the option to vary the stringency of the screen by using the following modifications in the selective medium: (1) low stringency: selective medium lacking the amino acids leucine, tryptophan and histidine. (2) medium stringency: selective medium lacking leucine, tryptophan and adenine. (3) high stringency: selective medium lacking, tryptophan, histidine and adenine.

3. PJ69-4A

The yeast reporter strain PJ69-4A has the following genotype: MATa trp1-901 leu2-3, 112 ura3-52 his3-200 gal4☐ gal80☐ LYS2::GAL1-HIS3 GAL2-ADE2 met2:: GAL7-lacZ. The construction of PJ69-4A is described in detail in (James et al., 1996). PJ69-4A can be used to select for interacting bait and prey polypeptides using the MbY2H system as described above. To select yeast transformants expressing interacting bait and prey polypeptides, the HIS3 marker, the ADE2 marker and the lacZ marker are used. As compared to L40, the advantage of PJ69-4A lies in the option to vary the stringency of the screen by using the following modifications in the selective medium: (1) low stringency: selective medium lacking leucine, tryptophan and histidine. (2) medium stringency: selective medium lacking leucine, tryptophan and adenine. (3) high stringency: selective medium lacking leucine, tryptophan, histidine and adenine.

4. DSY1

The yeast reporter strain DSY1 contains the following reporter cassettes integrated into the genome: GAL1 promoter followed by HIS3 gene, GAL2 promoter followed by ADE2 gene, GAL1 promoter followed by lacZ gene. DSY1 is constructed as follows: The yeast strain used for construction of DSY1 is DGY63, which has a high transformation efficiency. Reporter constructs encoding GAL1-HIS3, GAL2-ADE2 and GAL1-lacZ are subcloned into the integrative plasmid pFA6a(URA3) (Gietz & Sugino, 1988) using standard methods and are integrated into the DGY63 genome by multiple rounds of URA3 selection and 5-FOA-mediated pop-out, as described in (James et al., 1996). The negative reporter construct containing a hybrid promoter consisting of four LexA operator sites and a CYC1 upstream activating sequence, followed by the URA3 gene and the CYC1 terminator. The expression cassette containing the minimal CYC1 promoter, followed by the nucleic acid sequence encoding a control bait polypeptide fused to LexM-B42-CYC1 terminator is subcloned into the integrative plasmid pFA6a(kanMX) using standard yeast methodology (Burke et al., 2000) and is integrated into the genome using G418-mediated selection as described in (Burke et al., 2000). Alternatively, a variant of DSY1 can be constructed by integration of the negative reporter into the genome of AH109 or PJ69-4A as described above.

To select yeast transformants expressing interacting bait and prey polypeptides, the HIS3 marker, the ADE2 marker and the lacZ marker are used. As compared to L40, the advantage of DSY1 lies in the option to vary the stringency of the screen by using the following modifications in the selective medium: (1) low stringency: selective medium lacking leucine, tryptophan and histidine and containing the compound 5-FOA. (2) medium stringency: selective medium lacking, tryptophan and adenine and containing the compound 5-FOA. (3) high stringency: selective medium lacking, tryptophan, histidine and adenine and containing the compound 5-FOA.

As compared to AH109 and PJ69-4A, the advantage of DSY1 lies in the option to carry out a bait-dependency test simultaneously during the screening procedure, as described above.

5. DSY2

DSY2 is constructed in a similar fashion as DSY1, except that the integrated cassette contains 4xLexA operator sites-CYC1-UAS-FAR1-CYC1 terminator and CYC1 promoter-nucleic acid sequence encoding control bait polypeptide-LexM-B42-CYC1 terminator on the integrative plasmid pFA6a(kanMX).

To select yeast transformants expressing interacting bait and prey polypeptides, the HIS3 marker, the ADE2 marker and the lacZ marker are used. As compared to L40, the advantage of DSY2 lies in the option to vary the stringency of the screen by using the following modifications in the selective medium: (1) low stringency: selective medium lacking the amino acids leucine, tryptophan and histidine. (2) medium stringency: selective medium lacking the amino acids leucine, tryptophan and adenine. (3) high stringency: selective medium lacking the amino acids leucine, tryptophan, histidine and adenine.

As compared to AH109 and PJ69-4A, the advantage of DSY2 lies in the option to carry out a bait-dependency test simultaneously during the screening procedure, as described above.

As compared to DSY1, the advantage of DSY2 lies in the fact that the selective medium does not have to be supplemented with the compound 5-FOA.

6. L40alpha

L40alpha is a derivative strain of L40, which has been switched to the opposite mating type (from a to alpha) using standard procedures (Burke et al., 2000). It is used together with L40 in the mating variation of the screening procedure described above.

7. Y187

The yeast reporter strain Y187 has the following genotype: MA Talpha ura3-52 his3-200 ade2-101 trp1-901 leu2-3, 112 gal4☐ met-gal80☐ URA3::GAL1(UAS)-GAL1 (TATA)-lacZ MEL1. Its construction is described in detail in (Harper et al., 1993). It is used together with AH109 in the mating variation of the screening procedure described above.

8. PJ69-4Alpha

PJ69-4alpha is a derivative strain of PJ694A, which has been switched to the opposite mating type (from a to alpha) using standard procedures (Burke et al., 2000). It is used together with PJ69-4A in the mating variation of the screening procedure described above.

9. DSYM

DSYM is a derivative strain of DGY63, which has been switched to the opposite mating type (from a to alpha) using standard procedures (Burke et al., 2000). It is used together with DSY1 or DSY2 in the mating variation of the screening procedure described above.

10. DSYDS1

Constructed from DGY63 by knocking out the yeast PDR1-3 genes (which encode transcription factors regulating the expression of Erg transporters in yeast) using standard methodology (Burke et al., 2000). A reporter cassette containing GAL1-URA3 and GAL1-lacZ is integrated into the URA3 locus using standard methodology (Burke et al., 2000).

11. DSYDS2

Constructed from DGY63 by knocking out the yeast PDR1-3 genes (which encode transcription factors regulating the expression of Erg transporters in yeast) using standard methodology (Burke et al., 2000). A reporter cassette containing GAL1-FAR1 and GAL1-lacZ is integrated into the URA3 locus using standard methodology (Burke et al., 2000).

Real-Time Reporter Element to Detect NbM-CbM Association to Form Split-Ubiquitin 1. A reporter consisting of a firefly luciferase-CbM-GFP (FCG) fusion can be used to detect protein-protein interactions in real time. Activation of luciferase leads to fluorescent energy transfer (FRET) across the CbM to GFP, which becomes activated and emits green light. If a bait protein fused to FCG and a prey protein fused to NbM are coexpressed in yeast, the interaction of the two proteins results in the reconstitution of split-ubiquitin and the cleavage of the CbM-GFP boundary. GFP is liberated and diffuses away from the luciferase-CbM fusion. Consequently, no FRET between luciferase and GFP takes place. If a compound is introduced that blocks the interaction between bait and prey protein, GFP is not cleaved off anymore and FRET between luciferase and GFP will result in the emission of green light. Thus, the effectiveness of a compound in blocking the interaction between two proteins can be measured directly by the intensity of GFP fluorescence.

2. Reporter Strain DSYDS3

DSYDS3 is derived from strain DSYDS2 by integrating a reporter cassette containing CYC1-luciferase-CbM-GFP into the LYS2 locus using standard methodology (Burke et al., 2000).

Applications of the MbY2H System

Screening for Small Compounds that Disrupt a Defined Protein-Protein Interaction The aim of a small compound screen is to identify small compounds that can block a protein-protein interaction between a bait polypeptide and a prey polypeptide. The term "small compound" is meant to signify any small molecule with a molecular weight up to 5 kDa, which can be chemically synthesized, extracted or enriched from natural products, or which can be polysaccharide compounds.

A small compound library is any collection of the above-mentioned small compounds, which can be a combinatorial library, a library of defined chemically synthesized compounds, a library of random chemical compounds, a library of natural compounds, a library of natural extracts. The number of compounds in this library may be smaller than 100 compounds, 100-1000 compounds, 1000-10000 compounds, or more than 10000 compounds.

Usually, such a library is supplied in an arrayed format, e.g. in multiwell microtiter plates, but it may also be supplied as pools of compounds or as a compound mixture. The identity of each compound in each well may be known or it may be unknown. There may be one or several compounds in each well.

The screening procedure is carried out as follows: a reporter strain, which may be any appropriate yeast strain, but which preferably is one of the strains described in the section "Reporter strains", is transformed with a bait construct and a prey construct using any of the standard procedures described above. A bait construct contains a nucleic acid sequence encoding a bait polypeptide that is inserted into any of the bait vectors described in the section "bait vectors". A prey construct contains a nucleic acid sequence encoding a prey polypeptide inserted into any of the prey vectors described in the section "prey and library vectors". A prerequisite for the screening is that the bait and prey polypeptides interact in the reporter strain in a way such that the reassociation of CbM and NbM into split-ubiquitin takes place and that consequently, the reporter gene(s) is/are activated as described above. Transformants expressing bait and prey polypeptides are arrayed in 96-well or 384-well microtiter plates in selective medium.

When using the reporter strain DSYDS1, selective medium is any minimal medium lacking leucine (to select for the presence of the bait plasmids), tryptophan (to select for the presence of the prey construct). The transformants are grown for 1-5 cell divisions in the selective medium. Compounds from any of the compound libraries described above are added to the wells, together with the appropriate amount of 5-FOA (to select against the protein-protein interaction). Yeast transformants are grown and wells which contain viable yeast transformants are identified by measuring the optical density of the wells using standard procedures (Burke et al., 2000).

Two outcomes are possible:

(1) The added compound does not inhibit the interaction between the bait and the prey polypeptide. In this case, the bait and prey polypeptides will be spatially close, reconstitution of NbM and CbM will take place and split-ubiquitin will be formed. Since split-ubiquitin is formed, the transcriptional activator polypeptide will be cleaved off by ubiquitin-specific proteases and the transcriptional activator polypeptide will diffuse to the nucleus of the yeast cell. As a consequence, the URA3 reporter of the yeast transformant is activated and will produce the URA3 gene product. The URA3 gene product converts 5-FOA into a toxic metabolite that is used by the yeast cell and ultimately leads to cell death. No growth takes place in the well containing the particular yeast transformant and a decrease in the optical density is measured.

(2) The added compound does inhibit the interaction between the bait and the prey polypeptide. In this case, the bait and prey polypeptides will not be spatially close, reconstitution of NbM and CbM will not take place and split-ubiquitin will not be formed. Since split-ubiquitin is not formed, the transcriptional activator polypeptide will not be cleaved off by ubiquitin-specific proteases and the transcriptional activator polypeptide will remain attached to the bait polypeptide at the membrane. As a consequence, the URA3 reporter of the yeast transformant is not activated and no production of the URA3 gene product takes place. As the compound 5-FOA is not converted to its toxic metabolite, and because 5-FOA on its own has no negative effect on the yeast cell, the yeast transformant will continue to grow in the selective media. The growth of the particular yeast transformant is measured as an increase in optical density in the well.

When using the reporter strain DSYDS2, selective medium is any minimal medium lacking leucine (to select for the presence of the bait plasmids), tryptophan (to select for the presence of the prey construct). The transformants are grown for 1-5 cell divisions in the selective medium. Compounds from any of the compound libraries described above are added to the wells. Yeast transformants are grown and wells which contain viable yeast transformants are identified by measuring the optical density of the wells using standard procedures (Burke et al., 2000).

Two outcomes are possible:

(1) The added compound does not inhibit the interaction between the bait and the prey polypeptide. In this case, the bait and prey polypeptides will be spatially close, reconstitution of NbM and CbM will take place and split-ubiquitin will be formed. Since split-ubiquitin is formed, the transcriptional activator polypeptide will be cleaved off by ubiquitin-specific proteases and the transcriptional activator polypeptide will diffuse to the nucleus of the yeast cell. As a consequence, the FAR1 reporter of the yeast transformant is activated and will produce the FAR1 gene product. The FAR1 gene product will interfere with proteins involved in the cell cycle of yeast and will lead to cell cycle arrest. No growth takes place in the well containing the particular yeast transformant and a no change in the optical density is measured.

(2) The added compound does inhibit the interaction between the bait and the prey polypeptide. In this case, the bait and prey polypeptides will not be spatially close, reconstitution of NbM and CbM will not take place and split-ubiquitin will not be formed. Since split-ubiquitin is not formed, the transcriptional activator polypeptide will not be cleaved off by ubiquitin-specific proteases and the transcriptional activator polypeptide will remain attached to the bait polypeptide at the membrane. As a consequence, the FAR1 reporter of the yeast transformant is not activated and no production of the FAR1 gene product takes place. Consequently, the yeast transformant continues to grow. The growth of the particular yeast transformant is measured as an increase in optical density in the well.

Screening for Peptides that Disrupt a Defined Protein-Protein Interaction

Peptide aptamers are small proteins selected from combinatorial libraries that can bind to and modify the enzymatic activity of a certain protein, and thus represent a useful way for manipulating protein function in vivo (Fields & Stemglanz, 1994, Yang et al., 1995). Such combinatorial peptide libraries were so far generated on the surface of filamentous phage or were synthesized chemically and coupled to a carrier matrix such as resin beads.

Peptide aptamers are produced from expression libraries. A peptide aptamer library is constructed by inserting nucleic acid fragments encoding defined or random peptides of variable lengths (which can be peptide fragments of 4-16 amino acids, or peptide fragments longer than 16 amino acids) into an appropriate expression vector, such as p426GAL (Mumberg et al., 1995) using standard procedures (Sambrook & Russell, 2001).

Peptide aptamers may be secreted from the yeast cell or may remain in the cytoplasm of the yeast cell. If the localization of the peptides is to be cytoplasmatic, no modifications are necessary. If the peptides are to be secreted, they are engineered to contain an N-terminal secretion signal, such as the leader sequence of the yeast invertase (SUC2) polypeptide.

A nucleic acid sequence encoding the bait polypeptide and a nucleic acid sequence encoding the prey polypeptide are inserted into the screening vector pDSdual-1 described in the section "bait vectors" using standard procedures (Sambrook & Russell, 2001) or the in vivo cloning procedure described above.

A bait/prey construct, which is the construct pDSdual-1 expressing a bait and a prey polypeptide fused to CbM and NbM, respectively, which interact in yeast, and a peptide aptamer library are cotransformed into a yeast reporter strain using any of the methods described above. Preferably, the bait/prey construct and the peptide aptamer library are combined in the yeast reporter strain using the mating method described above. The yeast reporter strain can be any appropriate yeast strain but preferably is the strain DSYDS1 or the yeast strain DSYDS2.

When using DSYDS1, transformants are plated on selective medium lacking leucine (to select for pDSdual-1) and tryptophan (to select for the library construct encoding the peptide) and containing the compound 5-FOA.

When using DSYDS2, transformants are plated on selective medium lacking leucine (to select for pDSdual-1) and tryptophan (to select for the library construct encoding the peptide).

Outcome of the Screen:

(1) The peptide does not disrupt the binding of the bait polypeptide to the prey polypeptide. In this case, the bait and prey polypeptides will be spatially close, reconstitution of NbM and CbM will take place and split-ubiquitin will be formed. Since split-ubiquitin is formed, the transcriptional activator polypeptide will be cleaved off by ubiquitin-specific proteases and the transcriptional activator polypeptide will diffuse to the nucleus of the yeast cell. As a consequence, the URA3 (DSYDS1) or the FAR1 (DSYDS2) reporter of the yeast transformant is activated and will produce the Ura3 or Far1 gene product. The Ura3 gene product converts 5-FOA into a toxic metabolite that is used by the yeast cell and ultimately leads to cell death, whereas the Far1 gene product interferes with the cell cycle and arrests the yeast transformants. Consequently, the transformants do not grow on the selection plates.

(2) The peptide does inhibit the interaction between the bait and the prey polypeptide. In this case, the bait and prey polypeptides will not be spatially close, reconstitution of NbM and CbM will not take place and split-ubiquitin will not be formed. Since split-ubiquitin is not formed, the transcriptional activator polypeptide will not be cleaved off by ubiquitin-specific proteases and the transcriptional activator polypeptide will remain attached to the bait peptide at the membrane. As a consequence, the URA3 (DSYDS1) or FAR1 (DSYDS2) reporter of the yeast transformant is not activated and no production of the Ura3 or Far1 gene product takes place. Consequently, the yeast transformant continues to grow. Growth of particular transformants results in visible yeast colonies on the selection plates.

Screening for scFvs that Disrupt a Defined Protein-Protein Interaction

Single-chain antibodies (scFvs), synthesized by the cell and targeted to a particular cellular compartment, can be used to interfere in a highly specific manner with cell growth and metabolism. Like peptides, they may be secreted or may be intracellular (so-called intrabodies) (Richardson & Marasco, 1995).

scFvs are produced from expression libraries. A scFv library is constructed by inserting nucleic acid fragments encoding a defined scFv framework and hypervariable regions into an appropriate expression vector, such as p426GAL (Mumberg et al., 1995) using standard procedures (Sambrook & Russell, 2001). The construction and use of scFv libraries has been described numerous times, for example in connection with their use in phage display (Auf der Maur et al., 2001, Boder & Wittrup, 1997, Gram et al., 1998).

The screening procedure for scFvs is identical to that described for peptides.

Minimal Interaction Domain Mapping

This approach involves the identification of a minimal interaction domain (MID) of a bait or a prey protein, which is capable of blocking the interaction between said bait or prey protein. First, a bait protein is expressed as fusion to CbM and a prey protein is expressed as fusion to NbM. Then, MID libraries of the bait and prey proteins are constructed by fragmentation of the cDNAs encoding those proteins into fragments of variable size and subcloning those fragments into a library vector. The library vector may be chosen so as to express the MIDs in the cytoplasm of the cell, or it may contain a secretion signal that is used to direct the export of the MIDs into the periplasmic space. Then, a screening approach as described for peptide libraries may be used to identify those MIDs that block the interaction between the bait and the prey protein. The corresponding cDNA is then isolated and analysed further.

MID libraries are made by fragmentation of nucleic acids encoding (1) the bait polypeptide (the sequence may be supplied as a PCR product amplified from any nucleic acid construct encoding the bait polypeptide or as the nucleic acid construct itself) and (2) the prey polypeptide (the sequence may be supplied as a PCR product amplified from any nucleic acid construct encoding the bait polypeptide or as the nucleic acid construct itself). For each bait and prey polypeptide, a separate MID library is constructed. Alternatively, the libraries may be mixed or a mixed library consisting of bait and prey fragments may be made. The average size of the nucleic acid fragments in the library may be chosen to suit the experimental purposes. Fragments may range from 50 nucleotides up to 5000 nucleotides but preferably, they are in the size range of 100-500 nucleotides or 500-1000 nucleotides. Fragments may be made by any appropriate method, but preferably, they are made by random shearing through sonification. After sonification, fragments are repaired using standard procedures (Sambrook & Russell, 2001) and are inserted into an appropriate expression vector, such as p426GAL (Mumberg et al., 1995). MID libraries may be made to contain secreted MIDs or they may express the MIDs in the cytoplasm. If the MIDs are to be secreted, they are engineered to contain an N-terminal secretion signal, such as the leader sequence of the yeast invertase (SUC2) polypeptide.

The nucleic acid sequences encoding the bait and prey polypeptides are cloned into the construct pDSdual-1, using any of the methods described.

The screening procedure for MIDs is identical to that described for peptides.

Screening for Antibody Epitopes Against a Defined Antigen scFVs may also be used to identify novel antibodies that bind to a given protein. In this case, scFv libraries are constructed where the scFvs are fused to a flexible polypeptide linker of 10-20 amino acids, followed by a transmembrane domain, followed by NbM. The actual construction of the scFv library follows standard methods.

Introduction of a library plasmid encoding a scFv fusion results in the expression of an integral membrane protein, where the scFv portion is located on the lumenal side of the membrane and the NbM is located on the cytoplasmatic side.

A bait construct is made by inserting a nucleic acid fragment encoding the polypeptide to be used as antigen (e.g. the polypeptide against which the final antibody is directed) into any of the bait constructs using standard methods (Sambrook & Russell, 2001).

The bait construct and the library are cotransformed into a suitable reporter strain using any of the methods described in the section "library screening procedure". Preferably, bait and library are coexpressed using the mating procedure described in the section "library screening procedure". Any suitable reporter strain may be used, but preferably, DSY1 or DSY2 is used.

The screening procedure follows that described for a conventional MbY2H screen outlined in the section "library screening procedure".

Orphan G Protein-Coupled Receptor Screening

G protein coupled receptors (GPCRs) represent the single most important class of therapeutical targets today. From the complete human genome sequence, it is estimated that there are several hundred different G protein coupled receptors expressed in human tissues, the majority of which are uncharacterized to date. So-called orphan receptors are GPCRs for which no endogenous ligand has been identified. There is great pharmaceutical interest in orphan receptors because they represent potentially novel therapeutic targets (Wilson & Bergsma, 2000).

Unactivated receptor (e.g. receptor that is not bound to an agonist or a ligand) is complexed with heterotrimeric G proteins which bind to the cytoplasmic domains of the receptor. Binding of an agonistic compound to a GPCR results in a conformational change of the receptor, which leads to the dissociation of the G alpha subunit from the receptor and from the G beta and G gamma subunits. Both G alpha and G beta may then activate several signalling components that mediate downstream signalling (Gudermann et al., 1997).

Screening for ligands that bind to orphan receptors is an important field in pharmaceutical research. Today, most orphan receptor screens are carried out either in vitro, using partially purified membrane fractions containing the receptor under investigation, or in vivo, using mammalian cell lines that overexpress the GPCR in question. Both approaches have drawbacks: in vitro screening does not adequately represent the in vivo situation and is cumbersome and expensive due to the large amounts of partially purified receptor that have to be prepared. In contrast, in vivo screenings put the receptor in its natural setting, but the presence of other endogenous receptors with the identical or similar specificities may influence the screening results due to cross-talk between the receptors and their signalling cascades. Yeast represents an interesting alternative to the abovementioned approaches. Screening is carried out in a cellular setting, thus preserving most physiological parameters, but cross-talk between receptors is abolished since yeast only expressed two GPCRs and only 3 G proteins, as composed to the hundreds of different GPCRs and dozens of G proteins that are expressed in mammalian cells.

GPCRs have been successfully expressed in yeast and it most cases, the pharmacological fingerprint of the original receptor is preserved (Pausch, 1997, Reilander & Weiss, 1998). Although the glycosylation pattern in yeast is not identical to that of mammalian cells, it has been shown glycosylation is often not necessary for the specific binding of ligands by GPCRs (King et al., 1990).

In order to adapt the MbY2H system for the identification of ligands for orphan receptors, the following steps are necessary.

Bait Construction

A nucleic acid sequence encoding the GPCR under investigation is inserted into any of the bait constructs described using any of the standard methods described in the section "library screening". Preferentially, the nucleic acid sequence encoding the bait receptor is inserted into pCMGA74B42. The signal sequence directing the correct insertion of the receptor into the membrane may be the original signal sequence of the receptor or preferentially, the original signal sequence of the receptor is replaced by a signal sequence derived from a yeast polypeptide such as the yeast GPCR Ste2p or yeast invertase (SUC2).

Verification of Correct Expression

Following transformation into an appropriate reporter strain, which may be any reporter strain listed in the section "reporter strains" but which preferentially is DSY1 or DSY2 and most preferentially, DSYDS1 or DSYDS2, the receptor is expressed as a fusion to CbM and a reporter moiety, which may any of the reporter moieties described in the section "bait vectors" but which preferably is Gal1-93-B42 and most preferably, Gal1-74-B42. Verification that the receptor is correctly expressed and integrated into the membranes may be carried out using any of the methods described in the section "library screening".

Prey Construction

For the purpose of an orphan receptor ligand screen, the prey is defined as any protein that interacts with the receptor under investigation in a manner such that the interaction is abolished upon ligand binding. Preferentially, the prey is any G alpha subunit or any G beta subunit of a heterotrimeric G protein complex and most preferentially, it is a promiscuous G alpha subunit such as human G alpha 16 or murine G alpha 13. The nucleic acid sequence encoding the G protein may be inserted into any of the library or prey constructs described in the section "prey and library vectors" but preferentially, it is inserted into p424CUP1-NbM-x or p424CUP1-x-NbM. The constructs p424CUP1-NbM-x or p424CUP1-x-NbM are identical to p424NbM-x and p424x-NbM, respectively, except that the CYC1 promoter has been replaced by a CUP1 promoter. The G protein may either be fused N-terminally or C-terminally to NbM. The correct expression of the prey may be verified using any of the standard methods described in the section "library screening".

Screening

Screening is initiated by cotransforming bait and prey constructs into any of the reporter strains described. Following transformation, the yeast transformants are expanded in selective medium lacking the amino acids leucine (to select for the presence of the bait construct) and tryptophan (to select for the presence of the prey construct). Following expansion, liquid yeast cultures are aliquoted into 96-well or 384-well plates. Expression of the bait and prey polypeptides are induced by the addition of copper to the medium, and directly afterwards, a particular compound from a compound library is added to each well. When using DSYDS1, the compound 5-FOA is added together with the copper to the medium. The compound library may be any of the compound libraries described above or it may be any compound library that has been manufactured expressively for the purpose of orphan receptor ligand screening. Aliquoting the yeast strain, addition of copper and addition of compounds is done in a automated fashion using standard high throughput screening methodology.

The following outcomes are possible:

(1) The added compound does not bind the receptor. In this case, no conformational change in the receptor takes place and the majority of all heterotrimeric G proteins will remain bound to the receptor. The spatial proximity of G alpha and the GPCR leads to the reconstitution of NbM and CbM and the formation of split-ubiquitin. Since split-ubiquitin is formed, the transcriptional activator polypeptide will be cleaved off by ubiquitin-specific proteases and the transcriptional activator polypeptide will diffuse to the nucleus of the yeast cell. As a consequence, the URA3 (DSYDS1) or the FAR1 (DSYDS2) reporter of the yeast transformant is activated and will produce the Ura3 or Far1 gene product. The Ura3 gene product converts 5-FOA into a toxic metabolite that is used by the yeast cell and ultimately leads to cell death, whereas the Far1 gene product interferes with the cell cycle and arrests the yeast transformants. Consequently, the transformants do not grow in the selection medium.

(2) The added compound binds and activates the receptor. The conformational change following receptor activation leads to the dissociation of the G proteins from the receptor. In this case, the bait (receptor) and prey (G alpha or G beta) polypeptides will not be spatially close, reconstitution of NbM and CbM will not take place and split-ubiquitin will not be formed. Since split-ubiquitin is not formed, the transcriptional activator polypeptide will not be cleaved off by ubiquitin-specific proteases and the transcriptional activator polypeptide will remain attached to the bait polypeptide at the membrane. As a consequence, the URA3 (DSYDS1) or FAR1 (DSYDS2) reporter of the yeast transformant is not activated and no production of the Ura3 or Far1 gene product takes place. Consequently, the yeast transformant continues to grow. Growth of particular transformants in the selection media is then measured by measuring the optical density of the yeast culture.

Modification 1

In a modification of the procedure described above, the receptor can be expressed as an unfused polypeptide from any suitable yeast expression vector (such as p424GAL1 or p424CYC1, Mumberg et al., 1995) and the bait and prey polypeptides are expressed from pDSdual-2. The construct pDSdual-2 is identical to pDSdual-1 described in the section "bait vectors", except that the CYC1 promoters have been replaced by CUP1 promoters. In this modification, the bait is any G alpha subunit, but preferably a promiscuous alpha subunit such as human G alpha 16, and the prey is any G beta subunit. The expression, the verification of expression and the screening are carried out exactly as described above. In this case, binding of a ligand to the receptor induces dissociation of the G protein complex and therefore leads to the spatial separation of G alpha and G beta. Spatial separation of G alpha and G beta prevents formation of split-ubiquitin by NbM and CbM and prevents expression of URA3 (DSYDS1) or FAR1 (DSYDS2), leading to growth of the transformant in selective medium.

Modification 2

In another modification of the procedure described above, the receptor is expressed as an unfused polypeptide from any suitable yeast expression vector (such as p424GAL1 or p424CYC1, Mumberg et al., 1995) and the bait and prey polypeptides are expressed from pDSdual-2. The bait is adenylate cyclase and the prey is any G alpha subunit, but preferably a promiscuous alpha subunit such as human G alpha 16. For screening any suitable yeast reporter strain can be used, but preferably, L40, AH109 or PJ69-4A and most preferably, DSY1 or DSY2 is used.

The expression, the verification of expression and the screening are carried out exactly as described above, except that the selective medium is lacking leucine (to select for pDSdual-2, tryptophan (to select for the expression construct encoding the receptor) and adenine and histidine. The stringency of the screen may be varied by supplementing either adenine or histidine, as described in the section "library screening procedure".

The following outcomes are possible:

(1) The added compound does not bind the receptor. In this case, no conformational change in the receptor takes place and the majority of all heterotrimeric G proteins will remain bound to the receptor. If G alpha remains bound to the receptor, it cannot reach adenylate cyclase and consequently, NbM and CbM are not spatially close and no split-ubiquitin is formed. Since no split-ubiquitin is formed, the transcriptional activator polypeptide will not be cleaved off by ubiquitin-specific proteases and the transcriptional activator polypeptide is unable to reach the nucleus of the yeast cell. As a consequence, the reporter genes of the yeast transformant are not activated and will not produce any reporter protein. Therefore, the respective yeast transformant will be unable to grow in the selective medium.

(2) The added compound binds and activates the receptor. The conformational change following receptor activation induces dissociation of G alpha from G beta and G gamma, followed by binding of G alpha to adenylate cyclase. The cloese spatial proximity of G alpha and adenylate cyclase brings NbM and CbM into close proximity, leading to the reconstitution of split-ubiquitin. Since split-ubiquitin is formed, the transcriptional activator polypeptide will be cleaved off by ubiquitin-specific proteases and the transcriptional activator polypeptide will diffuse to the nucleus of the yeast cell. As a consequence, the reporter genes of the yeast transformant are activated and will produce the reporter protein.

Therefore, the respective yeast transformant will be able to grow in the selective medium. Growth of particular transformants in the selection media is then measured by measuring the optical density of the yeast culture.

Modification 3

This modification is used to specifically select compounds that bind one GPCR but a related GPCR. For example, GPCR 1 (the bait) may be the beta2 adrenergic receptor and GPCR 2 (the control) may be the beta1 adrenergic receptor. The use of modification 3 in screening will lead to the isolation of compounds that selectively activate the beta2 adrenergic receptor but not the beta1 adrenergic receptor. The identification of novel compounds that show no unspecific cross-talk between GPCRs of the same subclass or even between unrelated GPCRs is of enormous importance for the pharmaceutical industry.

In modification 3 the nucleic acid sequence encoding a G alpha subunit, which may be any G alpha subunit but which preferably is human G alpha 16, is inserted into the construct pDS-INbM such that a fusion of G alpha 16 and NbM results.

pDS-INbM is an integrative vector carrying the following expression cassette: the cassette contains a CYC1 promoter for low level expression in yeast, followed by a multiple cloning site containing multiple recognition sites for restriction endonucleases and sequences for the in vivo cloning described in the section "library screening procedures", followed by the sequence encoding NbM, followed by a CYC1 terminator.

Alternatively, the cassette may contain a CUP1 promoter instead of a CYC1 promoter to allow the inducible expression of the fusion polypeptide.

The backbone of the construct contains elements necessary for the integration of the construct into the yeast genome, such as a kanMX cassette and appropriate homology regions. Furthermore, the vector contains the kanamycine resistance cassette for selection in E. coli, and the pUC origin of replication for propagation in E. coli.

This vector is suitable for the low level or inducible expression of a NbM-fused polypeptide.

The construct encoding adenylate cyclase and a G alpha subunit in pDS-Idual-1 is integrated into the genome of an appropriate reporter strain using standard methods (Burke et al., 2000), which may be any reporter strain but which preferably is DSYDS1 or most preferably DSYDS2.

The nucleic acid sequence encoding the GPCR for which ligands are to be found (termed GPCR 1) is inserted into any of the bait vectors described in section 2, but preferably into pCUP1-CbM-DB42, which is identical to pCUP1-CbM-TDA, but where the nucleic acid sequence encoding VP16 has been replaced by the nucleic acid sequence encoding B42 and where the LEU2 marker has been replaced by TRP1 marker. When transformed into yeast, this construct expresses a fusion polypeptide between GPCR 1 and LexM-B42.

The nucleic acid sequence encoding the GPCR which must not bind ligands that bind to GPCR1 (termed GPCR 2) is inserted into any of the bait vectors described in section 2, but preferably into pCGA74B42 or pCGA93B42. When transformed into yeast, this construct expresses a fusion polypeptide between GPCR 2 and Gal4 amino acids 1-74-B42.

The yeast reporter strain carrying the integrated construct is transformed with the two constructs encoding GPCR GPCR 2 baits and grown in selective medium lacking the amino acids tryptophan (to select for the construct encoding GPCR 1) and leucine (to select for the construct encoding GPCR 2).

Yeast transformants are aliquoted into 96-well or 384-well plates and selective medium lacking the amino acids leucine, tryptophan and the compound adenine (to select against activation of GPCR 2) compound is added. Following the addition of the compound, copper is added to induce expression of the GPCRs and if DSYDS1 is used, 5-FOA is added.

Selection is carried out as described above.

The following outcomes are possible:

(1) The added compound does not bind the GPCR 1. In this case, no conformational change in the receptor takes place and the majority of all heterotrimeric G proteins will remain bound to the receptor. The spatial proximity of G alpha and the GPCR leads to the reconstitution of NbM and CbM and the formation of split-ubiquitin. Since split-ubiquitin is formed, LexA-B42 will be cleaved off by ubiquitin-specific proteases and will diffuse to the nucleus of the yeast cell. As a consequence, the URA3 (DSYDS1) or the FAR1 (DSYDS2) reporter of the yeast transformant is activated and will produce the Ura3 or Far1 gene product. The Ura3 gene product converts 5-FOA into a toxic metabolite that is used by the yeast cell and ultimately leads to cell death, whereas the Far1 gene product interferes with the cell cycle and arrests the yeast transformants. Consequently, the transformants do not grow in the selection medium.

(2) The added compound binds to GPCR1 and not to GPCR 2. The conformational change following receptor activation leads to the dissociation of the G proteins from GPCR 1. In this case, the bait (receptor) and prey (G alpha) polypeptides will not be spatially close, reconstitution of NbM and CbM will not take place and split-ubiquitin will not be formed. Since split-ubiquitin is not formed, LexM-B42 will not be cleaved off by ubiquitin-specific proteases and will remain attached to the bait polypeptide at the membrane. As a consequence, the URA3 (DSYDS1) or FAR1 (DSYDS2) reporter of the yeast transformant is not activated and no production of the Ura3 or Far1 gene product takes place. Consequently, the yeast transformant continues to grow. Since GPCR 2 is not activated by the compound, G alpha-NbM remains bound to GPCR 2, the close spatial proximity of CbM and NbM leads to their association to form split-ubiquitin and the Gal-B42 polypeptide is cleaved off and activates the ADE2 reporter. Therefore, the transformants survive selection in the selection medium lacking adenine. Growth of particular transformants in the selection media is then measured by measuring the optical density of the yeast culture.

(3) The added compound binds to GPCR 1 (with the outcome described in (2)) but also to GPCR 2. The conformational change in GPCR 2 leads to the dissociation of G alpha-NbM from GPCR 2. Since the ubiquitin-specific proteases do not recognize the CbM moiety alone, the Gal-B42 polypeptide is not cleaved off. Consequently, the ADE2 reporter is not activated and the transformant does not grow in the selection medium.

EXAMPLES

Example 1

MbY2H Screen Using the Beta2 Adrenergic Receptor as a Bait

Bait Cloning

The bait vector pCbM-TDA described in the section "bait vectors" was modified by insertion of the leader sequence from the yeast STE2 gene into the Xba I and Pst I sites. The sequence of the leader was exactly as described by (King et al., 1990). The coding sequence of the human beta2 adrenergic receptor was amplified from human genomic DNA (Promega Corporation, Madison, Wis., USA) and cloned into the vector pSte-CbM-FLV.

Verification of Expression

Correct expression of the receptor was verified by western blotting using an antibody directed against the VP16 domain (Clontech). In the yeast strain L40 expressing the construct pBAR-CbM-TDA, a double band at 75 and 100 kDa was visible (FIG. 9A). No bands were visible in control extracts of L40 transformed with a vector supplying the LEU2 resistance marker. The presence of the receptor in membranes of L40 was verified using a standard membrane fractionation method as described in the section "library screening procedure". As shown in FIG. 9B, the receptor was only found in the membrane fraction, but not in the soluble fraction.

Self-Activation Test

Self-activation of the receptor-LexA-VP16 fusion was assessed by testing growth of transformants on selective medium lacking the amino acids histidine, leucine and tryptophane and containing 15 mM 3-AT and by assaying beta-galactosidase activity using a standard filter test. Transformants expressing the receptor showed no activity in the beta-galactosidase assay.

Screening Against a NbM-x Library

A screen was carried out using a human brain NbM-x library constructed by Life Technologies (Carlsbad, Calif., USA). Cotransformation and growth on selective plates was performed as described in the section "library screening procedure". Selection yielded approximately 300 colonies. Following a beta-galactosidase filter assay on the primary selection plates, 96 colonies showing strong induction of beta-galactosidase activity were picked and restreaked on selective media. Following a second beta-galactosidase filter assay, 59 positive clones were processed for western blotting and plasmid isolation as described in the section "library screening procedure". Library plasmids were reintroduced into L40 together with either pBAR-CbM-TDA or the control construct pErbB3-TDA, encoding the human ErbB3 receptor fused to CbM-LexM-VP16, and assayed for growth on selective plates and beta-galactosidase activity. Of 59 clones, 19 scored as bait-dependent, i.e. they interacted with the beta2 adrenergic receptor but not with the ErbB3 receptor. Plasmids from bait dependent clones were sequenced.

Example 2

Filter Assay for the Detection of β-Galactosidase Activity

1. The yeast expressing Y-CbM-TDA are grown together with NbM-fusion proteins for two days at 30° C. on sterile Whatman filters on drop-out agar plates lacking leucine and tryptophan. The drop-out-medium is used because cells tend to grow poorly in standard minimal medium.

2. Using forceps, the filter is transferred and dipped into liquid nitrogen for 3 min and allowed to thaw at room temperature.

3. The filters are overlaid with 1.5% agarose in 0.1 M $NaPO_4$-buffer (pH 7.0) containing 0.4 mg/ml X-gal.

4. The filters are incubated at 30° C. for 0.4-24 hours.

Example 3

Quantitation of β-Galactosidase Activity

1. Yeast transformants expressing Y-CbM-TDA are inoculated together with NbM-fusion proteins into 3 ml of liquid drop-out medium lacking uracil, leucine and tryptophan.

2. Incubation at 30° C. until cultures reach midlog phase ($OD_{546}$~1.0).

3. Cells are pelleted from 1 ml of culture, washed once in Z buffer, and resuspend in 300 µl Z-buffer.

4. 100 µl cells are taken and lysed by 3 freeze/thaw cycles.

5. 700 µl Z-buffer containing 0.27% (v/v) β-mercaptoethanol and 160 µl ONPG (4 mg/ml in Z-buffer) are added and incubated for 1-20 hours at 30° C.

6. 400 µl 0.1 M $NaCO_3$ are added, the samples centrifuged, and the $OD_{420}$ is measured.

7. The β-galactosidase activity is calculated using the formula:

$$\beta\text{-galactosidase units}=1000\times OD_{420}/(OD_{546}\times min)$$

Example 4

Western Blot Analysis of Cells Expressing Y-CbM-TDA Together with NbM-Fusions

1. Yeast cells expressing Y-CbM-TDA together with NbM-fusion proteins are grown at 30° C. to an $OD_{546}$ of 0.3-1.2 in drop-out liquid medium lacking leucine and tryptophan.

2. The cells are pelleted and resuspended in 50 µl 1.85 M NaOH per 3 OD units of cells, and incubated on ice for 10 min.

3. The same volume of 50% trichloroacetic acid is added, and the proteins are precipitated by centrifugation for 5 min.

4. The pellet is resuspended in 50 µl of SDS-sample buffer containing 8 M urea.

5. 20 µl of 1 M Tris.base is added and the protein is dissolved at 37° C. (heating to 95° C. sometimes results in the clumping of membrane proteins).

6. The samples are centrifuged for 2 min. and 10 µl extract is used for SDSPAGE/Western blotting analysis.

7. The amount of protein loaded by Coomassie staining of the SDS-gels is verified.

8. The membranes are probed with peroxidase-IgG at 1:5000 dilution. Protein A-fusion proteins are detected by enhanced chemiluminescence (Pierce of Amersham).

Example 5

Interactions Between Heterologous Proteins in Yeast can be Detected Using the MbY2H System To demonstrate the usefulness of the MbY2H system in detecting protein-protein interactions between two heterologous proteins situated at the membrane in yeast, two defined protein pairs were selected. In the first example, the homodimerization of presenilin-1 N-terminal fragments is demonstrated and serves as an example of an interaction between two integral membrane proteins. In the second case, the interaction between the receptor tyrosine kinase ErbB3 and its adaptor protein Nrdp1 was chosen to demonstrate the interaction between an integral membrane protein and a soluble (cytosolic) protein.

Definition of Bait and Prey Vectors

1. PCMBV1. The vector pCMBV1 corresponds to the vector pCbM-TDA described on page 21, except that the sequence encoding the 3xFLAG epitope has been removed (FIG. 13A).

2. pAMBV1. The vector pAMBV1 is identical to pCMBV1, except that the weak CYC1 promoter has been replaced by a strong ADH1 promoter (FIG. 13B).

3. DDSL-Nx. The vector pDSL-Nx corresponds to the vector p424NbM-X described on page 37 (FIG. 14A).

4. pADSL-Nx. The vector pADSL-Nx corresponds to the vector pNbM-HA-X described on page 36 (FIG. 14B).

5. pDSL-xN. The vector pDSL-xN corresponds to the vector p424X-NbM described on page 37 (FIG. 14C).

6. pADSL-xN. The vector pADSL-xN corresponds to the vector pX-HA-NbM described on page 36 (FIG. 14D).

Homodimerization of Presenilin-1 N-Terminal Fragments

Presenilin-1 is a polytypic membrane protein with eight transmembrane domains. In its mature form, the protein is a dimer of an N-terminal (NTF) and a C-terminal (CTF) fragment which are generated from intact presenilin-1 by endoproteolytic cleavage in a cytosolic loop located between transmembrane domains 6 and 7. The two fragments remain associated at a stoichiometric ratio of 1:1 and form a very stable complex. Currently, the precise function of presenilin-1 is still under debate but it has been shown numerous times that the protein is an essential part of a multiprotein complex termed gamma-secretase. The gamma-secretase complex is involved in proteolytic processing of a number of transmembrane proteins, among them APP (amyloid precursor protein) and members of the Notch family (Esler and Wolfe, 2001).

The homodimerization of NTFs has been demonstrated previously using the Split-ubiquitin method described by Stagljar and coworkers (Stagljar et al., 1998; Cervantes et al., 2001). Therefore this interaction was chosen to investigate whether it can also be detected using the novel vectors containing different promoters and the LexM moiety. FIG. 10A shows a schematic description of bait and prey in the MbY2H system. The interaction between NTF bait and NTF prey should lead to the reconstitution of split-ubiquitin from Cub and NubG and consequent cleavage of the peptide bond between Cub and LexM-VP16 (Rep in FIG. 10A). Transport of LexM-VP16 to the nucleus and its binding to LexA operators then activates the reporter genes, whose readout is measured either by growth on selective media or by assaying beta-galactosidase activity. FIG. 10 B shows the outcome of the experiment. Yeast reporter strain L40 was cotransformed with different baits and preys and transformed cells were plated on minimal medium selecting for the presence of both plasmids. Following growth at 30° C. for 3 days, 10 colonies of each transformant were resuspended in 0.9% NaCl and aliquots were spotted onto minimal medium to select for protein-protein interactions. Growth on selective medium indicates that the bait and prey interact. Low level expression of bait and prey from a weak CYC1 promoter (pCMBV1-NTF and pDSL-NubG-NTF) does not allow for the detection of the interaction, whereas increasing the expression level of the bait (pAMBV1-NTF and pDSL-NubG-NTF) leads only to modest growth on selective medium. Expression of the prey at high levels (pADSL-NubG-NTF) is sufficient to detect the interaction both with low level and high level expression of the bait. Neither bait interacts with a non-cognate control prey expressed at high levels (pMBV1-Alg5-NubG).

Interaction of ErbB3 with the C-Terminal Part of Nrdp1

The receptor tyrosine kinase ErbB3 is a member of the family of Erb receptors, which also contains ErbB1 (also called EGFR, epidermal growth factor receptor), ErbB2 and ErbB4. They mediate diverse signals influencing essential cellular responses such as differentiation, proliferation and survival (Olayioye et al., 2000). Nrdp1 is a ring finger containing protein whose C-terminal domain has been found to interact with the cytosolic tail of ErbB3 in a yeast two-hybrid assay (Qiu and Goldberg, 2002).

To assay the interaction between ErbB3 and Nrdp1 bait and prey constructs were transformed into the yeast strain L40 as indicated in FIG. 11, spotted onto selective plates and grown at 30° C. for 3 days. Strong growth on selective medium lacking histidine is seen for ErbB3 and Nrdp1 when expressed at high levels (FIG. 11a), whereas neither ErbB3 in combination with the control prey expressed from pADSL-Alg5 (FIG. 11c) nor Nrdp1 in combination with the control bait expressed from pMBV1-Alg5 (FIG. 11b) show any growth on selective medium. Again, this demonstrates that high level expression of bait and prey in the MbY2H system allows the detection of an interaction between an integral membrane protein and its cytosolic binding partner.

Example 6

Self-Activation Levels of Constructs Bearing the Wild Type and Mutated LexA Sequences To demonstrate that screening for protein-protein interactions is not possible using the vectors described in Stagljar et al. (1998) due to the inherent self-activation of the bait-LexA-Cub-ProteinA-VP16 fusion proteins, self-activation levels of constructs bearing the wild type and the mutated LexA sequence were compared when cotransformed with non-cognate (non-interacting) preys. Coexpression of the beta2-adrenergic receptor bait in the vector pCAS (carrying the wild type LexA sequence) together with either a non-interacting control prey encoding the yeast protein Ost1 fused to NubG or a control prey encoding only NubG with a membrane anchor resulted in growth on selective medium and strong beta-galactosidase activity (Table 1, rows 1 and 2). In contrast, the beta2-adrenergic receptor bait expressed from the vector pCbM-TDA (carrying the LexM sequence with the R157G mutation to decrease the strength of the nuclear localization signal) did not grow on selective medium and did not show any beta-galactosidase activity when coexpressed with either of the two control preys (Table 1, rows 3 and 4). Thus, while the high background of the original bait vector described by Stagljar et al. (1998) would result in an unacceptably high background of false positives in a MbY2H screen, the novel vectors described here decrease this background significantly to allow screening of an integral membrane protein bait against cDNA or genomic libraries.

TABLE 1

Comparison of self-activation levels of wild type and mutated LexA bait constructs.

| Row | Bait | Prey | Colonies on SD-HTL | Beta-galactosidase activity |
|---|---|---|---|---|
| 1 | pCAS-bAR | pOst1-NubG | 6 | very strong |
| 2 | pCAS-bAR | pMP-NubG | 200 | very strong |
| 3 | pBAR-LM1 | pOst1-NubG | 0 | negative |
| 4 | pBAR-LM1 | pMP-NubG | 0 | negative |

The entire open reading frame of the beta2-adrenergic receptor (beta2-AR) was cloned into several bait vectors to yield the following constructs: (1) pCAS-bAR: beta2-AR inserted into the vector pCAS carrying wild type LexA. (2) pBAR-LM1: beta2-AR inserted into pCbM-TDA containing the R157G mutation in LexA to decrease the strength of nuclear localization signal. The following prey constructs were used: (1) pOst1-NubG: the entire open reading frame of the yeast protein Ost1 inserted into pX-HA-NbM. (2) pMP-NubG: a signal conferring fatty acid modification inserted into pX-HA-NbM. Different combinations of bait and prey constructs were cotransformed into the yeast strain L40 and growth was assayed on minimal medium lacking the amino acids tryptophan, leucine and histidine. The bait construct containing the wild type LexA showed activated both reporter genes in the absence of a valid protein-protein interaction, resulting in growth on SD-HTL and strong Beta-galactosidase activity. In contrast, an identical construct bearing the mutated LexA sequence did not show any activation of the reporter genes in the absence of a protein-protein interaction.

Example 7

MbY2H Screen Using a Modified Bait Vector and the Beta2-Adrenergic Receptor as a Bait The screen was performed using a human brain NubG-x cDNA library. The beta2-adrenergic receptor was inserted into the bait vector pCbM-TDA carrying the LexM sequence (LexA with the R157G mutation to decrease the strength of the nuclear localization signal). Library scale transformation and growth on selective medium was performed as described in the section "library screening procedure". Selection for histidine prototrophy and beta-galactosidase activity yielded 122 colonies. When restreaked on selective medium, 103 of the 122 colonies showed reproducible histidine prototrophy and beta-galactosidase activity. The positive 103 colonies were processed by Western blotting and plasmid isolation, and inserts were analyzed by 5'-sequencing. Eleven of the sequenced clones encoded ATPases (four proton transporting and seven calcium transporting ATPases). Seven clones encoded potassium voltage-gated channels and five clones encoded NADH-dehydrogenase subunits. The fact that multiple clones were found that encode similar classes of proteins was taken as evidence that these clones indeed encode putative interactors of the beta2-adrenergic receptor. Furthermore, all clones encode integral membrane proteins. A bait-dependency test was carried out on a total of 16 clones, using the endogenous yeast membrane proteins Alg5 and Ost1 as control. 13 clones were found to be bait dependent (FIG. 12).

REFERENCES

Altschul, S. F., Madden, T. L., Schaffer, A. A., Zhang, J., Zhang, Z., Miller, W., & Lipman, D. J. (1997) *Nucleic Acids Res* 25, 3389-402.
Angermayr, M., Strobel, G., Muller, G., & Bandlow, W. (2000) *FEBS Lett.* 481, 8-12.
Auf der Maur, A., Escher, D., & Barberis, A. (2001) *FEBS Lett* 508, 407-12.
Bedbrook, J. R., & Ausubel, F. M. (1976) *Cell* 9, 707-16.
Boder, E. T., & Wittrup, K. D. (1997) *Nat Biotechnol* 15, 553-7.
Burke, D., Dawson, D., & Stearns, T. (2000) *Methods in yeast genetics*, Cold Spring Harbor Laboratory Press.
Cervantes, S., Gonzalez-Duarte, R. and Marfany, G. (2001) *FEBS Lett.* 505, 81-86
Chubet, R. G., & Brizzard, B. L. (1996) *Biotechniques* 20, 136-41.
Dunnwald, M., Varshavsky, A., & Johnsson, N. (1999) *Mol Biol Cell* 10, 329-44.
Esler, W. and Wolfe, M. S. (2001) *Science* 293, 1449-1454
Olayioye M. A., Neve R. M., Lane H. A., Hynes N. E. (2000) *EMBO J.* 19, 3159-3167
Evan, G. I., Lewis, G. K., Ramsay, G., & Bishop, J. M. (1985) *Mol. Cell. Biol.* 5, 3610-3616.
Fields, S., & Song, O.-K. (1989) *Nature* 340, 245-246.
Fields, S., & Stemglanz, R. (1994) *Trends Genet* 10, 286-92.
Fogh, R. H., Ottleben, G., Ruterjans, H., Schnarr, M., Boelens, R., & Kaptein, R. (1994) *Embo J* 13, 393-644.
Friedberg, E. C. (1991a) *Bioessays* 13, 295-302.
Friedberg, E. C. (1991b) *Mol Microbiol* 5, 2303-10.
Fuentes, J. M., Lompre, A. M., Moller, J. V., Falson, P., & le Maire, M. (2000) *Anal Biochem* 285, 276-8.
Fusco, C., Guidotti, E., & Zervos, A. S. (1999) *Yeast* 15, 715-20.
Gardner, K. H., Pan, T., Narula, S., Rivera, E., & Coleman, J. E. (1991) *Biochemistry* 30, 11292-302.
Gietz, R. D., & Sugino, A. (1988) *Gene* 74, 527-34.
Gietz, R. D., & Woods, R. A. (2001) *Biotechniques* 30, 816-20, 822-6, 828 passim.
Golemis, E. A., Serebriiskii, I., & Law, S. F. (1999) *Curr. Issues Mol. Biol.* 1, 31-45.
Gram, H., Schmitz, R., & Ridder, R. (1998) *Methods Mol Biol* 103, 179-92.
Gubler, U. (1988) *Nucleic Acids Res* 16, 2726.
Gudermann, T., Schoneberg, T., & Schultz, G. (1997) *Annu Rev Neurosci* 20, 399-427.

Harper, J. W., Adami, G. R., Wei, N., Keyomarsi, K., & Elledge, S. J. (1993) *Cell* 75, 805-16.
Hernan, R., Heuermann, K., & Brizzard, B. (2000) *Biotechniques* 28, 789-93.
Hershko, A., & Ciechanover, A. (1992) *Annu Rev Biochem* 61, 761-807.
Hughes, S. R., Goyal, S., Sun, J. E., Gonzalez-DeWhitt, P., Fortes, M. A., Riedel, N. G., & Sahasrabudhe, S. R. (1996) *Proc Natl Acad Sci USA* 93, 2065-70.
James, P., Halladay, J., & Craig, E. A. (1996) *Genetics* 144, 1425-36.
Johnsson, N., & Varshavsky, A. (1994) *Proc. Natl. Acad. Sci. USA* 91, 10340-4.
King, K., Dohlman, H. G., Thorner, J., Caron, M. G., & Lefkowitz, R. J. (1990) *Science* 250, 121-3.
Laser, H., Bongards, C., Schuller, J., Heck, S., Johnsson, N., & Lehming, N. (2000) *Proc Natl Acad Sci USA* 97, 13732-7.
Macreadie, I. G., Jagadish, M. N., Azad, A. A., & Vaughan, P. R. (1989) *Plasmid* 21, 147-50.
Mullis, K. B. (1990) *Ann Biol Clin* 48, 579-82.
Mumberg, D., Muller, R., & Funk, M. (1995) *Gene* 156, 119-22.
Oldenburg, K. R., Vo, K. T., Michaelis, S., & Paddon, C. (1997) *Nucleic Acids Res* 25, 451-2.
Overton, M. C., & Blumer, K. J. (2000) *Curr Biol* 10, 341-4.
Pan, T., & Coleman, J. E. (1989) *Proc Natl Acad Sci USA* 86, 3145-9.
Pausch, M. H. (1997) *Trends Biotechnol* 15, 487-94.
Prado, F., & Aguilera, A. (1994) *Curr Genet* 25, 180-3.
Qiu, X. and Goldberg A. L. (2003) *Proc. Natl. Acad. Sci. USA* 99, 14843-14848
Reilander, H., & Weiss, H. M. (1998) *Curr Opin Biotechnol* 9, 510-7.
Richardson, J. H., & Marasco, W. A. (1995) *Trends Biotechnol* 13, 306-10.
Sambrook, J., & Russell, D. W. (2001) *Molecular Cloning*, Cold Spring Harbor Laboratory Press.
Serebriiskii, I. G., & Golemis, E. A. (2001) *Methods Mol. Biol.* 177, 123-34.
Shen, F., Triezenberg, S. J., Hensley, P., Porter, D., & Knutson, J. R. (1996) *J Biol Chem* 271, 4827-37.
Soellick, T. R., & Uhrig, J. F. (2001) *Genome Biol* 2.
Stagljar, I., Korostensky, C., Johnsson, N., & te Heesen, S. (1998) *Proc Natl Acad Sci USA* 95, 5187-92.
Vojtek, A. B., Hollenberg, S. M., & Cooper, J. A. (1993) *Cell* 74, 205-214.
Wilson, I. A., Niman, H. L., Houghten, R. A., Cherenson, A. R., Connolly, M. L., & Lerner, R. A. (1984) *Cell* 37, 767-78.
Wilson, S., & Bergsma, D. (2000) *Drug Des Discov* 17, 105-14.
Wittke, S., Lewke, N., Muller, S., & Johnsson, N. (1999) *Mol Biol Cell* 10, 2519-30.
Wolven, A., Okamura, H., Rosenblatt, Y., & Resh, M. D. (1997) *Mol. Biol. Cell* 8, 1159-73.
Wu, T. J., Monokian, G., Mark, D. F., & Wobbe, C. R. (1994) *Mol Cell Biol* 14, 3484-93.
Yang, M., Wu, Z., & Fields, S. (1995) *Nucleic Acids Res* 23, 1152-6.

The invention claimed is:

1. A method for detecting an interaction between a first membrane bound protein or part thereof and a second protein or part thereof, which is either membrane bound or soluble, the method comprising:
   (a) providing a host cell containing at least one detectable gene (reporter gene) having a binding site for a transcriptional activator, such that the detectable gene expresses a detectable product when the detectable gene is transcriptionally activated;
   (b) providing, as part of a bait vector, a first chimeric gene under the control of a promoter, said first chimeric gene being expressed in said host cell and coding inter alia for a first membrane protein or part thereof which gene is attached to the DNA-sequence of a first module encoding inter alia a first protein sequence involved in intracellular protein degradation and a transcriptional activator, said first protein or part thereof to be tested whether it can interact with a second protein or part thereof, wherein said bait vector is a plasmid construct;
   (c) providing, as a part of a prey vector, a second chimeric gene under the control of a promoter that can be expressed in said host cell, the second chimeric gene coding inter alia for a second protein or part thereof which is either membrane bound or soluble and which gene is attached to the DNA sequence of a second module encoding inter alia a second protein sequence involved in intracellular protein degradation, wherein said prey vector is a plasmid construct;
   (d) introducing the bait vector and the prey vector into the host cell such that an interaction between the expressed first and second proteins and/or their parts can take place, which interaction leads to an interaction of the first protein sequence of the first module and the second protein sequence of the second module which interaction in turn leads to activation of an intracellular protease and proteolytic separation of the transcriptional activator, wherein both the bait vector and the prey vector are maintained episomally;
   (e) determining whether the detectable gene of the host cell has been activated by the transcriptional activator; and
   (f) detecting said interaction between said first membrane bound protein or part thereof and said second protein or part thereof.

2. The method according to claim 1, wherein the host cell is a yeast, a bacterium or a mammalian cell.

3. The method according to claim 2, wherein the yeast is *Saccharomyces pombe* or *Saccharomyces cerevisiae*.

4. The method according to claim 1, wherein the detectable gene is activated by an activator comprising a short tagging module.

5. The method according to claim 1, wherein the detectable gene is activated by the artificial transcriptional activator protein A-LexA-V16 (PLV).

6. The method according to claim 1, wherein the first protein sequence comprises a C-terminal portion of ubiquitin (Cub) or a mutant thereof (CbM) and the second protein sequence comprises an N-terminal portion of ubiquitin (Nub) or a mutant thereof (NbM).

7. The method according to claim 1, wherein the DNA-sequence coding for the first membrane protein is selected from the group consisting of any bacterial membrane protein, any viral membrane protein, any oncogene-encoded membrane protein, any growth factor receptor or any eukaryotic membrane protein, or parts thereof.

8. The method according to claim 1, wherein the second membrane protein or the soluble protein, or part thereof, is encoded by a plasmid library.

9. The method according to claim 1, wherein the first membrane protein is a soluble protein attached artificially to the membrane via fusion to a signal sequence which encodes a membrane anchor.

10. A kit for detecting binding between a first membrane bound protein or part thereof and a second protein or part thereof which is either membrane bound or soluble comprising:
   (a) a host cell containing at least one detectable gene (reporter gene) having a binding site for a transcriptional activator, such that the detectable gene expresses a detectable product when the detectable gene is transcriptionally activated;
   (b) a first vector (bait), which is a plasmid construct that is maintained episomally, comprising a first site that can receive a first nucleic acid coding for a first membrane protein or part thereof such that when the first nucleic acid is inserted it becomes attached to the DNA sequence of a first module encoding inter alia a first protein sequence involved in intracellular protein degradation, the first module further comprising a nucleic acid for a transcriptional activator and a promoter;
   (c) a second vector (prey), which is a plasmid construct that is maintained episomally, comprising a second site that can receive a second nucleic acid coding for a second membrane protein or a soluble protein or part thereof such that when the second nucleic acid is inserted it becomes attached to the DNA sequence of a second module encoding inter alia a sequence protein sequence involved in intracellular protein degradation, wherein the second module further comprises a promoter; and optionally (d) a plasmid library encoding second proteins or parts thereof, wherein binding between said first membrane bound protein or part thereof and said second protein or part thereof is detected.

11. The kit according to claim 10, wherein the host cell is a yeast, a bacterium or a mammalian cell.

12. The kit according to claim 11, wherein the yeast is *Saccharomyces pombe* or *Saccharomyces cerevisiae*.

13. The kit according to claim 10, wherein the detectable gene can be activated by an activator comprising a short tagging module.

14. The kit according to claim 10, wherein the detectable gene can be activated by the artificial transcriptional activator protein A-LexA-V16 (PLV).

15. The kit according to claim 10, wherein the first protein sequence contains Cub or CbM and the second protein sequence contains Nub or NbM.

16. The kit according to claim 10, wherein the promoter in (b) is a CYC1 promoter or a CUP1 promoter.

17. The kit according to claim 10, wherein the DNA sequence coding for the first membrane protein is derived from any bacterial membrane protein, any viral membrane protein, any oncogene-encoded membrane protein, any growth factor receptor or any eukaryotic membrane protein, or parts thereof.

18. The kit according to claim 10, wherein the DNA sequence coding for the second protein is contained in a plasmid library.

19. A vector comprising the following elements:
(a) a selection marker for propagation of the vector in *E. coli*;
(b) an origin of replication which allows propagation of the vector in *E. coli*;
(c) a further selection marker for propagation of the vector in yeast;
(d) an origin of replication which allows episomal propagation of the vector in yeast; and
(e) an expression cassette comprising the following elements:
  (i) a promoter element;
  (ii) a nucleic acid sequence encoding a leader selected from a signal sequence derived from a yeast integral membrane protein and a signal sequence, which confers fatty acid modification;
  (iii) a nucleic acid sequence encoding Cub or CbM;
  (iv) a nucleic acid sequence encoding a DNA binding protein; and
  (v) a nucleic acid sequence encoding a transcriptional activator, wherein said vector is a plasmid.

20. A host cell containing the vector of claim 19.

21. A method of identifying compounds comprising providing the kit of claim 10 and screening compounds for their ability to interfere with protein-protein interaction.

22. A method for providing a compound that can interfere with protein/protein interaction, which method comprises:

(a) providing a host cell according to claim 20, the bait and prey polypeptides being selected such that they interact when expressed;
(b) incubating the host cell in the presence and absence of the compound(s) to be tested;
(c) measuring the difference in reporter gene expression between the incubation containing the compound(s) to be tested and the incubation free of the compound(s) to be tested; and optionally
(d) purifying or synthesizing the compound that interferes with protein-protein interaction.

23. The method of claim 21, wherein said compound is a pharmaceutical drug.

24. The method of claim 1, wherein the bait vector is a low copy vector.

25. The method of claim 24, wherein the bait vector is present in 1 to 2 copies per cell.

26. The vector of claim 19, wherein said origin of replication in (d) is a CEN/ARS origin of replication.

27. A vector comprising the following elements:
(a) a selection marker for propagation of the vector in *E. coli*;
(b) an origin of replication which allows propagation of the vector in *E. coli*;
(c) a further selection marker for propagation of the vector in yeast;
(d) an origin of replication which allows episomal propagation of the vector in yeast; and
(e) an expression cassette comprising the following elements:
  (i) a promoter element;
  (ii) a nucleic acid sequence encoding a leader selected from a signal sequence derived from a yeast integral membrane protein and a signal sequence, which confers fatty acid modification;
  (iii) a nucleic acid sequence encoding Cub or CbM;
  (iv) a nucleic acid sequence encoding a DNA binding protein; and
  (v) a nucleic acid sequence encoding a transcriptional activator, wherein said vector is a plasmid, wherein said origin of replication in (d) is a CEN/ARS origin of replication and wherein the signal sequence encoded in (e)(ii) is: N-MGCTLSAEDKPGGP-C(SEQ ID No. 1).

28. The vector of claim 1, wherein said promoter in (b) is a promoter that confers low level expression.

29. The vector of claim 28, wherein said promoter in (b) is a CYC1 promoter.

30. The vector of claim 28, wherein said promoter in (b) is a CUP1 promoter.

31. The method of claim 1, wherein the bait vector propagates via a CEN/ARS origin of replication.

32. The method of claim 31, wherein the prey vector propagates via a CEN/ARS or 2 micron origin of replication.

33. The kit of claim 10, wherein the first vector propagates via a CEN/ARS origin of replication.

34. The kit of claim 33, wherein the second vector propagates via a CEN/ARS or 2 micron origin of replication.

* * * * *